US007371520B2

(12) United States Patent
Zhao et al.

(10) Patent No.: US 7,371,520 B2
(45) Date of Patent: May 13, 2008

(54) METHODS AND APPARATI USING SINGLE POLYMER ANALYSIS

(75) Inventors: Xiaojian (David) Zhao, Westford, MA (US); Jeffrey D. Randall, Canton, MA (US); Bijit Kundu, Brookline, MA (US); Jessica Kesty, Seabrook, NH (US); Steve R. Gullans, Natick, MA (US); Eugene Y. Chan, Brookline, MA (US); Martin Fuchs, Uxbridge, MA (US)

(73) Assignee: U.S. Genomics, Inc., Woburn, MA (US)

( * ) Notice: Subject to any disclaimer, the term of this patent is extended or adjusted under 35 U.S.C. 154(b) by 127 days.

(21) Appl. No.: 10/448,264

(22) Filed: May 28, 2003

(65) Prior Publication Data

US 2004/0009612 A1 Jan. 15, 2004

Related U.S. Application Data

(60) Provisional application No. 60/441,337, filed on Jan. 21, 2003, provisional application No. 60/441,334, filed on Jan. 20, 2003, provisional application No. 60/437,892, filed on Jan. 3, 2003, provisional application No. 60/383,968, filed on May 28, 2002.

(51) Int. Cl.
C12Q 1/68 (2006.01)
C07H 21/02 (2006.01)
C07H 21/04 (2006.01)

(52) U.S. Cl. .................. 435/6; 536/23.1; 536/24.3
(58) Field of Classification Search ............. 435/6; 536/23.1, 24.3
See application file for complete search history.

(56) References Cited

U.S. PATENT DOCUMENTS

| | | | |
|---|---|---|---|
| 4,707,797 A * | 11/1987 | Briggs ........................... | 435/6 |
| 4,793,705 A | 12/1988 | Shera | |
| 4,979,824 A | 12/1990 | Mathies et al. | |
| 4,988,617 A | 1/1991 | Landegren et al. | |
| 5,200,313 A | 4/1993 | Carrico | |
| 5,332,666 A | 7/1994 | Prober et al. | |
| 5,356,776 A | 10/1994 | Kambara et al. | |
| 5,422,271 A | 6/1995 | Chen et al. | |
| 5,538,848 A | 7/1996 | Livak et al. | |
| 5,538,898 A | 7/1996 | Wickramasinghe et al. | |
| 5,565,323 A | 10/1996 | Parker et al. | |
| 5,612,181 A | 3/1997 | Fourmentin-Guilbert | |
| 5,652,099 A | 7/1997 | Conrad | |
| 5,654,419 A | 8/1997 | Mathies et al. | |
| 5,707,797 A | 1/1998 | Windle | |
| 5,710,264 A * | 1/1998 | Urdea et al. ............ | 536/23.1 |
| 5,807,677 A | 9/1998 | Eigen et al. | |
| 5,858,671 A | 1/1999 | Jones | |
| 5,912,127 A | 6/1999 | Narod et al. | |
| 5,928,869 A | 7/1999 | Nadeau et al. | |
| 6,007,987 A | 12/1999 | Cantor et al. | |
| 6,020,126 A | 2/2000 | Carlsson et al. | |
| 6,090,552 A | 7/2000 | Nazarenko et al. | |
| 6,103,476 A | 8/2000 | Tyagi et al. | |
| 6,106,476 A | 8/2000 | Corl et al. | |
| 6,150,089 A | 11/2000 | Schwartz | |
| 6,210,896 B1 | 4/2001 | Chan | |
| 6,221,592 B1 | 4/2001 | Schwartz et al. | |
| 6,225,055 B1 | 5/2001 | Bensimon et al. | |
| 6,225,067 B1 | 5/2001 | Rogers | |
| 6,246,046 B1 | 6/2001 | Landers et al. | |
| 6,248,537 B1 | 6/2001 | Bensimon et al. | |
| 6,263,286 B1 | 7/2001 | Gilmanshin et al. | |
| 6,287,765 B1 | 9/2001 | Cubicciotti | |
| 6,287,772 B1 | 9/2001 | Stefano et al. | |
| 6,294,136 B1 | 9/2001 | Schwartz | |
| 6,344,319 B1 | 2/2002 | Bensimon et al. | |
| 6,355,420 B1 | 3/2002 | Chan | |
| 6,383,740 B2 | 5/2002 | Collins | |
| 6,403,311 B1 | 6/2002 | Chan | |
| 6,673,536 B1 | 1/2004 | Stoughton et al. | |
| 6,696,022 B1 | 2/2004 | Chan et al. | |
| 6,762,059 B2 | 7/2004 | Chan et al. | |
| 6,767,731 B2 | 7/2004 | Hannah | |
| 6,772,070 B2 | 8/2004 | Gilmanshin et al. | |
| 6,790,671 B1 | 9/2004 | Austin et al. | |
| 6,927,065 B2 | 8/2005 | Chan et al. | |
| 7,262,859 B2 | 8/2005 | Chan et al. | |
| 2002/0037506 A1 | 3/2002 | Lin et al. | |

(Continued)

FOREIGN PATENT DOCUMENTS

EP 0453301 A2 10/1991

(Continued)

OTHER PUBLICATIONS

Lee et al., 1993 "Allelic discrimination by nick-translation PCR with fluorogenic probes" Nucleic Acids Research, vol. 21, No. 16, pp. 3761-3766.

(Continued)

Primary Examiner—Ethan Whisenant
(74) Attorney, Agent, or Firm—Wolf, Greenfield & Sacks, P.C.

(57) ABSTRACT

The invention relates to methods for analyzing and characterizing single polymers such as nucleic acid molecules. In preferred embodiments, the single molecules are analyzed using single molecule detection and analysis systems.

28 Claims, 40 Drawing Sheets

U.S. PATENT DOCUMENTS

| | | |
|---|---|---|
| 2002/0039737 A1 | 4/2002 | Chan et al. |
| 2002/0110818 A1 | 8/2002 | Chan |
| 2002/0119455 A1 | 8/2002 | Chan |
| 2002/0187508 A1 | 12/2002 | Wong |
| 2002/0197639 A1 | 12/2002 | Shia et al. |
| 2003/0008414 A1 | 1/2003 | Nie et al. |
| 2003/0059822 A1 | 3/2003 | Chan et al. |
| 2003/0129611 A1* | 7/2003 | Bao et al. ............ 435/6 |
| 2003/0165929 A1 | 9/2003 | Rigler et al. |
| 2003/0215864 A1 | 11/2003 | Gilmanshin et al. |
| 2003/0235854 A1 | 12/2003 | Chan |
| 2004/0009612 A1 | 1/2004 | Zhao et al. |
| 2004/0053399 A1 | 3/2004 | Gilmanshin |
| 2004/0086879 A1* | 5/2004 | Li et al. ............ 435/6 |
| 2004/0166025 A1 | 8/2004 | Chan et al. |
| 2004/0175732 A1 | 9/2004 | Rana et al. |
| 2004/0214211 A1 | 10/2004 | Gilmanshin et al. |
| 2004/0235014 A1 | 11/2004 | Nadel et al. |
| 2005/0042665 A1 | 2/2005 | Gilmanshin |
| 2005/0074788 A1 | 4/2005 | Dahlberg et al. |
| 2005/0112595 A1 | 5/2005 | Zhao et al. |
| 2005/0112606 A1 | 5/2005 | Fuchs et al. |
| 2005/0112620 A1 | 5/2005 | Chan |
| 2005/0112671 A1 | 5/2005 | Maletta et al. |
| 2005/0123944 A1 | 6/2005 | Neely et al. |
| 2005/0123974 A1 | 6/2005 | Gilmanshin et al. |
| 2005/0142595 A1 | 6/2005 | Maletta et al. |
| 2005/0153354 A1 | 7/2005 | Gilmanshin et al. |
| 2005/0196790 A1 | 9/2005 | Rooke et al. |
| 2005/0221408 A1 | 10/2005 | Nalefski et al. |
| 2006/0078915 A1 | 4/2006 | Fuchs et al. |
| 2006/0134679 A1 | 6/2006 | Larson et al. |
| 2006/0160209 A1 | 7/2006 | Larson et al. |
| 2006/0160231 A1 | 7/2006 | Nadel et al. |
| 2006/0204978 A1 | 9/2006 | Nilsen et al. |
| 2006/0228747 A1 | 10/2006 | Fuchs et al. |
| 2006/0286570 A1 | 12/2006 | Rowlen et al. |
| 2006/0292616 A1 | 12/2006 | Neely et al. |
| 2006/0292617 A1 | 12/2006 | Neely et al. |
| 2007/0003950 A1 | 1/2007 | Shen et al. |
| 2007/0009954 A1 | 1/2007 | Yang et al. |
| 2007/0031829 A1 | 2/2007 | Yasuno et al. |
| 2007/0042400 A1 | 2/2007 | Choi et al. |
| 2007/0042406 A1 | 2/2007 | Yantz et al. |
| 2007/0042419 A1 | 2/2007 | Barany et al. |
| 2007/0128083 A1 | 6/2007 | Yantz et al. |
| 2007/0166743 A1 | 7/2007 | Gilmanshin |

FOREIGN PATENT DOCUMENTS

| | | |
|---|---|---|
| WO | 93/22463 A2 | 11/1993 |
| WO | WO98/10097 A2 | 3/1998 |
| WO | WO98/35012 A2 | 8/1998 |
| WO | 98/49344 A2 | 11/1998 |
| WO | WO 00/09757 A1 | 2/2000 |
| WO | WO 01/13088 A1 | 2/2001 |
| WO | 01-90418 A1 | 11/2001 |
| WO | 01/90418 A1 | 11/2001 |
| WO | WO 02/099398 A1 | 12/2002 |
| WO | WO 02/101095 A1 | 12/2002 |
| WO | WO 02/101353 A2 | 12/2002 |
| WO | 03/000933 A1 | 1/2003 |
| WO | WO 03/025540 A2 | 3/2003 |
| WO | WO 03/076655 A2 | 9/2003 |
| WO | WO 03/091455 A1 | 11/2003 |
| WO | WO 03/100101 A1 | 12/2003 |
| WO | WO 2004/007692 A2 | 1/2004 |
| WO | WO 2004/048514 A2 | 6/2004 |
| WO | WO 2004/066185 A1 | 8/2004 |
| WO | WO 2004/091795 A2 | 10/2004 |
| WO | WO 2005/012575 A1 | 2/2005 |
| WO | WO 2005/017205 A2 | 2/2005 |
| WO | WO 2005/022162 A1 | 3/2005 |
| WO | 07/056250 A2 | 5/2007 |

OTHER PUBLICATIONS

Matthews et al., 1988 "Review: Analytical Strategies for the use of DNA Probes", Analytical Biochemistry, 169:1-25.

Chen et al., A homogeneous, ligase-mediated DNA diagnostic test. Genome Res. May 1998;8(5):549-56.

Marras et al., Multiplex detection of single-nucleotide variations using molecular beacons. Genet Anal. Feb. 1999;14(5-6):151-6.

Sokol et al., Real time detection of DNA.RNA hybridization in living cells. Proc Natl Acad Sci U S A. Sep. 29, 1998;95(20):11538-43.

Woodage et al., The APCI1307K allele and cancer risk in a community-based study of Ashkenazi Jews. Nat Genet. Sep. 1998;20(1):62-5.

Castro et al., Single-Molecule Electrophoresis: Applications to Biomolecular Detection. SPIE. 1995; 2396:79-85.

Castro et al., Single-molecule detection of specific nucleic acid sequences in unamplified genomic DNA. Anal Chem. Oct. 1, 1997;69(19):3915-20.

D'Antoni et al., Rapid quantitative analysis using a single molecule counting approach. Anal Biochem. May 1, 2006;352(1):97-109.

EkstrØm et al., Two-point fluorescence detection and automated fraction collection applied to constant denaturant capillary electrophoresis. Biotechniques. Sep. 2000;29(3):582-4, 586-9.

Heinze et al., Triple-color conicidence analysis: one step further in following higher order molecular complex formation. Biophys J. Jan. 2004;86(1 Pt 1):506-16.

Korn et al., Gene expression analysis using single molecule detection. Nucleic Acids Res. Aug. 15, 2003;31(16):e89.

Li et al., Ultrasensitive coincidence fluorescence detection of single DNA molecules. Anal Chem. Apr. 1, 2003;75(7):1664-70. Abstract Only.

Shera et al., Detection of single fluorescent molecules. Chem Phys Letts. Nov. 23, 1990;174(6):553-7.

Soper et al., Detection and identification of single molecules in solution. J Opt Soc Am B. 1992; 9(10):1761-9.

Shortreed et al., High-throughput single-molecule DNA screening based on electrophoresis. Anal Chem. Jul. 1, 2000;72(13):2879-85.

Ambrose et al., Application of single molecule detection to DNA sequencing and sizing, Ber. Bunsenges. Phys. Chem. 1993; 97:1535-1542.

Böhmer, Cell division analysis using bromodeoxyuridine-induced suppression of Hoechst 33258 fluorescence. Methods Cell Biol. 1990;33:173-84.

Caplin et al., LightCycler hybridization probes: the most direct way to monitor PCR amplification for quantification and mutation detection. Biochemica. 1999;1:5-8.

Chan et al., DNA mapping using microfluidic stretching and single-molecule detection of fluorescent site-specific tags. Genome Res. Jun. 2004;14(6):1137-46.

Heinze et al., Two-photon fluorescence coincidence analysis: rapid measurements of enzyme kinetics. Biophys J. Sep. 2002;83(3):1671-81.

Huang et al., DNA sequencing using capillary array electrophoresis. Anal Chem. Sep. 15, 1992;64(18):2149-54.

Kinjo et al., Ultrasensitive hybridization analysis using fluorescence correlation spectroscopy. Nucleic Acids Res. May 25, 1995;23(10):1795-9.

Lacoste et al., Ultrahigh-resolution multicolor colocalization of single fluorescent probes. Proc Natl Acad Sci U S A. Aug. 15, 2000;97(17):9461-6.

Lee et al., A fluorometic assay for DNA cleavage reactions characterized with BamHI restriction endonuclease. Anal Biochem. Aug. 1, 1994;220(2):377-83.

Lee et al., Laser-induced fluorescence detection of a single molecule in a capillary. Anal Chem. Dec. 1, 1994;66(23):4142-9.

Matayoshi et al., Novel fluorogenic substrates for assaying retroviral proteases by resonance energy transfer. Science. Feb. 23, 1990;247(4945):954-8.

Mergny et al., Fluorescence energy transfer as a probe for nucleic acid structures and sequences. Nucleic Acids Res. Mar. 25, 1994;22(6):920-8.

Mertz et al., Single-molecule detection by two-photon-excited fluorescence. Optics Letts. Dec. 15, 1995;20(24):2532-4.

Metzger, Biotech: Speed Readers. Wired. Nov. 1998;8:4.

Nie et al., Probing individual molecules with confocal fluorescence microscopy. Science. Nov. 11, 1994;266(5187):1018-21.

Parra et al. High resolution visual mapping of stretched DNA by fluorescent hybridization. Nat Genet. Sep. 1993;5(1):17-21. Abstract Only.

Peck et al., Single-molecule fluorescence detection: autocorrelation criterion and experimental realization with phycoerythrin. Proc Natl Acad Sci U S A. Jun. 1989;86(11):4087-91.

Poot et al., Chapter 19: Cell cycle analysis using continuous bromodeoxyuridine labeling and Hoechst 33258-ethidium bromide bivariate flow cytometry. Methods Cell Biol. 1990;33:185-98..

Rampino et al., Apparatus for gel electrophoresis with continuous monitoring of individual DNA molecules by video epifluorescence microscopy. Anal Biochem. May 1, 1991;194(2):278-83.

Randall et al., Accurate and sensitive direct mRNA quantification from total RNA samples by single molecule counting. Biotechniques Live Meeting. The World Trade Center, Boston, MA. Mar. 5, 2003. Poster and Abstract.

Strezoska et al., DNA sequencing by hybridization: 100 bases read by a non-gel-based method. Proc Natl Acad Sci U S A. Nov. 15, 1991;88(22):10089-93.

Stryer et al., Fluorescence energy transfer as a spectroscopic ruler. Annu Rev Biochem. 1978;47:819-46.

Van Gijlswijk et al., Universal Linkage System: versatile nucleic acid labeling technique. Expert Rev Mol Diagn. May 2001;1(1):81-91. Abstract Only.

Wang et al., Fluorescence resonace energy transfer between donor-acceptor pair on two oligonucleotides hybridized adjacently to DNA template. Biopolymers. 2003;72(6):401-12.

Dittrich et al., Sorting of cells and single particles in microstructures. Biophysical Journal. Jan. 2002; 82(1):43a. Abstract only.

Eigen et al., Sorting single molecules: Application to diagnostics and evolutionary biotechnology, Proc Natl Acad Sci USA. Jun. 21, 1994;91(13):5740-7.

Ekstrøm et al., Two-point fluorescence detection and automated fraction collection applied to constant denaturant capillary electrophoresis. Biotechniques. Sep. 29, 2000;(3):582-4, 586-9.

Fan et al., Electrochemical detection of single molecules. Science. Feb 10, 1995; 267:871-4.

Goodwin et al., Spatial dependence of the optical collection effciency in flow cytometry. Cytometry. Oct. 1, 1995;21(2):133-44.

Haab et al., Single molecule flourescence burst detection of DNA fragments separated by capillary electrophoresis. Anal. Chem. Sep. 15, 1995; 67(18):3253-60. Abstract Only.

Ju et al., Cassette labeling for facile construction of energy transfer flourescent primers. Nucleic Acids Res. Mar. 15, 1996;24(6):1144-8.

Klar et al., Fluorescence microscopy with diffraction resolution barrier broken by stimulated emission. PNAS. Jul. 18, 2000; 97(15):8206-10.

Li et al., Molecule by molecule direct and quantitative counting of antibody-protein complexes in solution. Anal. Chem. Aug. 1, 2004;76(15):4446-51.

Nechyporuk-Zloy et al., Single plasma membrane K+ channel detection by using dual-color quantum dot labeling. Am J Physiol Cell Physiol. Aug. 2006;291(2):C266-9. Abstract Only.

Neely et al., A single-molecule method for the quantitation of microRNA gene expression. Nature Methods. Jan. 3, 1996; 3(1):41-46.

Nie et al., Optical detection of single molecules. Annu Rev Biophys Biomol Struct, 1997;26:567-96.

Nolan et al., A simple quenching method for fluorescence background reduction and its application to the direct, quantitative detection of specific mRNA. Anal Chem. Nov. 15, 2003;75(22):6236-43.

Ren et al., Analysis of human telomerase activity and function by two color single molecule coincidence flourescence spectroscopy. J Am Chem Soc. Apr. 19, 2006;128(15):4992-5000. Abstract Only.

Schwille et al. Dual-color fluorescence cross-correlation spectroscopy for multicomponent diffusional analysis in solution. Biophys J. Apr. 1997;72(4):1878-86.

Thomann et al., Automatic flourescent tag detection in 3D with super-resolution: application to the analysis of chromosome movement. J. of Microscopy. Oct. 1, 2002; 208(1):49-64.

Tobe et al., Single-well genotyping of diallelic sequence variations by a two-color ELISA-based oligonucleotide ligation assay. Nucleic Acids Res. Oct. 1, 1996;24(19):3728-32.

Uchiyama et al., Detection of undegraded oligonucleotides in Vivo by fluorescence resonance energy transfer. J. of Biol. Chemistry. Jan. 5, 1996; 271(1):380-4.

Wang et al., Rapid sizing of short tandem repeat alleles using capillary array electrophoresis and energy-transfer flourescent primers. Anal. Chem. 1995; 67:1197-1203.

Ambrose et al., Detection and Spectroscopy of single pentacene molecules in a p-terphenyl crystal by means of fluorescence excitation. J Chem Phys. Nov. 15, 1991;95(10):7150-7163.

Ambrose et al., Single molecule fluorescence spectroscopy at ambient temperature. Chem Rev. Oct. 13, 1999;99(10):2929-56. Abstract Only.

Aston et al., Optical mapping and its potential for large-scale sequencing projects. Tibtech. 1999;17:297-302.

Barad et al., MicroRNA expression detected by oligonucleotide microarrays: System establishment and expression profiling in human tissues. Genome Res. Dec. 2004;14(12):2486-94.

Bezrukov et al., Counting polymers moving through a single ion channel. Nature. 994;370:279-281.

Burghardt et al., In situ single-molecule imaging with attoliter detection using objective total internal reflection confocal microscopy. Biochemistry. Apr. 4, 2006;45(13):4058-68. Abstract Only.

Burns et al., An integrated nanoliter DNA analysis device. Science. Oct. 16, 1998;282(5388):484-7. Abstract Only.

Bustamante et al., Direct observation and manipulation of single DNA molecules using fluorecence microscopy. Annu Rev Biophys Chem. 1991;20:415-46.

Chan et al., DNA mapping technology based on microfluidic stretching and single-molecule detection of motif tags. Biophys J. 2003;84:302A. Poster 1470. Board #B725.

Chen et al., Single-Molecule Detection in Capillary Electrophoresis: Molecular Shot Noise as a Fundamental Limit to Chemical Analysis. Anal. Chem. Feb. 15, 1996;68(4):690-6.

Elson et al., Flourescence correlation spectroscopy. I. Conceptual basis and theory. Biopolymers. 1974;13(1):1-27. Abstract Only.

Foldes-Papp et al., Fluorescently labeled model DNAsequences for exonucleolytic sequencing. J Biotechnol. Apr. 13, 2001:86(3):181-201.

Foquet et al., DNA fragment sizing by single molecule detection in submicrometer-sized closed fluidic channels. Anal Chem. Mar. 15, 2002;74(6):1415-22. Abstract only.

Gratton et al., A continuously variable frequency cross-correlation phase fluorometer with picosecond resolution. Biophys J. Dec. 1983;44(3):315-24.

Grimm et al., Mapping of microsatellite markers developed from a flow-sorted swine chromosome 6 library. Mamm Genome. 1997;8(3):193-199. Abstract Only.

Guckenberger et al., Scanning tunneling, Icroscopy of insulators and biological specimens based on lateral conductivity of ultrathin water films. Science Dec. 2, 1994;266(5190):1538-40. Abstract Only.

Gurrueri et al., Imaging of kinked configurations of DNA molecules undergoing orthogonal field alternating gel electrophoresis by fluorescence microscopy. Biochem. 1990;29:3396-3401.

Ha et al., Initiation and re-initiation of DNA unwinding by the *Escherichia coli* Rep helicase. Nature. Oct. 10, 2002;419:638-641.

He et al., DNA sequencing by capillary electrophoresis with four-decay fluorescence detection. Anal Chem. 2000;72(24):5865-5873. Abstract Only.

Iannnone et al., Multiplexed single nucleotide polymorphism genotyping by oligonucleotide ligation and flow cytometry. Cytometry. 2000;39(2):131-140. Abstract Only.

Jamison et al., ComboScreen facilities the multiplex hybridization-based screening of high density clone arrays. Bioinformatics. 2000;16(8):678-684. Abstract Only.

Kasianowicz et al., Characterization of individual polynucleotide molecules using a membrane channel. Proc Natl Acad Sci USA. 1996;93:13770-13773.

Keller et al., Analytical applications of single-molecule detection. Anal Chem. Jun. 1, 2002;74(11):316A-324A. Abstract Only.

Landegren et al., Reading bits of genetic information: methods for single-nucleotide polymorphism analysis. Gen Res. 1998;8:769-776.

Larson et al., Single DNA molecule stretching in sudden mixed shear and elongational microflows. Lab Chip. 2006;6(9):1187-1199. Abstract Only.

Li et al., Flourescence studies of single biomolecules. Biochem Soc Trans. Nov. 2004;32(Pt 5):753-6.

Magde et al., Fluorescence correlation spectroscopy. Biopolymers. 2004;13(1):29-61. Abstract Only.

Masuko et al., Optimization of excimer-forming two-probe nucleic acid hybridization method with pyrene as a fluorophore. Nucl Acids Res. 1998;26(23):5409-5416.

Matsumoto et al., Light Microscopic Structure of DNA in solution studied by the 4', 6-diamidino-2-phenylindole staining method. Dept of Biophys, Faculty of Science, Kyoto University, Kyoto 606, Japan, pp. 501-516, 1981.

McBride et al., Multipplexed liquid arrays for simultaneous detection of stimulants of biological warfare agents. Anal Chem. Apr. 15, 2003;75(8):1924-30. Abstract Only.

Meng et al., Optical mapping of lambda bacteriophage clones using restriction endonucleases. Nat Genetics 1995;9:432-438.

Neumann et al., Capillary array scanner for time-resolved detection and identification of fluorescently labelled DNA fragments. J of Chromatography. 2000;871:299-310.

Niesner et al., Quantitative determination of the single-molecule detection regime in flourescence fluctuation microscopy by means of photon counting histogram analysis. J Chem Phys. Apr. 7, 2006;124(13):134704. Abstract Only.

Phillips et al., Application of single molecule technology to rapidly map long DNA and study the conformation of stretched DNA. Nuc Acids res. 2005;33(18):5829-5837.

Sase et al., Real time imaging of single fluorophores on moving actin with an epifluorescence microscope. Biophys J. Aug. 1995;69(2):323-8. Abstract Only.

Sauer et al., Single molecule DNA sequencing in submicrometer channels: state of the art and future prospects. J of Biotech. 2001;86:181-201.

Schafer et al., Single molecule DNA restriction analysis in the light microscope. Single Mol 2000;1:33-40.

Soper et al., Single-molecule spectroscopy in solution. Los Alamos Sci. 1992;20:286-296.

Wabuyele et al., Single molecule detection of double-stranded DNA in poly(methylmethacrylate) and polycarbonate microfluidic devices. Electrophoresis. Oct. 2001;22(18):3939-3948. Abstract Only.

Weiss et al., Flourescence spectroscopy of single biomolecules. Science. Mar. 12, 1999;283(5408):1676-83. Abstract Only.

Widengren et al., Single-molecule detection and identification of multiple species by multiparameter fluorescence detection. Anal Chem. Mar. 15, 2006;78(6):2039-2050. Abstract Only.

Winkler et al., Confocal fluorescence coincidence analysis: an approach to ultra high-throughput screening. Proc Natl Acad Sci USA. Feb. 16, 1999;96(4):1375-8.

Wittwer et al., Continuous fluorescence monitoring of rapid cycle DNA amplification. Biotechniques. Jan. 1997;22(1):130-138.

Xie et al., Optical studies of single molecules at room temperature. Annu Rev Phys Chem. 1998;49:441-80. Abstract Only.

Zhang et al., Homogenous rapid detection of nucleic acids using two-color quantum dots. Analyst. Apr. 2006;131(4):484-8. Epub Jan. 13, 2006.

Zhang et al., Bioinfomatics, 19(1):14-21, 2003.

* cited by examiner

FLUORESCENT NUCLEOTIDE INCORPORATION
WITH POLYMERASE INCORPORATION.

(RELATIVE
INTENSITY REFERENCE
TO STANDARD)

spFRET-BASED ASSAY WITH COMBINATION
OF SINGLE-BASE EXTENSION REACTION

TWO-COLOR DETECTION ASSAY IN COMBINATION WITH PRIMER EXTENSION

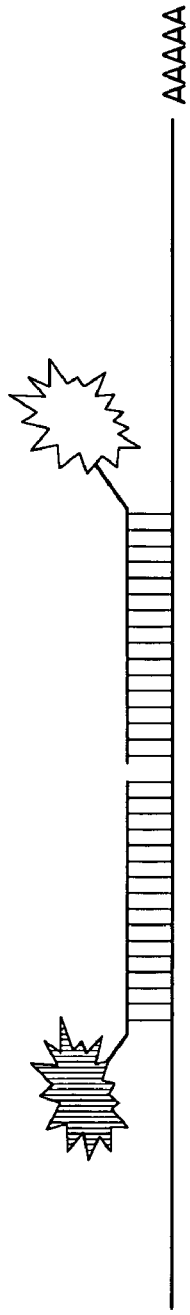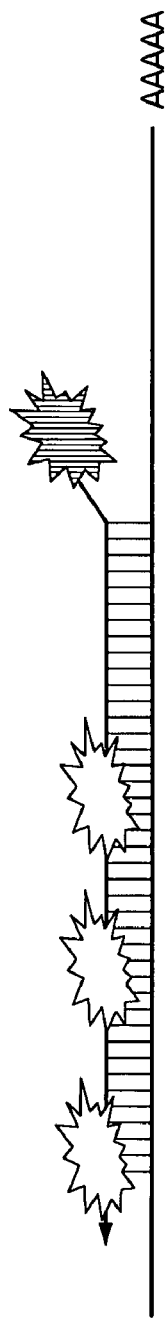
Fig. 30

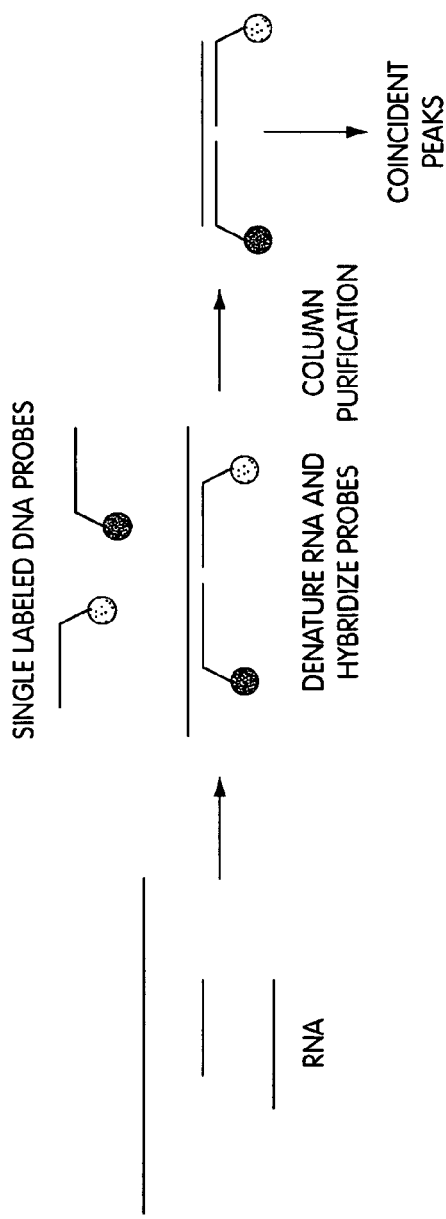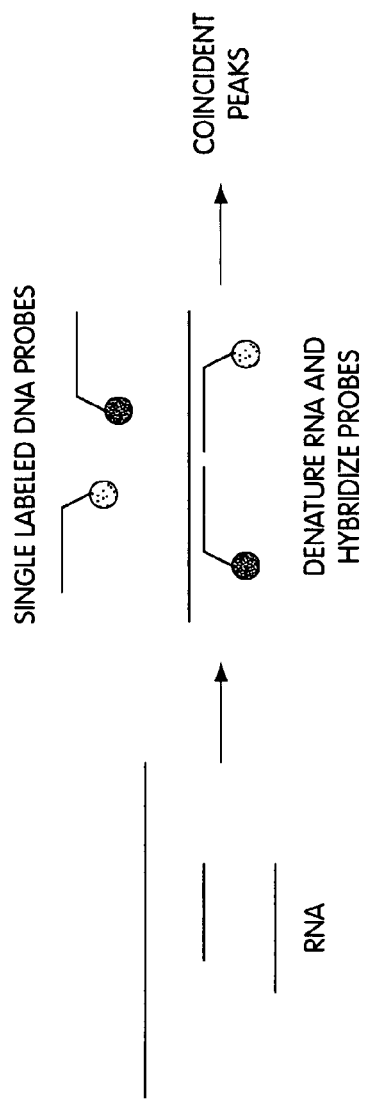

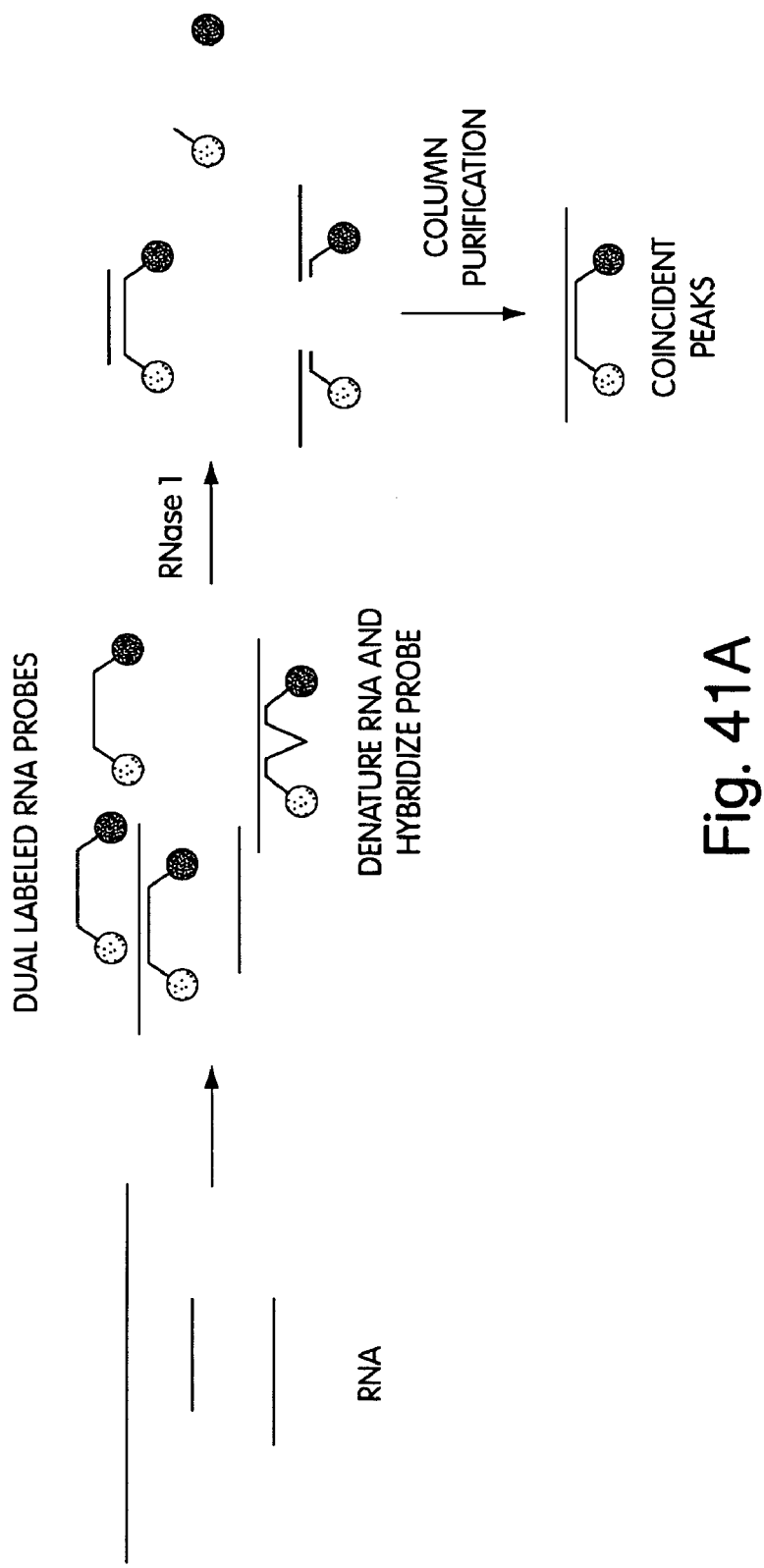

METHODS AND APPARATI USING SINGLE POLYMER ANALYSIS

RELATED APPLICATIONS

This application claims priority to U.S. Provisional Application having Ser. No. 60/383,968, filed on May 28, 2002, and entitled "METHODS AND APPARATI USING SINGLE POLYMER ANALYSIS", and U.S. Provisional Applications having Ser. Nos. 60/437,892, 60/441,334 and 60/441,337, filed Jan. 3, 2003, Jan. 20, 2003 and Jan. 21, 2003, respectively, and entitled "ACCURATE AND SENSITIVE DIRECT mRNA QUANTIFICATION FROM TOTAL RNA SAMPLES BY SINGLE MOLECULE COUNTING", the entire contents of all of which are herein incorporated by reference.

FIELD OF THE INVENTION

The invention relates to methods and apparati for analyzing single polymers such as single nucleic acid molecules.

BACKGROUND OF THE INVENTION

The polymerase chain reaction, cloning, and other amplification methods have been the cornerstones of genetic analysis. Technologies that are deriving from these methods have led to the genomics revolution that we see today. The sequencing of the human genome published in 2001 has been made possible because of the ability to clone and amplify DNA. Likewise, there are many other methods of analyzing DNA that are dependent on these technologies.

Single molecule detection, as defined in this application, is the detection of one fluorophore or one molecule. Single molecule detection has only been recently possible through the use of advanced optical detection methods. These methods include CCD fluorescence detection such as by Sase et al., 1995. Other methods that have achieved single molecule sensitivity include fluorescence correlation spectroscopy (Eigen and Rigler, 1994; Kinjo and Rigler, 1995), far-field confocal microscopy (Nie et al., 1994), cryogenic fluorescence spectroscopy (Kartha et al., 19995), single molecule photon burst counting (Haab and Mathies, 1995; Castro and Shera, 1995), two-photon excited fluorescence (Mertz, 1995), and electrochemical detection (Fan and Bard, 1995). These methods have not been applied extensively to the study of genetics because of difficulty in their implementation. Accordingly, most of these detection methodologies have not gained the attention of geneticists and molecular biologists.

SUMMARY OF THE INVENTION

The merging of single molecule detection and analysis and tagging chemistries that offer unique advantages in a single molecule detection setting is a breakthrough for molecular biology and genetic analysis. To this end, the invention relates to methods that exploit the ability to detect and thus analyze single molecules such as single nucleic acid molecules. Often times in molecular biology, it is necessary to amplify molecules such as nucleic acid molecules in order to conduct any analysis. That is because until recently most hardware used for genetic analysis was not capable of detecting single molecules. With the advent of detection systems with increased sensitivity, it is now possible to study molecules without prior amplification. This new approach is advantageous since the amplification process is known to introduce artifacts (e.g., sequence errors) into the amplified product that were not present in the parent molecule. Using prior art methods that included an amplification step, the information derived from an amplified product may be an amplification artifact rather than an inherent feature of the parent molecule, and in most instances it is difficult to distinguish between these two.

The analyses described herein can be performed using single molecule detection and analysis systems. One such system is the Gene Engine™ which has been described in greater detail in published PCT Patent Applications WO98/35012, WO00/09757 and WO01/13088, published on Aug. 13, 1998, Feb. 24, 2000 and Feb. 22, 2001 respectively, and in U.S. Pat. No. 6,355,420 B1 issued on Mar. 12, 2002, the entire contents of which are incorporated herein.

Accordingly, the invention provides in one aspect a method for analyzing a single nucleic acid molecule comprising exposing a single nucleic acid molecule to at least two distinguishable detectable labels for a time sufficient to allow the detectable labels to bind to the single nucleic acid molecule, and analyzing the single nucleic acid molecule for a coincident event using a single molecule detection system, wherein the coincident event indicates that the at least two distinguishable detectable labels are bound to the single nucleic acid molecule.

The single nucleic acid molecule may be a DNA molecule or an RNA molecule, although it is not so limited. Preferably, it is denatured to a single stranded form in order to facilitate hybridization with a unit specific marker, or a primer, or a newly synthesized nucleic acid molecule, as the case may be. Although the single nucleic acid molecule may be linearized or stretched prior to analysis, this is not necessary as the single molecule detection system is capable of analyzing both stretched and compacted nucleic acids. This is particularly the case when coincident events are detected since these events simply require the presence or absence of at least two labels, but are not necessarily dependent upon the relative positioning of the labels (provided they are sufficient proximal to each other in some instances to enable energy transfer from one label to another).

The distinguishable detectable labels may be present on different unit specific markers (i.e., a dual labeled probe) or on the same unit specific marker (i.e., a singly labeled probe). The at least two distinguishable detectable labels encompass two, three, four, five, or more labels. In some important embodiments, only two labels are required.

The method may further comprise exposing the single nucleic acid molecule to a third detectable label that binds specifically to a mismatch between the single nucleic acid molecule and a unit specific marker, and wherein a coincident event between the first, second and third detectable labels is indicative of the mismatch. In this case, the coincident event encompasses the presence of first, second and third detectable labels on the hybrid formed by the single nucleic acid molecule and a unit specific marker.

The method may further comprise exposing the single nucleic acid molecule and detectable labels to a chemical or enzymatic single stranded cleavage reaction prior to analyzing the single nucleic acid molecule. In these embodiments, the cleavage reaction can accomplish several things including but not limited to cleaving the single nucleic acid molecule and the unit specific marker at the location of a mismatch, digesting the unbound probes whether they be DNA or RNA in nature, and digesting single nucleic acid molecules that did not hybridize to a probe. Chemical and enzymatic cleavage methods are known in the art. For instance, the enzymatic single stranded cleavage reaction may use a single stranded RNA nuclease, a single stranded DNA nuclease, or a combination thereof. Various single stranded RNA nucleases are known in the art including but not limited to RNase I. Similarly, various single stranded DNA nuclease are known in the art including but not limited to S1 nuclease.

In some embodiments, the hybridization and/or reaction mixture is cleaned prior to analyzing the single nucleic acid molecule. As used herein "cleaning" refers to the process of removing one or more of the following: unbound probes, unhybridized nucleic acid molecules, unbound or unincorporated labels (such as unincorporated nucleotides), and cleaved products following exposure to a chemical or enzymatic cleavage reaction. This cleaning step can be accomplished in a number of ways including but not limited to column purification. Column purification generally involves capture of small molecules within a column with flow-through of larger molecules (such as the target hybridized nucleic acid molecules). In other embodiments, a cleavage reaction and a column purification are used in combination to remove unwanted molecules. It is to be understood however that the method can be performed without removal of these molecules prior to analysis, particularly since coincident detection can distinguish between desired hybridization events and artifacts. Thus, in some embodiment, the unbound detectable labels are not removed prior to analysis using the single molecule detection system.

The method preferably reads out a coincident event. The coincident event may take many forms including but not limited to a color coincident event. It can also be a binding coincident event, in which the binding of two unit specific markers is determined. It can further be the coincident existence of two or more detectable labels on a target molecule (including but not limited to the existence of a donor FRET fluorophore and an acceptor FRET fluorophore). The coincident event may also be the proximal binding of a first detectable label that is a donor FRET fluorophore and a second detectable label that is an acceptor FRET fluorophore. In this latter embodiment, a positive signal is a signal from the acceptor FRET fluorophore upon laser excitation of the donor FRET fluorophore. This latter embodiment requires a single molecule detection and analysis system that comprises one detector and one laser since a positive signal from the FRET pair is generate by only one laser and is emission from only one fluorophore.

In certain embodiments, the method involves the use of at least one unit specific marker to which is attached one of the distinguishable detectable labels. In these and other embodiments, the method may further comprise exposing the single nucleic acid molecule to the labeled unit specific marker in the presence of a polymerase and labeled nucleotides. Preferably, the unit specific marker and nucleotides are differentially labeled. In this case, it is possible to synthesize a new nucleic acid molecule extending from the unit specific marker (i.e., the unit specific marker acts as a primer for the newly synthesize nucleic acid molecule). The newly synthesized nucleic acid molecules is therefore complementary to the single nucleic acid molecule which acts as a template for the newly synthesized strand. In these embodiments, the detectable labels are incorporated into the newly synthesized strand.

The method can be further used to determine the length of the single nucleic acid molecule based on the signal intensity emitted by the newly synthesized strand. In these embodiments, the method is a method of determining integrity of a nucleic acid sample (such as an RNA sample) from which the single nucleic acid molecule derived. That is, it can be used to determine the level of degradation in, for example, the RNA sample as a propensity of short RNA molecule is indicative of degradation of the sample, while long RNA molecules are not. The method therefore may involve determining the signal intensity from the hybrid of the single nucleic acid molecule and the newly synthesized nucleic acid molecule (or alternatively of the newly synthesized nucleic acid molecule alone) as a measure of the length of the newly synthesized nucleic acid molecule (and thus of the template single nucleic acid molecule). The signal intensity is proportional to the length, therefore a greater intensity will indicate longer single nucleic acid molecules while lower intensity will indicate short and thus degraded single nucleic acid molecules.

In some embodiments, the unit specific marker and nucleotides are labeled with a FRET fluorophore pair. In embodiments which involve hybridization of two unit specific markers, then they can similarly be labeled with corresponding FRET fluorophores. That is, one unit specific marker is labeled with a donor FRET fluorophore and the other is labeled with an acceptor FRET fluorophore. Alternatively, the unit specific marker is labeled with either a donor or an acceptor fluorophore and the nucleotides are labeled with an acceptor or a donor fluorophore respectively.

In another embodiment, one detectable label is attached to a unit specific marker and is a first FRET fluorophore, and the other detectable label is incorporated into a newly synthesized nucleic acid molecule hybridized to the single nucleic acid molecule and is the donor or acceptor of the first FRET fluorophore. That is, if the first FRET fluorophore is a donor fluorophore, then the newly synthesize nucleic acid molecule has incorporated into it an acceptor fluorophore, and vice versa.

The choice of polymerase will depend upon the nature of the template and the newly synthesized nucleic acid molecule. In one embodiment, the polymerase is a DNA polymerase. In another embodiment, the polymerase is a reverse transcriptase.

In important embodiments, the single nucleic acid molecule is present in a nanoliter volume. That is, it is only necessary to load a nanoliter volume into the single molecule detection and analysis system. In still other important embodiments, the single nucleic acid molecule is present at a frequency of 1 in 1,000,000 molecules or 1 in 2,000,000 molecules in a nucleic acid sample (such as an RNA sample). Accordingly, the method can be used to detect and analyze nucleic acid molecules that are extremely rare.

In important embodiments, the detectable labels are present on a unit specific marker that is a DNA, RNA, PNA, LNA or a combination thereof. In this and other aspects of the invention, RNAi molecules can be similarly used. In other embodiments, the detectable labels are provided as molecular beacon probes. The detectable label may also be attached to a nucleic acid molecule hybridized to a universal linker attached to a unit specific marker.

In still other embodiment, the method further comprises exposing the nucleic acid molecule to a ligase prior to analysis using the single molecule detection system.

In another aspect, the invention provides a composition comprising a unit specific marker attached to a universal linker that is hybridized to a complementary nucleotide sequence attached to a detectable label.

In another aspect, the invention provides a method for characterizing a polymer. The method comprises contacting the polymer with a plurality of unit specific markers, each of the plurality having a unique and distinct label. When bound to the polymer, individual unit specific markers are spaced apart on the polymer such that, if the labels were not distinct from each other, they would be separated by a distance less than the detection resolution of the detection system.

In one embodiment, the polymer is a nucleic acid molecule, and the nucleic acid molecule may be a DNA or an RNA. In preferred embodiments, the nucleic acid molecule is harvested from a natural source such as a cell, a population of cells, or a tissue.

The nucleic acid molecule may be free-flowing, or it may be fixed to a solid support during the characterization.

In some embodiments, the nucleic acid is capable of being imaged directly (i.e., it has bound to it via the unit specific markers a directly detectable label such as a fluorophore or a radioactive compound). In other embodiments, the nucleic acid is imaged indirectly (i.e., it has bound to it via the unit specific markers a label that is indirectly detectable (i.e., an enzyme that converts a substrate into a visible product, or a biotin molecule that is bound by a directly labeled avidin molecule, or a primary antibody that is recognized by a secondary antibody or a hapten that is itself directly labeled).

As another example, in one embodiment, the unique and distinct labels are substrates for an enzymatic reaction. In one embodiment, the enzymatic reaction is selected from the group consisting of a primer extension reaction and a ligase-mediated reaction. In a related embodiment, the enzymatic reaction produces a detectable product, and preferably the detectable product is not itself amplified. In one embodiment, the presence of a detectable product indicates a pattern of binding of unit specific markers to the polymer. For example, the presence of two unit specific markers within a short distance of each other may facilitate the synthesis of a new nucleic acid molecule which can be detected.

In another embodiment, the unique and distinct labels are differential intensity fluorescent tags.

In important embodiments, the polymer is not pre-amplified. If the polymer is a nucleic acid molecule, it may be single stranded or it may be double stranded. In a related embodiment, the polymer is a nucleic acid molecule that is denatured to a single-stranded form.

In addition to labeling the unit specific markers, the polymer may also be labeled with a backbone specific label.

In another aspect, the invention provides a method for characterizing a polymer, comprising fixing the polymer to a solid support, contacting the polymer with a plurality of unit specific markers, each of the plurality having a unique and distinct label, and determining a pattern of binding of the plurality of unit specific markers to the polymer. Again, when bound to the polymer, individual unit specific markers are spaced apart on the polymer such that, if the labels were not distinct from each other, they would be separated by a distance less than the detection resolution.

Many of the embodiments recited above for the first aspect of the invention are applicable to this and other aspects of the invention and thus will not be recited again.

In on embodiment, the polymer is fixed to the solid support in a random orientation. In another embodiment, the polymer is fixed to the solid support in a non-continuous manner.

The method can be used to characterize the polymer in terms of the presence of single nucleotide polymorphisms, microsatellites, insertions, deletions, and the like.

In yet a further aspect, the invention provides a method for characterizing a polymer comprising contacting the polymer with a plurality of unit specific markers, each of the plurality having a label, and measuring the distance between consecutive unit specific markers bound to a polymer. The distance between the consecutive unit specific markers is indicative of a particular haplotype of polymer.

In one embodiment, each of the plurality of unit specific markers is labeled with an identical label, while in other embodiments, each of the plurality is labeled with a different label. As above, the labels may be differential intensity fluorescent labels.

In yet another aspect, the invention provides a method for characterizing a polymer comprising attaching a plurality of unit specific markers in a spatially defined manner to an array on a solid support, contacting the plurality of unit specific markers with an unamplified polymer, and determining a pattern of binding of the unamplified polymer to the plurality of unit specific markers.

In one embodiment, the pattern of binding of the unamplified polymer to the plurality of unit specific markers indicates a haplotype. The haplotype is based on information from a plurality of genetic loci.

In another embodiment, each spatially defined position in the array is occupied by a haplotype specific unit specific marker, and that haplotype may derive from a single genetic locus or from a plurality of loci.

In still another embodiment, the specific unit specific marker is specific for a polymorphism. The polymorphism may be selected from the group consisting of a single nucleotide polymorphism, a deletion, an insertion, a translocation, a duplication, a genomic amplification, but is not so limited.

In one embodiment, the polymer is derived from a single somatic cell hybrid. In another embodiment, the polymer is a homogenous sample of one chromosome allele. In yet another embodiment, each spatially defined position in the array is occupied by an allele specific unit specific marker.

In a further aspect, the invention provides a method for determining the haplotype of a nucleic acid sample comprising amplifying nucleic acid molecules in a nucleic acid sample using an allele-specific polymerase chain reaction (PCR) and a set of four primers, and analyzing the amplified nucleic acid molecules using a Gene Engine™ system. Each primer in the set of four primers is unique at its 3' end and is labeled with a unique detectable label.

In one embodiment, the nucleic acid sample is in solution.

In yet another aspect, the invention provides a method for determining a length of a nucleic acid molecule comprising labeling a nucleic acid molecule with a detectable label, and analyzing the labeled nucleic acid molecule using a Gene Engine™ system. The Gene Engine™ system comprises a narrow channel positioned within an excitation beam, and the labeled nucleic acid molecule is passed through multiple confocal spots and an average intensity of the labeled nucleic acid passing through the multiple confocal spots is determined.

In another aspect, the invention provides a method for determining a length of a nucleic acid molecule comprising labeling a nucleic acid molecule with a detectable label, and analyzing the labeled nucleic acid molecule using a Gene Engine™ system. The Gene Engine™ system comprises an excitation volume to diffraction spot ratio of greater than 10, and the labeled nucleic acid molecule is passed through a diffraction spot and an integrated intensity of the labeled nucleic acid passing through the diffraction spot is determined.

In one aspect, the invention provides a method for determining a length of a nucleic acid molecule comprising labeling a nucleic acid molecule with a detectable label, and analyzing the labeled nucleic acid molecule using a Gene Engine™ system. The labeled nucleic acid molecule is imaged using a uniform illumination source, and an integrated intensity of the labeled nucleic acid passing through the diffraction spot is determined.

In several of the foregoing aspect, the methods further comprise determining a velocity of the labeled nucleic acid passing through the Gene Engine™ system. In some embodiments, the velocity of the labeled nucleic acid is determined using multiple confocal illumination spots.

In other embodiments, the detectable label is covalently conjugated to the nucleic acid molecule. The detectable label may be a fluorophore, but it is not so limited. In another embodiment, the nucleic acid molecule is uniformly labeled along its length.

In another aspect, the invention provides another method for determining a length of a nucleic acid molecule comprising contacting a nucleic acid sample with a first and a second unit specific marker of known sequences and having a first and a second detectable label respectively, allowing the first and second unit specific markers to hybridize to a complementary nucleotide sequence in the nucleic acid molecule and determining the distance between the location of the first and second unit specific markers once bound to the nucleic acid molecule.

In another aspect, the invention provides a method for determining the gene profile of a single cell. The method comprises contacting a unit specific marker with an unamplified nucleic acid sample from one cell, and determining the binding of the unit specific marker to the nucleic acid sample using a Gene Engine™ system. The binding of the unit specific marker to the nucleic acid sample indicates that the cell contains a specific nucleic acid molecule. In one embodiment, the nucleic acid sample is an RNA sample. In another embodiment, the nucleic acid sample is a cDNA sample. In still another embodiment, the nucleic acid sample is a genomic DNA sample.

The single cell may be a rare cell such as a stem cell or a precursor cell. The cell may be selected from the group consisting of hemopoietic cells, neural cells, liver cells, skin cells, cord blood cells, but it is not so limited. In other embodiments, the cell may be a cancer cell or be suspected of being a cancer cell. The cell may be an acute leukemia cells, a Reed Sternberg cells, and the like.

The nucleic acid sample may also be a forensic sample. In other embodiment, the cell is an embryo cells.

In one embodiment, the unit specific marker is specific for a genetic abnormality. In another embodiment, the unit specific marker binds to a known nucleic acid molecule. In another embodiment, the unit specific marker is a plurality of unit specific markers.

In another embodiment, determining the binding of the unit specific marker to the nucleic acid sample comprises determining a pattern of binding of the unit specific marker to the nucleic acid sample. The method can further comprise comparing the pattern of binding of the unit specific marker to a second binding pattern. The second binding pattern may be that of a different cell, it may be that of a non-cancerous cell, or it may be that of a differentiated cell.

The unit specific marker may be conjugated to a detectable label, which in turn may be selected from the group consisting of differential intensity fluorophores, differential lifetime fluorophores, and fluorescence resonance energy transfer (FRET) fluorophores.

In one embodiment, the binding of the unit specific marker to the nucleic acid sample is determined by imaging. In another embodiment, it may be determined by confocal detection.

In yet a further aspect, the invention provides a method for quantitating a nucleic acid molecule in a cell comprising contacting a unit specific marker with an unamplified nucleic acid sample from one or more cells, and measuring the level of binding of the unit specific marker to the nucleic acid sample using a Gene Engine™ system. The unit specific marker is conjugated to a detectable label, and the level of binding of the unit specific marker to the nucleic acid sample is indicative of the amount of the nucleic acid molecule in the sample.

In still another embodiment, the invention provides a method for determining the presence of a polymorphism in a nucleic acid molecule comprising allowing a wild type unit specific marker of a specified length to hybridize to a nucleic acid molecule in a nucleic acid sample from one or more cells, then exposing the nucleic acid sample, after hybridization and washing, to an enzymatic or chemical reaction in order to cleave a heteroduplex at a single stranded region, and detecting one or more cleavage products of the enzymatic or chemical reaction using a Gene Engine™ system. The wild type unit specific marker is labeled at one or both ends with a first detectable label, the nucleic acid molecule in the nucleic acid sample is labeled at one or both ends with a second detectable label that is distinct from the first detectable label, and a double stranded cleavage product having both first and second detectable labels and a length of less than the specified length of the wild type unit specific marker is indicative of a polymorphism in the nucleic acid molecule from the nucleic acid sample.

In one embodiment, the nucleic acid sample is an amplified sample and the method detects errors in an amplification process. In another embodiment, the second detectable label is incorporated into the nucleic acid molecule during the amplification process. The nucleic acid may be RNA or DNA.

In one embodiment, the enzymatic reaction is a reaction with an enzyme selected from the group consisting of endonuclease VII, RNase, and the like. In another embodiment, the chemical reaction comprises reaction with osmodium tetroxide.

In one embodiment, the wild type unit specific marker is labeled at its 3' end and the nucleic acid molecule is labeled at its 5' end. In another embodiment, the wild type unit specific marker is labeled at its 5' end and the nucleic acid molecule is labeled at its 3' end. In still another embodiment, the wild type unit specific marker and the nucleic acid molecule are both labeled at their 3' and 5' ends.

In one embodiment, the detection of the cleavage products is not dependent upon amplification of the cleavage products.

In one aspect, the invention provides another method for determining the presence of a polymorphism in a nucleic acid molecule comprising amplifying one or more nucleic acid molecules using a first and a second primer to form an amplified nucleic acid sample having amplified nucleic acid molecules of a defined length, denaturing and re-hybridizing the amplified nucleic acid sample, and then exposing the re-hybridized, amplified nucleic acid sample to an enzymatic or chemical reaction in order to cleave a heteroduplex at a single stranded region, and detecting one or more cleavage products of the enzymatic or chemical reaction using a Gene Engine™ system. The first primer is labeled with a first detectable label, and the second primer is labeled with a second detectable label distinct from the first detectable label, and a double stranded cleavage product comprising either the first or the second detectable label and a length of less than the defined length of the amplified nucleic acid molecules is indicative of a polymorphism in an amplified nucleic acid molecule from the amplified nucleic acid sample.

In one embodiment, the re-hybridized, amplified nucleic acid sample is fixed to a solid support prior to the enzymatic or chemical reaction at either or both ends. In another embodiment, the double stranded cleavage product is fixed on a solid support and imaged.

The invention further provides a method for identifying the source of a nucleic acid molecule comprising digesting a nucleic acid molecule with a first and a second restriction endonuclease to form nucleic acid fragments, labeling a first end of a nucleic acid fragment with a first detectable label, and labeling a second end of the nucleic acid fragment with a second detectable label that is distinct from the first detectable label to form an end-labeled nucleic acid fragment, analyzing the end-labeled nucleic acid fragment using a Gene Engine™ system to detect the first and second detectable label, and determine a length of an end-labeled nucleic acid fragment by measuring a distance between the first and the second detectable labels for each end-labeled nucleic acid fragment. Prior to labeling, the first end and the second end of the nucleic acid fragment are different, and a plurality of lengths of a plurality of end-labeled nucleic acid fragments identifies the source of a nucleic acid molecule.

In one embodiment, the first end and the second end of the nucleic acid fragment are selected from the group consisting of a 3' overhang, a 5' overhang, and a blunt end. In another embodiment, the first and second detectable labels are conjugated to the nucleic acid fragments indirectly. In yet another embodiment, the first and second detectable labels are conjugated to the nucleic acid fragments using a polymerase reaction. In still another embodiment, the polymerase reaction comprises an additional primer.

In one embodiment, one or both the first and second restriction endonucleases are chimeric.

In one embodiment, the nucleic acid molecule is unamplified.

In another embodiment, the nucleic acid molecule is a bacterial artificial chromosome (BAC). In yet another embodiment, the nucleic acid molecule is a yeast artificial chromosome (YAC). In still another embodiment, the acid molecule is from a forensic sample. In another embodiment, the nucleic acid molecule is from a sample intended for paternity determination.

The nucleic acid molecule and/or the nucleic acid fragment may be labeled with a backbone label that is sequence independent.

In still another embodiment, the invention provides a method for identifying the source of a nucleic acid molecule comprising digesting a nucleic acid molecule with a first restriction endonuclease to form nucleic acid fragments, labeling nucleic acid fragments with a non-specific backbone label, analyzing the labeled nucleic acid fragments using a Gene Engine™ system, and determining a length of the labeled nucleic acid fragment by measuring a time between the first detected non-specific backbone label and the last detected non-specific backbone label for each end-labeled nucleic acid fragment. Prior to labeling the first end and the second end of the nucleic acid fragment are different, and a plurality of lengths of a plurality of end-labeled nucleic acid fragments identifies the source of a nucleic acid molecule.

In one embodiment, the first end and the second end of the nucleic acid fragment are selected from the group consisting of a 3' overhang, a 5' overhang, and a blunt end.

These and other aspects and embodiments of the invention will be discussed in greater detail herein.

BRIEF DESCRIPTION OF THE DRAWINGS

FIG. 30 is a schematic showing the dual probe hybridization assay and the probe extension assay. In the dual probe hybridization assay the target molecule is hybridized to two probes ranging from 20–30 nucleotides in length, for example, each of which is labeled with a distinct detectable label from the other. In the probe extension assay, a labeled (e.g., with Cy5) primer is hybridized to the target molecule and extended by reverse transcription thereby incorporating labeled nucleotides (e.g., TAMRA labeled nucleotides).

FIG. 39A is a schematic of a dual probe hybridization assay including a column purification step.

FIG. 39B is a schematic of a dual probe hybridization assay excluding a column purification step.

FIG. 41A is a schematic of a dual labeled RNA probe hybridization assay including an RNase I reaction and a column purification step.

DETAILED DESCRIPTION OF THE INVENTION

Figure 1:
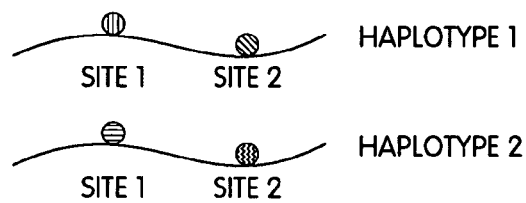
FIG. 1 is a schematic of the labeling of two nucleotide sequences to determine and distinguish between haplotypes.

The invention provides methods of analyzing nucleic acid molecules such as DNA and RNA through unique tagging methods that are made possible by the advent of single molecule detection systems. Recently, the study of genomics has been limited to the use of existing technologies that rely on the amplification of DNA through PCR or cloning.

Amplification and cloning techniques are commonly used in genetic analysis methods used to date. In recent years, however, single molecule detection methodologies have been developed that allow genetic analysis without the need for cloning or amplification. These single molecule detection technologies allow for direct analysis of nucleic acid molecules.

The invention provides means of chemically and enzymatically modifying nucleic acid molecules followed by their direct analysis using single molecule detection and analysis systems such as the Gene Engine™ described in published PCT Patent Applications WO98/35012, WO00/09757 and WO01/13088, published on Aug. 13, 1998, Feb. 24, 2000 and Feb. 22, 2001 respectively, and in U.S. Pat. No. 6,355,420 B1 issued on Mar. 12, 2002. As used herein, the terms "single molecule detection system" and "single molecule detection and analysis system" are used interchangeably. The combination of these new tagging approaches combined with single molecule detection results in new and powerful methods to study different properties of nucleic acid molecules.

The methods provided herein are not dependent upon stretching of the polymer being analyzed. This is because of the methods provided herein rely on coincident detection of labels (e.g., fluorophores) on a nucleic acid molecule. Coincident detection of labels means that two or more labels are detected in close proximity to each other. In some embodiments, the labels are detected simultaneously with their emission spectra overlapping substantially or completely. Coincident detection is unlikely to occur between two or more nucleic acid molecules that are each labeled with only one label or between two or more free (i.e., unbound) labels. One advantage of using coincident detection as an indication of a nucleic acid molecule of interest is that such an approach does not require removal of free labels from the nucleic acid sample prior to analysis since single label detection events are disregarded.

As used herein, stretching of the target polymer means that the polymer is provided in a substantially linear form rather than a compacted and or folded form. A stretched polymer and a linearized polymer are used interchangeably. A linear form is more appropriate if the sequence of the polymer is of interest. Linearizing the polymer prior to analysis requires particular configurations of the single molecule detection system in order to maintain the linear form. This configurations are not required if the target polymer can be analyzed in a compacted form.

The methods of the invention can be used in the analysis of both DNA and RNA. DNA analysis includes determination of genetic variation, polymorphisms, mutations, DNA lengths, and DNA methylation/footprinting, among others. RNA analysis, like DNA analysis, can be accomplished without prior amplification. In addition, RNA does not have to be converted into DNA (e.g., cDNA) prior to analysis, nor does it have to be harvested in large amounts. This latter point is particularly important in the analysis of rare transcripts, or analysis of transcripts for rare or small cell populations. RNA analysis, according to the invention, includes determination of RNA quantity, splice variations, polymorphisms, and mutations, among others.

Accurate measurement of RNA levels in biological samples is very important for functional genomics studies and for developing better diagnostics. Current methods to quantitatively measure RNA are either tedious (e.g., Northern blot) or require amplification (e.g., RT-PCR) which can limit accuracy or reliability. The invention obviates these concerns by directly analyzing individual, unamplified RNA molecules, thereby permitting high sensitivity RNA quantitation. In a total RNA sample, individual mRNAs are directly labeled with unique probes (or as used herein "unit specific markers") such as gene-specific fluorescent probes. The sample is then introduced into a nanofluidic silicon chip and individual molecules are counted using a high sensitivity, multicolor fluorescence detection system.

Whether analysis is of DNA or RNA molecules, the invention provides a method for distinguishing between single molecules and unbound probes using a two-color coincident detection. This approach minimizes the non-specific background signals with 20–20,000 molecules typically being detected in just one minute. As a proof of principle, in vitro transcribed β-actin, E. coli spike 1 (750 bp), E. coli spike 8 (2 Kb) and lamin A/C RNA templates spiked into human RNA were used to demonstrate that single molecule counting methods can be performed simply, reproducibly, specifically, and with highly sensitivity (e.g., 1 copy mRNA molecule can be detected per 2 million total RNA molecules). This demonstrates that individual RNA molecules can be accurately and reproducibly detected in complex RNA samples. This sensitivity has been demonstrated through a wide linear dynamic range of detection ($>10^3$). The high sensitivity also means that individual genes can be detected using only picograms of total RNA. In addition, the method only requires a nanoliter detection volume, thereby providing enhanced sensitivity for very small samples.

The invention also provides assays to quantify poly(A)$^+$ RNA levels in total RNA samples and monitor mRNA integrity. Multicolor reactions and detection also allows different transcripts to be monitored quantitatively in the same assay. Splice variants can be detected and quantitated in this manner. The methods provided herein relating to RNA analysis are sometimes referred to as "DirectRNA™" technology. The assays relating to RNA analysis will be described in greater detail in the Examples.

The sensitivity of the methods and systems provided herein allows nucleic acid molecules to be analyzed individually. The invention is based in part on novel chemistries pertaining to single molecule detection that allow polymers such as nucleic acid molecules to be analyzed in terms of haplotyping, sequence detection, sizing, polymorphism/mutation detection, insertion/deletion analysis, and repeated structure analysis. Each of these applications will be discussed in greater detail below.

The invention relates in some embodiments to two general classes of linear analysis, namely fixed molecule and moving molecule linear analyses. Linear analysis of fixed molecules has been described in the art and includes methods of fluid-fixing linear molecules such as DNA to surfaces and using imaging or scanning-based approaches to collect sequence information. Linear analysis of moving molecules employing either flow or electrophoretic systems are described in PCT applications WO98/35012, WO00/09757 and WO01/13088, which were published on Aug. 13, 1998, Feb. 24, 2000 and Feb. 22, 2001, respectively, and U.S. Pat. No. 6,355,420 B1, issued on Mar. 12, 2002.

A "polymer" as used herein is a compound having a linear backbone to which monomers are linked together by linkages. The polymer is made up of a plurality of individual monomers. An individual monomer as used herein is the smallest building block that can be linked directly or indirectly to other building blocks or monomers to form a polymer. At a minimum, the polymer contains at least two linked monomers. The particular type of monomer will depend upon the type of polymer being analyzed. In preferred embodiments, the polymer is a nucleic acid molecule such as a DNA or RNA molecule. The invention is however not so limited and could be used to label and analyze non-nucleic acid polymers. With the advent of aptamer technology, it is possible to use nucleic acid based probes (i.e., unit specific markers) in order to recognize and bind a variety of compounds, including peptides and carbohydrates, in a structurally, and thus sequence, specific manner.

"Sequence-specific" when used in the context of a nucleic acid molecule means that the probe (or unit specific marker, as it is referred to herein interchangeably) recognizes a particular linear arrangement of nucleotides or derivatives thereof. When used in the context of a peptide, sequence-specific means the probe recognizes a particular linear arrangement of nucleotides or nucleosides or derivatives thereof, or amino acids or derivatives thereof including post-translational modifications such as glycosylations. When used in the context of a carbohydrate, sequence specific means the probe recognizes a particular linear arrangement of sugars.

The polymers to be analyzed are referred to herein as "target" molecules or polymers. In some important embodiments, the target molecules are DNA, or RNA, or amplification products or intermediates thereof, including complementary DNA (cDNA). In important embodiments, the nucleic acid molecules are RNA. When analyzed by various prior art methods, RNA is generally converted to DNA (e.g., cDNA) for purposes of stability and amplification, or alternatively very large amounts of RNA are required. Using the methods provided herein, it is possible to analyze RNA directly, without conversion to DNA, amplification, or the need for large quantities. Accordingly, there methods are most appropriate for (but not limited to) the analysis of rare RNA transcripts or RNA samples for rare cells or small tissue samples. The nucleic acid molecules may be single stranded and double stranded nucleic acids. DNA includes genomic DNA (such as nuclear DNA and mitochondrial DNA), as well as in some instances cDNA. In important embodiments, the nucleic acid molecule is a genomic nucleic acid molecule.

The nucleic acid molecules can be directly harvested and isolated from a biological sample (such as a tissue or a cell culture) without the need for prior amplification using techniques such as polymerase chain reaction (PCR). Harvest and isolation of nucleic acid molecules are routinely performed in the art and suitable methods can be found in standard molecular biology textbooks (e.g., such as Maniatis' Handbook of Molecular Biology).

In important embodiments of the invention, however, the nucleic acid molecule is a non in vitro amplified nucleic acid molecule. As used herein, a "non in vitro amplified nucleic acid molecule" refers to a nucleic acid molecule that has not been amplified in vitro using techniques such as polymerase chain reaction or recombinant DNA methods. A non in vitro amplified nucleic acid molecule may however be a nucleic acid molecule that is amplified in vivo (in the biological sample from which it was harvested) as a natural consequence of the development of the cells in vivo. This means that the non in vitro nucleic acid molecule may be one which is amplified in vivo as part of locus amplification, which is commonly observed in some cell types as a result of mutation or cancer development.

The methods provided herein are capable of generating signatures for each polymer based on the specific interactions between probes (i.e., unit specific markers) and target polymers. A signature is the signal pattern that arises along the length of a polymer as a result of the binding of unit specific markers (of different or identical sequence) to the polymer. The signature of the polymer uniquely identifies the polymer. The identity of the target polymer to which a probe binds need not be known prior to analysis, although for some applications, it will be known. This may be the case, for example, where a particular condition is diagnosed based on the presence or absence of a particular target nucleic acid, including a genomic DNA fragment or an RNA transcript.

The methods of the invention generally require exposing a target molecule to a probe, primer and the like. As used herein, this means that the target molecule is physically combined with the probe, primer and the like and these constituents are allowed to hybridize with each other provided they have complementary sequences. Target molecules can also be exposed to detectable labels that are incorporated into a newly synthesized nucleic acid molecule as a result of a primer extension assay.

Some methods of the invention embrace hybridization of dually or singly labeled probes to a target nucleic acid molecule. These hybridization events are performed under conditions known in the art to enhance hybrid formation between completely complementary sequences. Accordingly, under these conditions, regions of complementarity between the target and the probe will form hybrids while other regions will not (and thus will be single-stranded mismatch regions). As used herein, a mismatch refers to a region of a target and a probe that are not hybridized to each other due to lack of complementarity. Preferably, these mismatches are flanked on either side by regions of complementarity. The mismatch may be as short as one nucleotide, but clearly can encompass several nucleotides provided the remaining complementary regions can still hybridize to each other. Many of the methods provided herein seek to remove hybrids that contain mismatches as these hybrids would otherwise provide inaccurate information about the sequence of a target nucleic acid, for example. Mismatches (and the hybrids that contain them) can be eliminated by single stranded cleavage reactions. These reactions are known in the art and can include but are not limited to chemical and enzymatic cleavage reactions. Additionally, depending upon the nature of the target and the probe, the cleavage reactions can be structured to cleave single stranded RNA only, single stranded DNA only, or both single stranded RNA and DNA.

Although many of the methods described herein are based on coincident detection, it may still be desirable to remove as many singly labeled molecules from a sample prior to analysis using the single molecule detection and analysis system. This process is referred to herein as "cleaning" the sample in order to remove unwanted substrates or products of the hybridization or primer extension reactions and thus enrich for the desired products of these reactions. The sample can be "cleaned" in a number of ways including column purification in which for example the desired products flow through a column unrestrained due to their size while all other reaction constituents are retained in the column. Cleaning can also occur by subjecting the reaction sample to nucleases in order to digest unbound target and probes. Those of ordinary skill in the art will be able to determine which cleaning process is best suited without undue experimentation.

In several methods of the invention, the haplotype of a sample is determined. As used herein, a "haplotype" is a genomic sequences that is imparted by either parent and that varies among the population at large. A haplotype can include a group of alleles of linked genetic loci contributed by either parent, but it is not so limited.

As used herein, an "allele" is a form of a genetic locus imparted by either parent, and which is varies among the population at large. Alleles in a more limited sense can also refer to the two different copies of each genetic locus that every diploid individual carries and that together impart physical characteristic to such an individual.

As used herein, a "polymorphism" is a difference in a nucleic acid sequence, preferably a genomic sequence, in an individual that is different from the wild type sequence determined by the majority of the population.

The term "nucleic acid" is used herein to mean multiple nucleotides (i.e. molecules comprising a sugar (e.g. ribose or deoxyribose) linked to an exchangeable organic base, which is either a substituted pyrimidine (e.g. cytosine (C), thymidine (T) or uracil (U)) or a substituted purine (e.g. adenine (A) or guanine (G)). As used herein, the terms refer to oligoribonucleotides as well as oligodeoxyribonucleotides. The terms shall also include polynucleosides (i.e. a polynucleotide minus a phosphate) and any other organic base containing polymer. Nucleic acid molecules can be obtained from existing nucleic acid sources (e.g., genomic or cDNA), or by synthetic means (e.g. produced by nucleic acid synthesis).

The target nucleic acid molecules commonly have a phosphodiester backbone because this backbone is most common in vivo. However, they are not so limited. For example, they may have backbone modifications, such as nuclease resistant phosphorothioate backbones or peptide bond backbones. These latter types of modifications are more preferably used in the probes of the invention. Other backbone modifications are known in the art and are equally applicable to the invention. One of ordinary skill in the art is capable of preparing such nucleic acid molecules without undue experimentation.

In some embodiments, the nucleic acids of the invention are denatured and present in a single stranded form. This can be accomplished by modulating the environment of a double stranded nucleic acid including singly or in combination increasing temperature, decreasing salt concentration, and the like. Methods of denaturing nucleic acids are known in the art.

The methods of the invention are used to analyze polymers based on markers that recognize and bind to units within a polymer. A "unit" of a polymer, as used herein, refers to a particular linear arrangement of one or preferably more monomers (i.e., a particular defined sequence of monomers) within a target polymer. For example, a unit in a nucleic acid molecule consists of a particular sequence of nucleotides linked to one another. The unit may be of any length. For example, the nucleic acid unit may consist of one, or two nucleotides (i.e., a dinucleotide or a 2-mer), or three nucleotides (i.e., a trinucleotide or a 3-mer), or four nucleotides (i.e., a tetranucleotide or a 4-mer), and so on.

Many of the methods provided herein involve the use of a unit specific marker or a probe that binds to the polymer being studied in a sequence-specific manner. A "unit specific marker" is a molecule that specifically recognizes and binds to particular units within a polymer in a sequence-specific manner. As used herein, the terms "unit specific marker" and "probe" are used interchangeably.

Binding of a unit specific marker to a nucleic acid molecule indicates the presence and location of a unit in the target nucleic acid molecule. As used herein, a polymer that is bound by a unit specific marker is "labeled" with the unit specific marker. The position of the unit specific marker along the length of a target polymer generally the location of a particular unit in the polymer, in most instances. If a unit specific marker binds to a target polymer under conditions that favor specific binding, this indicates that the corresponding unit (and sequence) is present in the polymer. If a unit specific marker fails to bind to a target polymer under the same conditions, this generally indicates that the corresponding unit (and sequence) is not present in the polymer.

The unit specific marker may itself be a polymer but it is not so limited. Examples of suitable polymers are nucleic acid molecules (useful as unit specific markers for target polymers that are themselves nucleic acid molecules) and peptides and polypeptides (useful as unit specific markers for target polymers that are nucleic acid molecules and peptides). As used herein a "peptide" is a polymer of amino acid residues connected preferably but not solely with peptide bonds. Other unit specific markers include but are not limited to sequence-specific major and minor groove binders and intercalators, nucleic acid binding peptides or polypeptides, sequence-specific peptide-nucleic acids (PNAs), and peptide binding proteins, etc. Many unit specific markers exist and are known to those of skill in the art. Preferably, unit specific markers are themselves nucleic acid molecules.

The unit specific markers (i.e., probes) can include nucleotide derivatives such as substituted purines and pyrimidines (e.g., C-5 propyne modified bases (Wagner et al., *Nature Biotechnology* 14:840–844, 1996)). Suitable purines and pyrimidines include but are not limited to adenine, cytosine, guanine, thymidine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. The unit specific marker can also include non-naturally occurring nucleotides, or nucleotide analogs. Other such modifications are known to those of skill in the art.

The probes also encompass substitutions or modifications, such as in the bases and/or sugars. For example, they include nucleic acid molecules having backbone sugars which are covalently attached to low molecular weight organic groups other than a hydroxyl group at the 3' position and other than a phosphate group at the 5' position. Thus, modified nucleic acid molecules may include a 2'-O-alkylated ribose group. In addition, modified nucleic acid molecules may include sugars such as arabinose instead of ribose. Thus the probes may be heterogeneous in composition at both the base and backbone level. In some embodiments, the probes are homogeneous in backbone composition (e.g., all phosphodiester, all phosphorothioate, all peptide bonds, etc.).

When the probes used in vivo e.g., added to live cells or tissues containing endo- and exo-nucleases, it may be preferable to use probes that are resistant to degradation from such enzymes. A "stabilized nucleic acid molecule" shall mean a nucleic acid molecule that is relatively resistant to in vivo degradation (e.g., via an endo- or exo-nuclease).

In some embodiments, the probe is a peptide nucleic acid (PNA), a bisPNA clamp, a locked nucleic acid (LNA), a ssPNA, a pseudocomplementary PNA (pcPNA), a two-armed PNA (as described in co-pending U.S. patent application Ser. No. 10/421,644 and PCT application having serial number PCT/US03/12480, filed on Apr. 23, 2003), or co-polymers thereof (e.g., a DNA-LNA co-polymer). The probe may also be comprised partially or completely of RNAi which are double stranded RNA molecules reportedly effective in targeting nucleic acid molecules. It is to be understood that any nucleic acid analog that is capable of formation of at least a Hoogsteen hybrid can be used as a probe or unit specific marker.

The probes can also be stabilized in part by the use of other backbone modifications. The invention intends to embrace in addition to the peptide and locked nucleic acids discussed herein, the use of the other backbone modifications such as but not limited to phosphorothioate linkages, combinations of phosphodiester and phosphorothioate nucleic acid, methylphosphonate, methylphosphorothioate, phosphorodithioate, p-ethoxy, and combinations thereof.

The method embraces the simultaneous use of two or more unit specific markers that may be identical in nature or binding specificity, but it is not so limited.

The probes are preferably single stranded, but they are not so limited.

The unit specific marker can be of any length, as can the unit to which it binds. In instances in which the polymer and the probe are both nucleic acid molecules, the length of the unit and the unit specific marker are generally the same. The length of the marker will depend upon the particular embodiment. The marker length may range from at least 2, at least 3, at least 4, at least 5, at least 6, at least 7, at least 8, at least 9, at least 10, at least 12, at least 15, at least 20, at least 25, at least 50, at least 75, at least 100, at least 150, at least 200, at least 250, at least 500, or more nucleotides (including every integer therebetween as if explicitly recited herein). Preferably, the probes are at least 4 nucleotides in length to in excess of 1000 nucleotides in length.

In some embodiments, shorter markers are more desirable, since they provide much sequence information leading to a higher resolution sequence map of the target nucleic acid molecule. Longer markers are desirable when unique gene-specific sequences are being detected. The length of the probe however determines the specificity of binding. Proper hybridization of small sequences is more specific than is hybridization of longer sequences because the longer sequences can embrace mismatches and still continue to bind to the target depending on the conditions. One potential limitation to the use of shorter probes however is their inherently lower stability at a given temperature and salt concentration. In order to avoid this latter limitation, bisPNA or two-arm PNA probes can be used which allow both shortening of the probe and sufficient hybrid stability in order to detect probe binding to the target nucleic acid molecule.

Another consideration in determining the appropriate probe length is whether the target sequence (i.e., the sequence being detected) is unique or not. If the method is intended only to sequence the target nucleic acid molecule, then unique sequences may not be that important provided the target sequences are sufficiently spaced apart from each other to distinguish the signal from the binding of each. That is, the target sequence should occur at distances that can be discerned as separate sites along the polymer; otherwise, the signals merge and only one sequence is observed. As long as the location of binding of separate probes along the length of a target polymer can be distinguished, it should be clear that a greater resolution is possible using smaller probes.

As used herein, the term "known detection resolution" refers to the closest distance that two markers having the same label can be positioned relative to each other along the length of a target and still be individually detected and thus resolvable as two separate markers, using prior art methods. It is possible to detect markers positioned at less than the known detection resolution if adjacent markers are each labeled with a different detectable label, as described in published PCT Application PCT/US02/29687 (WO03/025540), filed Sep. 18, 2002 and published May 27, 2003.

As will be described in greater detail below, a marker that is "labeled" with a detectable label means that the marker is covalently or non-covalently conjugated to a detectable molecule such as but not limited to a fluorophore.

In some instances, the probes can be synthesized to have groups other than and/or in addition to nucleotides attached thereto. For example, the probes can also comprise one or more reactive groups (e.g., for conjugation to a detectable label, as described below), one or more amino acids, or detectable molecules (as described below).

The probes of the invention are labeled with detectable molecules. As used herein, the terms "detectable molecules" and detectable labels" are used interchangeably. The detectable molecule can be detected directly, for example, by its ability to emit and/or absorb light of a particular wavelength. Alternatively, a molecule can be detected indirectly, for example, by its ability to bind, recruit and, in some cases, cleave another molecule which itself may emit or absorb light of a particular wavelength, for example. An example of indirect detection is the use of an enzyme which cleaves an exogenously added substrate into visible products. The label may be of a chemical, peptide or nucleic acid nature although it is not so limited. When two or more detectable molecules are to be detected (e.g., in order to observe a color coincident event), the detectable molecules should be distinguishable from each other. This means that each emits a different and distinguishable signal from the other.

Detectable molecules can be conjugated to probes using chemistry that is known in the art. The labels may be directly linked to the DNA bases or may be secondary or tertiary units linked to modified DNA bases. Labeling with detectable molecules can be carried out either prior to or after binding to a target nucleic acid molecule. In preferred embodiments, a single nucleic acid molecule is bound by several different probes at a given time and thus it is advisable to label such probes prior to target binding. Labeled probes are also commercially available.

Generally, the detectable molecule can be selected from the group consisting of an electron spin resonance molecule (such as for example nitroxyl radicals), a fluorescent molecule, a chemiluminescent molecule, a radioisotope, an enzyme substrate, a biotin molecule, an avidin molecule, a streptavidin molecule, an electrical charged transducing or transferring molecule, a nuclear magnetic resonance molecule, a semiconductor nanocrystal or nanoparticle, a colloid gold nanocrystal, an electromagnetic molecule, a ligand, a microbead, a magnetic bead, a paramagnetic particle, a quantum dot, a chromogenic substrate, an affinity molecule, a protein, a peptide, a nucleic acid molecule, a carbohydrate, an antigen, a hapten, an antibody, an antibody fragment, and a lipid.

Specific examples of detectable molecules include radioactive isotopes such as $P^{32}$ or $H^3$, fluorophores such as fluorescein isothiocyanate (FITC), TRITC, rhodamine, tetramethylrhodamine, R-phycoerythrin, Cy-3, Cy-5, Cy-7, Texas Red, Phar-Red, allophycocyanin (APC), epitope tags such as the FLAG or HA epitope, and enzyme tags such as alkaline phosphatase, horseradish peroxidase, β-galactosidase, and hapten conjugates such as digoxigenin or dinitrophenyl, etc. Other detectable markers include chemiluminescent and chromogenic molecules, optical or electron density markers, etc. The probes can also be labeled with semiconductor nanocrystals such as quantum dots (i.e., Qdots), described in U.S. Pat. No. 6,207,392. Qdots are commercially available from Quantum Dot Corporation.

In some embodiments, the probes are labeled with detectable molecules that emit distinguishable signals detectable by one type of detection system. For example, the detectable molecules can all be fluorescent labels or radioactive labels. In other embodiments, the probes are labeled with molecules that are detected using different detection systems. For example, one probe may be labeled with a fluorophore while another may be labeled with radioactive molecule.

Analysis of the nucleic acid involves detecting signals from the detectable molecules, and determining their position relative to one another. In some instances, it may be desirable to further label the target nucleic acid molecule with a standard marker that facilitates comparison of information obtained from different targets. For example, the standard marker may be a backbone label, or a label that binds to a particular sequence of nucleotides (be it a unique sequence or not), or a label that binds to a particular location in the nucleic acid molecule (e.g., an origin of replication, a transcriptional promoter, a centromere, etc.).

One subset of backbone labels are nucleic acid stains that bind nucleic acid molecules in a sequence independent manner. Examples include intercalating dyes such as phenanthridines and acridines (e.g., ethidium bromide, propidium iodide, hexidium iodide, dihydroethidium, ethidium homodimer-1 and -2, ethidium monoazide, and ACMA); some minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc. Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

It is to be understood that the labeling of the probe should not interfere with its ability to recognize and bind to a nucleic acid molecule.

The nucleic acid probes can also be labeled using antibodies or antibody fragments and their corresponding antigen or hapten binding partners. Detection of such bound antibodies and proteins or peptides is accomplished by techniques known to those skilled in the art. Hapten conjugates such as digoxigenin or dinitrophenyl can also be used. Antibody/antigen complexes which form in response to hapten conjugates are easily detected by linking a label to the hapten or to antibodies which recognize the hapten and then observing the site of the label. Alternatively, the antibodies can be visualized using secondary antibodies or fragments thereof that are specific for the primary antibody used. Polyclonal and monoclonal antibodies may be used. Antibody fragments include Fab, F(ab)$_2$, Fd and antibody fragments which include a complementarity determining region (CDR) and more particularly a CDR3.

In other embodiments, the probes are labeled with substrates for enzymatic reactions. Suitable enzymatic reactions include those that generate a new nucleic acid product that can be detected using a single molecule detection system. These enzymatic reactions include primer extension reactions and ligase-mediated reaction, both of which form newly synthesized nucleic acid molecules. In some embodiments, the detectable product can in turn be amplified prior to being detected, but this is not essential, as the detection systems described herein are capable of detecting single nucleic acid molecules. In some embodiments, a detectable product can only be formed if two or more unit specific markers are located within a certain distance of each other. For example, if the enzymatic reaction is a polymerase chain reaction, then in order for the detectable product to be formed and amplified, it is necessary that at least two unit specific markers be bound to the target polymer.

In some instances, the probes of the invention can be further labeled with cytotoxic agents or nucleic acid cleaving enzymes. In this way, the probes can be used for therapeutic purposes as well as for nucleic acid detection and analysis. This may be particularly useful where the probe has sequence specificity to a known genetic mutation or translocation associated with a disorder or a predisposition to a disorder. In other embodiments, a probe that is specific for wild type sequence may be conjugated to a nucleic acid cleaving enzyme, and in this way used as a negative selection against wild type sequences in a sample. The ability to cleave and subsequently eliminate wild type sequences allows for the enrichment of unique sequences.

The invention embraces the use of a variety of detection systems. The nature of such detection systems will depend upon the nature of the label being detected. The nucleic acid molecule may be analyzed using a single molecule detection system. The detection system may also be a linear polymer detection system, but it is not so limited. As stated earlier, it is not necessary to linearize or stretch the nucleic acid molecule prior to analysis in some embodiments. This is particularly true if the analysis depends on the presence of a hybridization event, or if coincident detection is used. An example of a single molecule detection system is the Gene Engine™ system. Gene Engine™ technology is described in greater detail in PCT patent applications having Ser. Nos. WO98/35012, WO00/09757, and WO01/13088, published on Aug. 13, 1998, Feb. 24, 2000, and Feb. 22, 2001 respectively, in U.S. Pat. No. 6,355,420 B1 issued Mar. 12, 2002. The contents of these applications and patent, as well as those of other patents and references recited herein are incorporated by reference in their entirety. This system is capable inter alia of determining the spatial location of sequence-specific labels along a nucleic acid polymer. The order of nucleotides (i.e., the nucleotide sequence) can be derived from the relative spatial localization of sequence specific tags fixed to nucleic acid polymers. In many of the methods provided herein, it is not necessary to determine where the probe binds to the target, but rather simply that it does or does not bind. Accordingly, it is not always necessary that the target polymer be "linearized" or stretched out prior to interrogation (e.g., contact with a laser). Rather, the target polymer can be interrogated while it is intertwined provided that the detectable molecule is available for interrogation.

In some embodiments, an analysis intends to detect preferably two or more detectable signals. As described herein, a first unit specific marker can interact with the energy source to produce a first signal and a second unit specific marker can interact with the energy source to produce a second signal. The signals so produced may be different from one another, but in all cases must be distinguishable from each other, thereby enabling more than one type of unit to be detected on a single target polymer. Use of detection molecules that emit distinct signals (e.g., one emits at 535 nm and the other emits at 630 nm) enables more thorough sequencing of a target polymer since units located within the known detection resolution can now be separately detected and their positions can be distinguished and thus mapped along the length of the polymer.

The labeled polymer is exposed to an energy source in order to generate a signal from the label. As used herein, the labeled polymer is "exposed" to an energy source by positioning or presenting the labeled unit specific marker bound to the polymer in interactive proximity to the energy source such that energy transfer can occur from the energy source to the labeled unit specific marker, thereby producing a detectable signal. Interactive proximity means close enough to permit the interaction or change which yields that detectable signal.

The energy source may be selected from the group consisting of electromagnetic radiation, and a fluorescence excitation source, but is not so limited. "Electromagnetic radiation" as used herein is energy produced by electromagnetic waves. Electromagnetic radiation may be in the form of a direct light source or it may be emitted by a light emissive compound such as a donor fluorophore. "Light" as used herein includes electromagnetic energy of any wavelength including visible, infrared and ultraviolet. A fluorescence excitation source as used herein is any entity capable of making a source fluoresce or give rise to photonic emissions (i.e. electromagnetic radiation, directed electric field, temperature, physical contact, or mechanical disruption.)

In one aspect, the method further involves exposing the labeled polymer to a station to produce distinct signals arising from the labels of the unit specific markers. As used herein, a labeled polymer is "exposed" to a station by positioning or presenting the labeled unit specific marker bound to the polymer in interactive proximity to the station such that energy transfer or a physical change in the station can occur, thereby producing a detectable signal. A "station" as used herein is a region where a portion of the polymer (having a labeled unit specific marker bound thereto) is exposed to an energy source in order to produce a signal or polymer dependent impulse. The station may be composed of any material including a gas, but preferably the station is a non-liquid material. In one preferred embodiment, the station is a composed of a solid material. If the labeled unit specific marker interacts with the energy source at the station, then it is referred to as an interaction station. An "interaction station" is a region where a labeled unit specific marker and the energy source can be positioned in close enough proximity to each other to facilitate their interaction. The interaction station for fluorophores is that region where the labeled unit specific marker and the energy source are close enough to each other that they can energetically interact to produce a signal.

When the labeled unit specific markers are sequentially exposed to the station and/or the energy source, the marker (and thus polymer) and the station and/or the energy source move relative to each other. As used herein, when the marker and the station and/or energy source move relative to each other, this means that either the marker (and thus polymer) or the station and/or the energy source are both moving, or alternatively only one of the two is moving and other is stationary. Movement between the two can be accomplished by any means known in the art. As an example, the marker and polymer can be drawn past a stationary station by an electric current. Other methods for moving the marker and polymer past the station include but are not limited to magnetic fields, mechanical forces, flowing liquid medium, pressure systems, suction systems, gravitational forces, and molecular motors (e.g., DNA polymerases or helicases if the polymer is a nucleic acid, and myosin when the polymer is a peptide such as actin). Polymer movement can be facilitated by use of channels, grooves, or rings to guide the polymer. The station is constructed to sequentially receive the target polymer (with labeled unit specific markers bound thereto) and to allow the interaction of the label and the energy source.

The interaction station in a preferred embodiment is a region of a nanochannel where a localized energy source can interact with a polymer passing through the channel. The point where the polymer passes the localized region of agent is the interaction station. As each labeled unit specific marker passes by the energy source a detectable signal is generated. The energy source may be a light source which is positioned a distance from the channel but which is capable of transporting light directly to a region of the channel through a waveguide. An apparatus may also be used in which multiple polymers are transported through multiple channels. The movement of the polymer may be assisted by the use of a groove or ring to guide the polymer.

Other arrangements for creating interaction stations are embraced by the invention. For example, a polymer can be passed through a molecular motor tethered to the surface of a wall or embedded in a wall, thereby bringing units of the polymer sequentially to a specific location, preferably in interactive proximity to the energy source, thereby defining an interaction station. A molecular motor is a compound such as polymerase or helicase which interacts with the polymer and is transported along the length of the polymer past each unit. Likewise, the polymer can be held stationary and a reader can be moved along the polymer, the reader having attached to it the energy source. For instance the energy source may be held within a scanning tip that is guided along the length of the polymer. Interaction stations then are created as the energy source is moved into interactive proximity to each labeled unit specific marker.

As discussed earlier many methods may be used to move the polymer linearly across the channel and past the interaction station or signal generation station. A preferred method according to the invention utilizes and electric field. An electric field can be used to pull a polymer through a channel because the polymer becomes stretched and aligned in the direction of the applied field as has previously been demonstrated in several studies (Bustamante, 1991; Gurrieri et al., 1990; Matsumoto et al., 1981). The most related experiments regarding linear crossing of polymers through channels arise from experiments in which polymeric molecules are pulled through protein channels with electric fields as described in Kasianowicz et al., 1996 and Bezrukov et al., 1994, each of which is hereby incorporated by reference.

In order to achieve optimal linear crossing of a polymer across a channel it is important to consider the channel diameter as well as the method used to direct the linear crossing of the polymer e.g., an electric field. The diameter of the channels should correspond well with that of the labeled polymer. The theory for linear crossing is that the diameter of the channels correspond well with that of the polymer. For example the ring-like sliding clamps of DNA polymerases have internal diameters that correspond well with the diameter of double-stranded DNA and are successful at achieving linear crossing of a DNA molecule. Many kilobases of DNA can be threaded through the sliding clamps. Several references also have demonstrated that linear crossing of DNA through channels occurs when the diameter of the channels corresponds well with that of the diameter of the DNA. (Bustamante, 1991; Gurrieri et al., 1990; Matsumoto et al., 1981).

The interaction station uses unique arrangements and geometries that allow the localized radiation spot to interact with one or several polymer units or unit specific marker labels that are on the order of nanometers or smaller. Optical detector detects light modified by the interaction and provides a detection signal to the processor.

As the labeled polymer passes through interaction station, the optical source emits radiation electric or electromagnetic field, X-ray radiation, or visible or infrared radiation for characterizing the polymer passing through the interaction station directed to an optical component of interaction station. The optical component produces a localized radiation spot that interacts directly with a) the polymer backbone (e.g., when the polymer backbone is bound to an intercalator that emits radiation), b) labels attached to the unit specific markers, or c) both the backbone units and the labels. The localized radiation spot includes non-radiating near field or an evanescent wave, localized in at least one dimension. The localized radiation spot provides a much higher resolution than the diffraction-limited resolution used in conventional optics.

The interaction between the labeled unit specific marker and the agent can take a variety of forms. As a first example, the interaction can take place between an energy source that is electromagnetic radiation and a labeled unit specific marker that is a light emissive compound (preferably, a unit specific marker that is extrinsically labeled with a light emissive compound). When the light emissive compound is exposed to the electromagnetic radiation (such as by a laser beam of a suitable wavelength or electromagnetic radiation emitted from a donor fluorophore), the electromagnetic radiation causes the light emissive compound to emit electromagnetic radiation of a specific wavelength. A second type of interaction involves an energy source that is a fluorescence excitation source and a unit specific marker that is labeled with a light emissive compound. When the light emissive unit is contacted with the fluorescence excitation source, the fluorescence excitation source causes the light emissive compound to emit electromagnetic radiation of a specific wavelength. In both examples, the signal that is measured exhibits a characteristic pattern of light emission, indicating that a particular unit of the polymer is present at that particular location.

A variation of these types of interaction involves the presence of a third element of the interaction, a proximate compound which is involved in generating the signal. For example, a unit specific marker may be labeled with a light emissive compound which is a donor fluorophore and a proximate compound can be an acceptor fluorophore. If the light emissive compound is placed in an excited state and brought proximate to the acceptor fluorophore, then energy transfer will occur between the donor and acceptor, generating a signal which can be detected as a measure of the presence of the unit specific marker which is light emissive. The light emissive compound can be placed in the "excited" state by exposing it to light (such as a laser beam) or by exposing it to a fluorescence excitation source.

A set of interactions parallel to those described above can be created in which the light emissive compound is the proximate compound and the labeled unit specific marker is an acceptor source. In these instances the energy source is electromagnetic radiation emitted by the proximate compound, and the signal is generated by bringing the labeled unit specific marker in interactive proximity with the proximate compound.

The mechanisms by which each of these interactions produce detectable signals are known in the art. PCT applications WO98/35012, WO00/09757 and WO01/13088, published on Aug. 13, 1998, Feb. 24, 2000 and Feb. 22, 2001, respectively, and U.S. Pat. No. 6,355,420 B1 issued Mar. 12, 2002, describe the mechanism by which a donor and acceptor fluorophore interact according to the invention to produce a detectable signal including practical limitations which are known to result from this type of interaction and methods of reducing or eliminating such limitations.

Once the signal is generated it can then be detected. The particular type of detection means will depend on the type of signal generated which of course will depend on the type of interaction which occurs between the unit and the energy source. Most of the interactions involved in the method will produce an electromagnetic radiation signal. Many methods are known in the art for detecting electromagnetic radiation signals. Preferred devices for detecting signals are two-dimensional imaging systems that have, among other parameters, low noise, high quantum efficiency, proper pixel-to-image correlation, and efficient processing times. An example of a device useful for detecting signals is a two-dimensional fluorescence imaging system which detects electromagnetic radiation in the fluorescent wavelength range.

The detection system can be selected from any number of detection systems known in the art. These include a charge coupled device (CCD) detection system, an electron spin resonance (ESR) detection system, an electrical detection system, a photographic film detection system, a fluorescent detection system, a chemiluminescent detection system, an enzyme detection system, an atomic force microscopy (AFM) detection system, a scanning tunneling microscopy (STM) detection system, an optical detection system, a nuclear magnetic resonance (NMR) detection system, a near field detection system, a total internal reflection (TIR) detection system, and a electromagnetic detection system.

Other single molecule nucleic acid analytical methods which involve elongation of DNA molecule can also be used in the methods of the invention. These include optical mapping (Schwartz et al., 1993; Meng et al., 1995; Jing et al., 1998; Aston, 1999) and fiber-fluorescence in situ hybridization (fiber-FISH) (Bensimon et al., 1997). In optical mapping, nucleic acid molecules are elongated in a fluid sample and fixed in the elongated conformation in a gel or on a surface. Restriction digestions are then performed on the elongated and fixed nucleic acid molecules. Ordered restriction maps are then generated by determining the size of the restriction fragments. In fiber-FISH, nucleic acid molecules are elongated and fixed on a surface by molecular combing. Hybridization with fluorescently labeled probe sequences allows determination of sequence landmarks on the nucleic acid molecules. Both methods require fixation of elongated molecules so that molecular lengths and/or distances between markers can be measured. Pulse field gel electrophoresis can also be used to analyze the labeled nucleic acid molecules. Pulse field gel electrophoresis is described by Schwartz et al. (1984). Other nucleic acid analysis systems are described by Otobe et al. (2001), Bensimon et al. in U.S. Pat. No. 6,248,537, issued Jun. 19, 2001, Herrick and Bensimon (1999), Schwartz in U.S. Pat. No. 6,150,089 issued Nov. 21, 2000 and U.S. Pat. No. 6,294,136, issued Sep. 25, 2001. Other linear polymer analysis systems can also be used, and the invention is not intended to be limited to solely those listed herein.

The following Examples illustrate various embodiments of the invention. These Examples are illustrative and do not narrow the scope of the invention.

EXAMPLES

It is to be understood that although many of the examples provided herein refer to DNA as the molecule being analyzed, the invention intends to embrace all nucleic acid molecules, and in some embodiments other polymers as well such as peptides and carbohydrates. Importantly, the methods are suitable for RNA analysis which can be performed without amplification or significant degradation of the RNA sample. Non-nucleic acid polymers can be analyzed using agents that bind to them such as aptamers which can be developed to bind specifically to a broad range of compounds. Thus, although the examples refer explicitly to DNA, the methods can be used for any polymer type, whether it is nucleic acid in nature or not.

I. Haplotyping Methods.

Haplotyping can be carried out using multi-color analysis. These methods can be used in conjunction with different methods of single molecule readout including but not limited to confocal imaging, total internal reflection (TIR) detection, optical imaging, and scanning-based approaches. This method is described briefly herein. Regions of a nucleic acid such as a genomic DNA molecule are either directly tagged or accessed using sequence discriminatory chemistries such as primer extension technology. Two or more polymorphic sites are tagged using different colors. The coincident detection of these colors allow for the determination of the haplotypes present in the sample. This is illustrated in FIG. 1.

As show in FIG. 1, the different haplotypes in the sample are determined by the coincidence detection of the two fluorophores in the sample. The coincidence detection can be detected through the acquisition of sequential scans or images that recognize the different spectral characteristics of the sample.

Other haplotyping methods include the fixing of DNA molecules to a surface and spatially determining the haplotype based on position or spectrally-dependent colors. In this particular embodiment, the amplified or genomic molecules of interest are fixed to a surface and polymorphism dependent reactions are performed to allow the determination of haplotypes over the region of interest. This reaction may include polymorphism scoring reactions such as primer-extension reactions ligase-mediated detection, allele-specific hybridization (ASH), or other methods.

The sequence of events in the detection of single molecule haplotypes is as follows: (1) fixing the DNA molecules to the surface using techniques known in the art, (2) denaturing the DNA (if double-stranded), (3) detecting the polymorphisms along two or more sites along the length of the DNA. The above steps can be performed in any order that is suitable and are not limited to the order presented above. For instance, the DNA molecules can be hybridized with primers and extended with dideoxy fluorophores in solution first. Subsequently, this solution of tagged DNA molecules can then be separated from any free fluorophores in solution. The tagged DNA molecules can then be fixed to the surface and detected using an imaging or scanning-based system.

Figure 2:
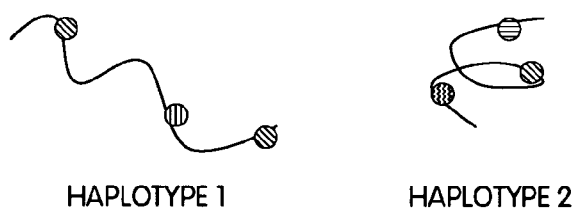
FIG. 2 is a schematic showing the different spatial arrangements of probes on nucleic acid molecules being characterized.

The detection could be a multicolor detection mechanism, a differential intensity detection method, or a spatial detection method. FIG. 2 illustrates some of these examples. In FIG. 2, the DNA molecules are fixed to the surface in random orientation. The differential color labeling of the polymorphic sites may or may not be coincident on the image depending on: (1) how the DNA molecule was affixed to the surface and (2) how far apart the polymorphic sites are based on the physical distance. There is no limitation on the number of polymorphisms (e.g., single nucleotide polymorphisms (SNPs), microsatellites, insertions/deletions, etc.) that can be assayed because there are a multitude of colors and differential tags available that can be used.

The presence or absence of the particular patterns are indicative of the haplotype of the sample. In a given human sample, for a particular region of the genome, there can only be a maximum of two haplotypes present in the sample because of the two possible alleles. Different tagging patterns can be used to identify the different haplotypes in the mixture. These tagging patterns may include the use of multiple color combinations along the length of the DNA molecules. Different intensities of the fluorescent tags can be used.

a. Fixed or Arrayed Oligonucleotides for Haplotype Determination.

More complex methods of haplotype determination involve the use of oligonucleotides fixed or arrayed to a surface and various subsequent polymorphism detection methods to determine the linked polymorphisms on that particular strand of DNA.

Figure 3:
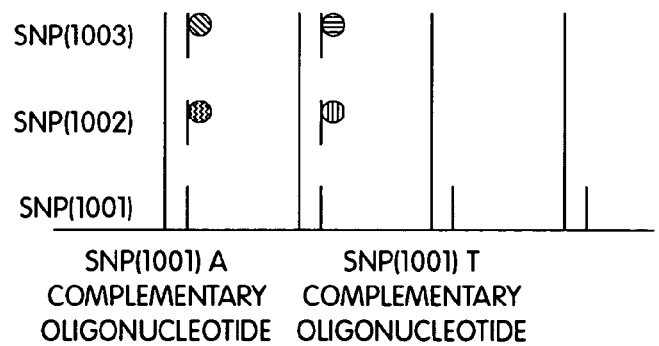
FIG. 3 is shows the binding of nucleic acid haplotypes onto a fixed or arrayed pattern of oligonucleotides.

FIG. 3 illustrates an embodiment of these methods. The haplotypes are determined by an allele-specific hybridization to spatially defined locations on the surface. In this particular example, SNP(1001) denotes a SNP position at a certain position in the genome. SNP(1002) and SNP(1003) denote positions downstream of SNP(1001) that give the spatial haplotypes for the particular SNP. The fixed capture oligonucleotide allows an initial discrimination between variants in SNP(1001) position. Subsequent interrogation of the downstream SNPs (i.e., 1002 and 1003) with multiple colors allows the determination of the haplotypes present in the mixture.

Variations on this embodiment may include the use of the fixed oligonucleotide as the capture oligonucleotide for that particular region of the genome. With this scheme, knowledge of the oligonucleotide sequence with spatial position allows the determination of the particular haplotypes at that particular position. This particular embodiment does not require the use of single molecule detection to determine the haplotype of the DNA sample, but would benefit from the use of single molecule detection. Single molecule detection allows the use of genomic DNA as opposed to amplified DNA to assay the haplotypes.

Arrayed methods of haplotype determination allow the determination of multiple haplotypes across the genome through the use of arrayed oligonucleotides that are specific for different regions of the genome.

Figure 4:
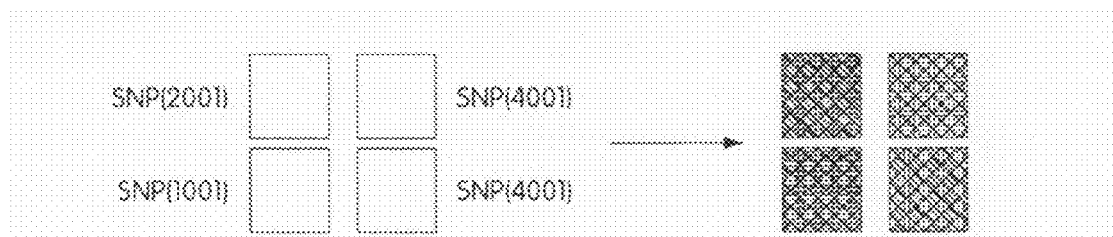
FIG. 4 shows the haplotype determination using an oligonucleotide that is fixed to a surface using an oligonucleotide specific for the particular haplotypic region of the genome. For a two SNP haplotype, four colors representing the chemistries at the two different sites allows full determination of the haplotype.

FIG. 4 shows haplotype determination using multiple color analysis for each location and one location specific capture oligonucleotide for each location.

Figure 5:
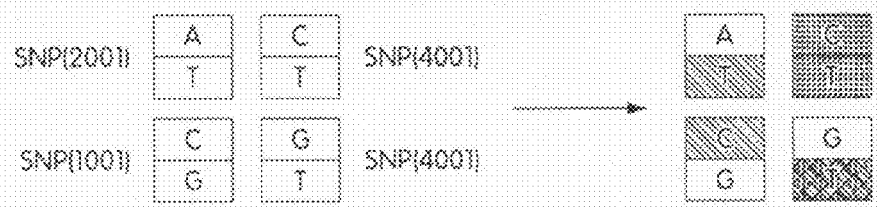
FIG. 5 shows a method for haplotype determination using multiple color analysis for an SNP specific capture oligonucleotide at each position in an array. The haplotype is determined by further hybridizing a primer-extended product of one of two colors, a green oligonucleotide or an orange labeled oligonucleotide for the second site.

FIG. 5 shows haplotype determination using multiple color analysis for a SNP-specific capture oligonucleotide at each position. The haplotype is determined by further hybridizing a primer-extended product of one of two colors, a green oligonucleotide or an orange oligonucleotide for the second site.

Figure 6:
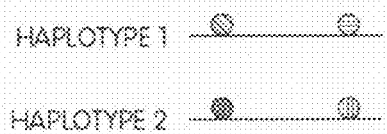
FIG. 6 is a schematic showing labeling of two sites in order to determine a haplotype. The figure is intended to demonstrate the need to distinguish between alleles prior to analysis.

FIG. 6 shows the haplotype determination using an oligonucleotide that is fixed to a surface using an oligonucleotide specific for the particular haplotypic region of the genome. For a two SNP haplotype, 4-colors for the chemistries at the two different locations allows full determination of the haplotype of the sample.

The methods in FIGS. 5 and 6 are not dependent on single molecule detection, but rather dependent on the ability to distinguish colors and haplotypes based on spatial and colorimetric determination.

b. Haplotype Analysis Using Allele Separation.

Haplotypes can be determined using non-single molecule methods if the alleles are separated. The concept of allele separation is important because otherwise the alleles remain mixed together and the readout will combine the haplotype information indiscriminately. Traditionally, methods of allele separation have been through cloning. Other methods include the use of somatic cell hybrids to isolate a single chromosome at one time. Currently, the somatic cell hybrids and kits for making such hybrids can be purchased through GMP Genetics (MA).

Figure 7:
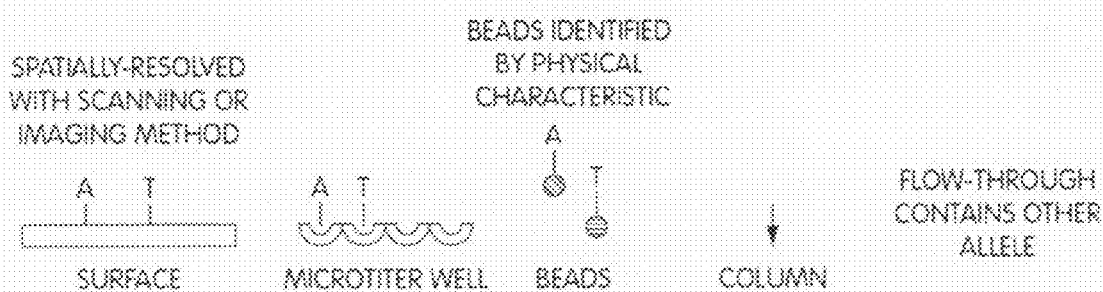
FIG. 7 is a schematic showing various ways of physically separating alleles prior to analysis.

PCR amplified regions of the genome also need to be separated in order to determine the haplotype because both alleles are amplified concurrently. Without the separation of the alleles, the haplotype information is combined. As show in FIG. 7, without separation of the alleles, the detection of the two haplotypes upon readout yields the mixture of the four colors. However, if the two alleles were separated into two different chambers and read out, then it would be possible to derive information about the haplotypes separately.

Figure 8:
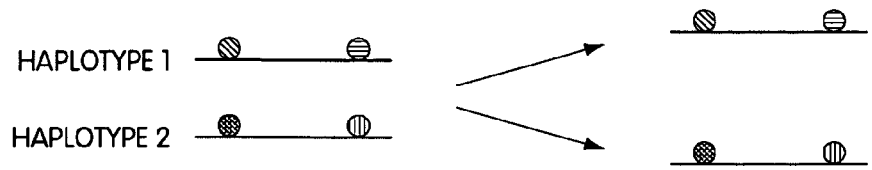
FIG. 8 is a schematic showing that a two to four color tagging system can be used to determine haplotype.

The invention embraces methods for the separation of alleles. These include allele separation using spatial separation on a surface, such as in an array format. Other methods of allele separation include the use of allele-specific hybridization in various formats to allow the separation of the two alleles. These methods of separation of the two alleles include: spatial separation on a surface, different microtiter wells with a different allele-specific oligonucleotide, beads with different allele-specific oligonucleotides, columns with allele-specific oligonucleotides, and gel-based methods of allele separation. These are illustrated in FIG. 8.

Figure 9:
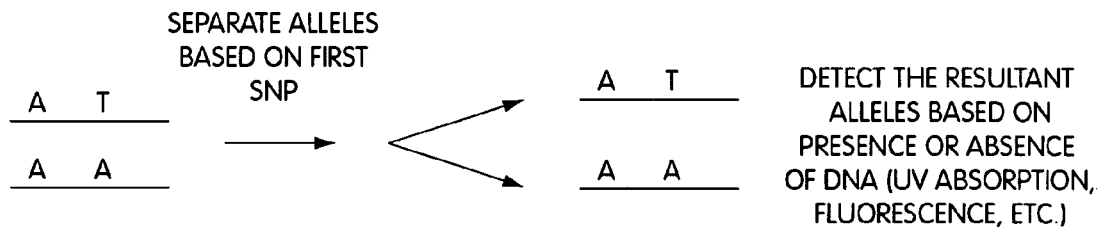
FIG. 9 is a schematic showing a method in which alleles are first separated based on a first SNP.

After the alleles are separated, various tagging approaches can be utilized to assay the various haplotypes in the solution. For instance, multi-color approaches can be used to determine the presence of the haplotypes, as shown in FIG. 9. FIG. 9 shows that haplotypes can be determined through the use of two to four color tagging schemes in which each color codes for a different biallelic SNP. The chemistry for the multi-color readout of the haplotypes can be primer-extension of fluorescent ddNTPs, fluorescent allele-specific hybridization (oligos, PNAs, synthetic sequence-specific binding agents), allele-specific ligation, or any other method that allows the calorimetric identification of the SNPs.

Figure 10:
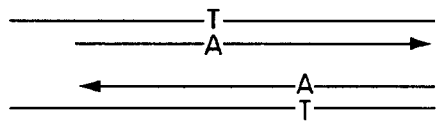
FIG. 10 shows the combined use of allele-specific PCR and single molecule detection.

Determination of the haplotypes can be accomplished using further separation steps, as show in FIG. 10.

c. Allele-specific PCR for Single Molecule Haplotype Analysis.

Figure 11:
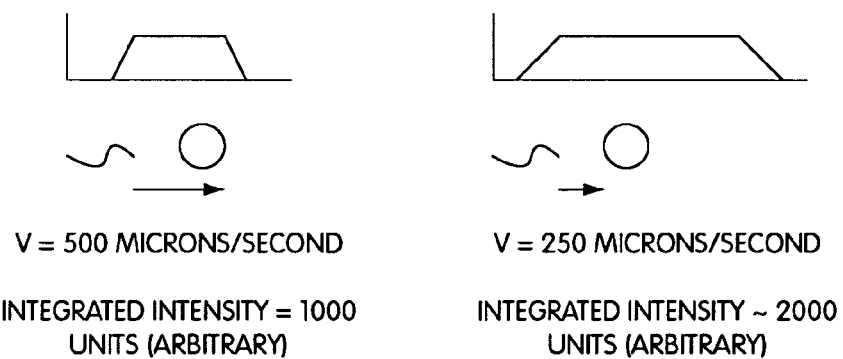
FIG. 11 shows the distribution of signal as a label moves through a detection channel as a function of velocity.

Haplotypes can also be determined through the use of allele-specific PCR. Allele-specific PCR coupled together with single molecule detection allows a single PCR reaction to determine the presence or absence of up to four possible haplotypes in the solution. Allele-specific PCR allows a unique ability to determine the presence of haplotypes in a solution through the allele-specificity of allele-specific PCR. Allele-specific PCR requires the matching of allele-specific information on the 3'-ends of the primer. Only through the direct match of the two alleles does it allow for the amplification of the PCR product. FIG. 11 illustrates allele-specific PCR coupled with single molecule detection.

The matching of the terminal 3' base allows for the formation of the PCR product. In the case of two SNPs that are required to be assayed by allele-specific PCR, there are four possible PCR products that can be formed. The four products that arise would be analyzed independently through the use of individual reactions and gel electrophoresis analysis using standard molecular biology methods. In contrast, the use of single-molecule analysis methods allows the direct determination of the presence or absence of the four potential alleles (haplotypes) in the solution through the use of four primers that are labeled each with a different fluorophore. Each of the four primers have a particular SNP or 3' specificity. Amplification of the products that are in the solution allow for the analysis of the different PCR products. The potential four alleles are then determined through the use of single molecule detection methods that allow the precise determination of the haplotypes present in the sample.

For instance, if a sample from an individual with a heterozygous haplotype of AG and AT is being assayed, then the allele-specific PCR amplification reaction would amplify the two haplotypes. The amplification primers would be labeled with a detectable label such as a fluorophore. As an example, the primer with the 3' end specific for the "A" SNP can be labeled with coumarin and the primers specific for the "G" and "T" SNPs can be labeled with TAMRA and Cy-5, respectively. The amplification reaction thus links the coumarin-TAMRA for the "AG" haplotype and coumarin-Cy5 for the "AT" haplotype.

Single molecule detection of the individual products allows the analysis of the different haplotypes present in the mixture through the coincident detection or spatial localization of the haplotypes. The single molecule detection can be accomplished through the use of imaging methods such as total internal reflection detection or through the use of point detection methods such as near-field detection or confocal single molecule detection methods. For instance, if these products were spread onto a glass surface and then imaged using a multi-color single molecule detection technology, then the analysis would be straightforward. Alternatively, if the products were flowed through a nanofabricated chip through a point detection system, then the detection of the coincidence of the different colors would allow the determination of the presence or absence of the haplotypes in the solution mixture.

II. Novel Methods for Determining Size and Distance in DNA.

Various methods of tagging and labeling allow for the unique sizing of DNA molecules. Sizing DNA is traditionally important for the analysis of restriction fragments, PCR fragments, and DNA sequencing products. Through the use of single molecule analysis methods, the need for size separation, either through a capillary or a slab gel, is not required.

Sizing of nucleic acids is routinely used in forensic analyses as well as in paternity determinations, inter alia.

a. Sizing Using Combined Integrated Intensity and Velocity Determination.

Improved methods of sizing nucleic acid molecules are also described that allow for greater accuracy of the measurement of the size of a nucleic acid molecule using integrated intensity. Limitations inherent in the use of an integrated intensity approach include Gaussian beam profiles, non-uniform speed of movement through the excitation volume, non-uniform labeling along the length of the nucleic acid, and photon shot noise from the emitted signal The invention provides several solutions for overcoming these limitations. Some of them are related to the experimental apparatus and some are related to the labeling of the nucleic acid molecule. The correction of the Gaussian beam profile of a confocal laser spot for the determination of integrated intensity as correlated with size can be corrected for through the careful definition and restriction of the location of passage of the nucleic acid molecule through the Gaussian spot. This can be accomplished through the use of a narrow channel (i.e., 100 nm×100 nm) that is positioned within the beam and calibrated for the excitation intensity of the beam. Furthermore, through the use of such a channel, the nucleic acid molecule can be passed through multiple confocal spots and the average of the intensity of the nucleic acid molecule passing through all the spots can then be determined. The excitation volume can also be enlarged to be much greater than the diffraction limited spot to allow for less illumination inhomogeneity at the point of passage and thus measurement of the integrated intensity of the nucleic acid molecule. The simplest solution, however, is to take an imaging-based approach and a uniform illumination source to determine the integrated intensity of the nucleic acid molecules passing through the system.

Figure 12:
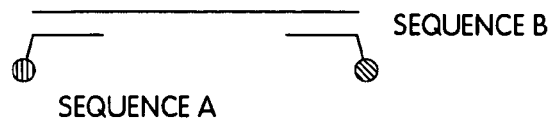
FIG. 12 is a schematic showing the use of end labels for determining size of a nucleic acid molecule.

If the experimental apparatus is a point illumination and detection scheme with the molecules passing through the excitation volume as a time-of-flight measurement, a confounding variable is the non-uniform speed of the molecules through the volume. This can be illustrated in the FIG. 12 which shows that the integrated intensity of molecules can be non-informative and arbitrary in light of nonuniform speeds of nucleic acid molecule movement through the system. A given number of fluorophores emits a certain number of photons per time collection window. The slower that a molecule moves through the spot, the longer the time of data collection, but the photon rate per collection window (bin) remains constant because of the assumed constant rate of photon emission. The experimental correction of this can be adjusted for through an experimental configuration that determines the velocity of the nucleic acid molecule and takes this information into consideration when determining the integrated intensity signal of passage of the molecule through the confocal beam. The estimation of the velocity of the nucleic acid molecule, through the use of multiple confocal illumination spots can thus approximate an accurate velocity profile that can be used in giving meaning to integrated intensity values.

In the case of the imaging-based approach to integrated intensity sizing, the measurements are more accurate given the uniformity of the illumination and the defined integration time for capture of the image. Another method to correct for the non-uniformity is to create a uniform velocity passage of nucleic acid molecules past the region of excitation. This can be done through the design of flow and nucleic acid molecule transport mechanisms that achieve this aim.

Non-uniform labeling of nucleic acid molecules with fluorophores can present a problem because the labeling is indicative of the size of the nucleic acid molecule. Intercalation of the nucleic acid molecules can depend on the intercalator dye used in the analysis. For example, some dyes bind more favorable to GC- or AT-rich regions of the genome, creating typical "banding" patterns as observed by fluorescence in situ hybridization (FISH). Other types of intercalator dyes bind to DNA uniformly, but are influenced by competitive binding to surfaces. This creates a non-uniformity that is random and unpredictable.

The invention encompasses the ability to label DNA uniformly and thus give rise to more accurate determination of the size of the DNA as estimated through the accurate determination of intercalator intensity. For instance, the type of labeling that is most robust and predictable is covalent labeling of the nucleic acid molecule. Single molecule analysis requires consistency and uniformity between different samples and thus intercalation can yield a relatively high error in the determination of molecular size. The base pair to intercalator ratio can be difficult to control under various conditions. In order to more accurately measure the size of nucleic acid molecules, a different labeling method is proposed that allows for more accurate measurement of the their lengths. This method allows a more precise labeling method through the use of covalently labeled base pairs in the nucleic acid molecule sample. This method uses fluorescent agents that are covalent bound to the nucleic acid molecule. These agents and kits for their use are commercially available from Panvera Corporation or Mirus Inc. The LabelIT kit for example allows the covalent binding of a fluorophore to the DNA molecule. This covalent binding allows a well-controlled incorporation of fluorophores along the backbone of the nucleic acid molecule. This increases the accuracy of the labeling and thus the ability to determine molecule size from the intensity of the nucleic acid molecule.

Photon shot-noise is another limitation in the determination of nucleic acid molecule length. Photon shot-noise arises from the statistical fluctuation of photon emission and collection of photons from any source.

b. Multicolor Sizing Methods.

Methods of sizing nucleic acid molecules can be performed using primers or other sequence-recognition reagents. The sizes of nucleic acid molecules can be determined in the following way. A nucleic acid molecule with a known sequence and length is present. In order to determine both the presence and the size of another nucleic acid molecule, a multicolor oligonucleotide tagging approach is employed. This tagging approach requires the sequence knowledge of the nucleic acid molecule to be targeted. This approach is illustrated in FIG. 13.

Figure 13:
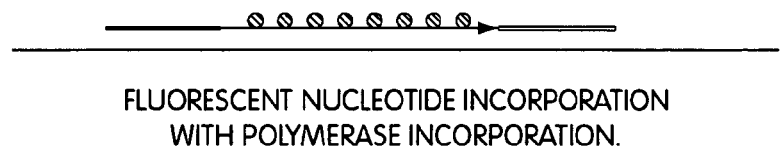
FIG. 13 is a schematic showing the uniform incorporation of fluorescent labels during a polymerase reaction.

In FIG. 13, the hybridization of two oligonucleotides with different fluorophores to the nucleic acid molecule allows one to determine whether the nucleic acid molecule is present in the sample and its size. In order to determine its size, the probe sequences are chosen so that they reside at a distance that is commensurate with the distance that is being measured. For instance, in a particular mixture of DNA molecules, if a 3000 base pair (bp) sequence needs to be detected, then if the sequences are chosen that are at a distance of less than 3000 bp apart, their presence on a single nucleic acid molecule indicates that the molecule is present but would not necessarily confirm the size of the fragment. Placing the oligonucleotides at a distance commensurate with the size of the target nucleic acid molecule allows the size of the fragment to be verified. The readout and the detection of the multiple color oligonucleotide tags is performed through multi-color single molecule detection.

This method can be used to determine whether an insertion, a deletion, or an amplification event has occurred in a particular nucleic acid sequence. In some embodiments, the nucleic acid sequence may be one that is at risk of such a genetic event. Accordingly, if probes are chosen that are spaced at a known distance from each other in a wild type sequence, then any change in the distance between these probes in a sample indicates that a genetic event has occurred in the sample. If the probes are closer to each other in the sample as compared to wild type, this could indicate that a deletion event has occurred. If the probes are farther from each other in the sample as compared to the wild type, this could indicate that an insertion event has occurred.

c. General Determination of the Size of a Nucleic Acid Fragment Through Fluorophore Incorporation.

Fluorophore incorporation allows the direct and proportional analysis of fluorophores on a growing strand of nucleic acid molecule. The general concept of fluorophore incorporation is that fluorophores are uniformly incorporated throughout the length of a newly synthesized nucleic acid molecule, and the resultant total fluorescence of the molecule is indicative of its length. Fluorophore incorporation can be performed during a PCR reaction, polymerase extension reactions, and used in more specific methods as determined some of the methods described below.

d. Determination of the Distances Between Two Sequences (i.e., Microsatellite Analysis, Sequence Identification, Fragment Sizing, Etc.).

Figure 14:
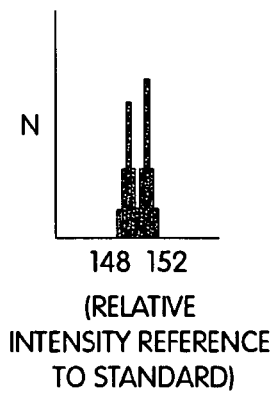
FIG. 14 is a schematic of the signal generated from a sample having heterozygous microsatellite of lengths 152 and 148 base pairs.

Another application of sizing technology is the determination of the distances between two sequences in a nucleic acid molecule. The query in this particular instance may be the size of a particular genomic segment of interest in the genome. This particular analysis is illustrated in FIG. 14, where the distance between the primer and the stopping oligonucleotide is determined through the proportional number of fluorescent nucleotides that have been incorporated into the sample. The distance between the primer and the "stopping" oligonucleotide (i.e., a sequence-specific binding agent that cannot be removed by the polymerase) is determined through the fluorescent incorporation of nucleotides into the growing chain. The proportional number of incorporated nucleotides is detected through signal intensity. The greater the distance between the primer and the stopping oligonucleotide, the brighter the integrated signal intensity.

Figure 15:
FIG. 15 is a schematic of a primer run-off reaction in which fluorescent labels are uniformly incorporated into the newly synthesized nucleic acid molecule.

One of the major uses of this method of determination of distances between points is the assaying of microsatellite markers and assessing the size variation of the various microsatellite markers in a given sample. For instance, some common microsatellite markers differ in size by several di- or tri-nucleotide repeat units. These methods of determination of the size of the repeat unit is directly assayed through the measurement of the fluorescence intensity of the particular molecules of interest. In the case of the tri-nucleotide repeat of CGACGACGA, a full incorporation of a fluorescent-dCTP into the growing chain allows intensity-based determination of the size of the microsatellite marker. This allows a rapid determination of the allele present on the sample. An individual with a heterozygous microsatellite of lengths 152 and 148 would have the readout shown in FIG. 15.

e. Determination of the Fragment Sizes Using a Primer Run-off Reaction.

Figure 16:
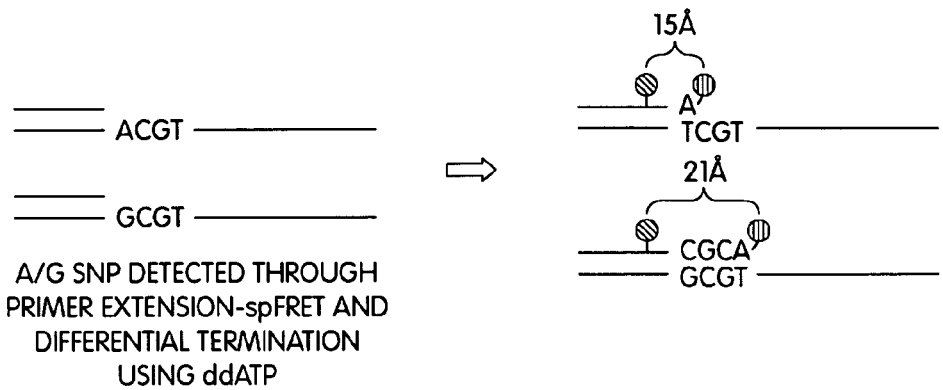
FIG. 16 is a schematic showing that detection of small distances in a nucleic acid system can be determined through the use of spFRET. An SNP-scoring method can be used that allows the determination of SNPs using primer-extension and spFRET.

Similar to assaying size between two points in a sample, the size of a fragment of DNA can also be assessed through the use of techniques such as that involved in primer extension and fluorophore incorporation. This method requires the use of a primer that resides on one end of the fragment that is being assayed. The polymerase extension and the incorporation of fluorescent nucleotides throughout the length of the DNA fragment allows the size of the molecule to be determined through analysis of the integrated intensity of the molecule. This is illustrated in FIG. 16. In the primer run-off reaction, the fluorophores are incorporated throughout the length of the DNA molecule, allowing the length of the molecule to be determined as proportional to the size of the fragment being assayed.

f. Detection of Small Distances Between Points (i.e., Small Insertions/Deletion Analysis, SNP Scoring, Etc).

Figure 17:
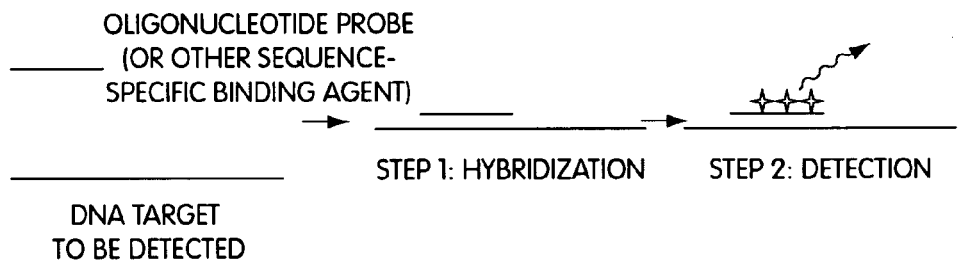
FIG. 17 is a schematic showing hybridization and detection of a probe to a nucleic acid molecule.

Distances on the order of a small number of bases can also be determined by other methods that include the use of single-pair FRET (spFRET) for the determination of small molecular distances. This ability to measure small distances on the molecular level allows for the creation of assays that rely on the measurement of small molecular distances. SpFRET is an extraordinarily powerful tool that can be leveraged into a number of different assays. FIG. 17 shows how detection of the small distances in a nucleic-acid system is determined through the use of spFRET. In this particular example, a SNP-scoring method is described that allows the determination of SNPs through the use of a primer-extension method and also spFRET. The determination of small distances in a system is useful for the creation of molecular biology and genetic assays. These methods of analysis are important for the assaying of small insertions or deletions (5–10 bases), novel assays for sequence detection, and molecular genetic analysis.

FRET has the ability to measure distances between two points separated by 10 Å to 100 Å. The angstrom resolution of FRET has been used in studies of molecular dynamics and biophysical phenomena. The resolving power of FRET arises because energy transfer between donor and acceptor fluorophores is dependent on the inverse sixth power of the distance between the probes. In practice, this resolution is about an order of magnitude better than that of the highest resolution electron microscope and with FRET, specimen preparation is much easier. Furthermore, distances determined by using FRET data compare well with those measured by X-ray crystallography. The two points of interest are labeled with different dyes, a donor and an acceptor. FRET requires that the excitation spectrum of the acceptor must overlap with the emission spectrum of the donor. In this manner, energy is transferred through resonance from the donor to the acceptor. By measuring the amount of fluorescence resonance energy transfer, it is possible to determine the distance between the two points of interest.

III. Sequence Detection.

The use of single molecule detection methods allows for the direct detection of sequences without the need for amplification. The detection of these sequences is direct and straightforward based on tagging schemes that are more optimized for this type of detection. Sequence detection can be accomplished through a variety of methods, including multi-color sequence determination, various tagging approaches, and also enzymatic methods of detection of the sequences.

The simplest case of sequence detection is the hybridization of a sequence-specific tag to the DNA of interest. This allows for the detection of the presence or absence of the particular sequence in the sample of interest. Other methods include the hybridization of a sequence-specific tag to the DNA of interest and then the extension of the primer to detect the hybridization event. A major category of single-molecule sequence detection methods is thus the detection of a hybridization event through a method compatible with single molecule detection.

a. Detection of a Hybridization Event.

Detection of a hybridization event in solution is a binary process that allows for the direct analysis and detection. This requires that the sequence detection event be a fluorescent-based signal that allows for the capture of the occurrence of the binary event.

b. Multi-color Tagging and Detection Approaches.

Figure 18:
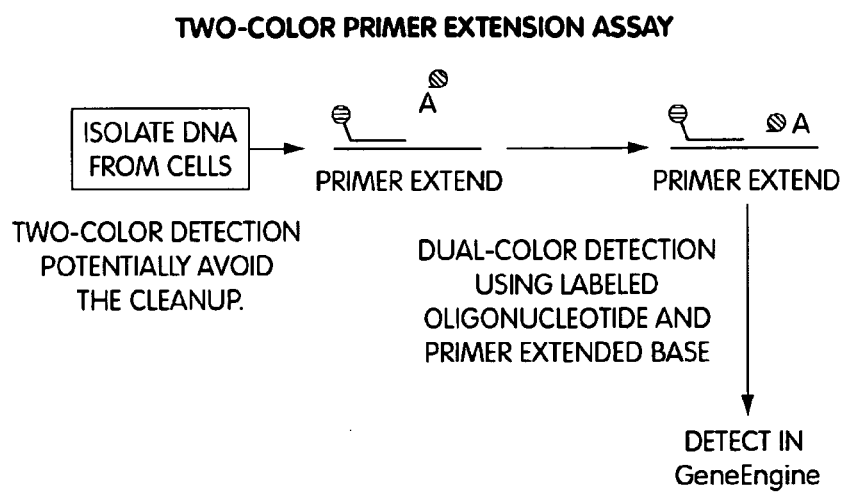
FIG. 18 is a schematic showing a two color primer extension assay.

Multi-color single molecule detection chemistries allow for more specific detection of the sequences and also allows for additional advantages of not requiring sample cleaning steps. These methods are described in the following paragraphs and illustrated in FIG. 18.

Figure 19:
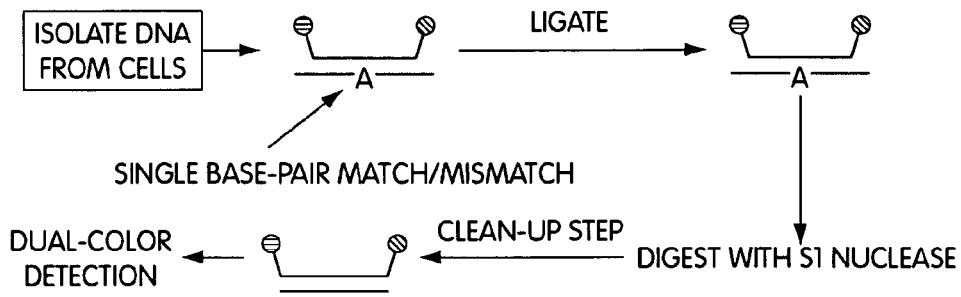
FIG. 19 is a schematic showing a two color extension and ligation assay.

The two-color primer extension assay allows the ability to avoid sample cleanup as well as increase the specificity of the detection. In this particular assay, the primer is hybridize to the sample of interest and a fluorescent nucleotide is extended to characterize the nucleic acid molecule at that particular position. This assay may be used for the detection of single nucleotide polymorphisms (SNPs) or the detection of other genetic variation in the system. (FIG. 19) Coincident color detection is discussed further in a later section.

Figure 20:
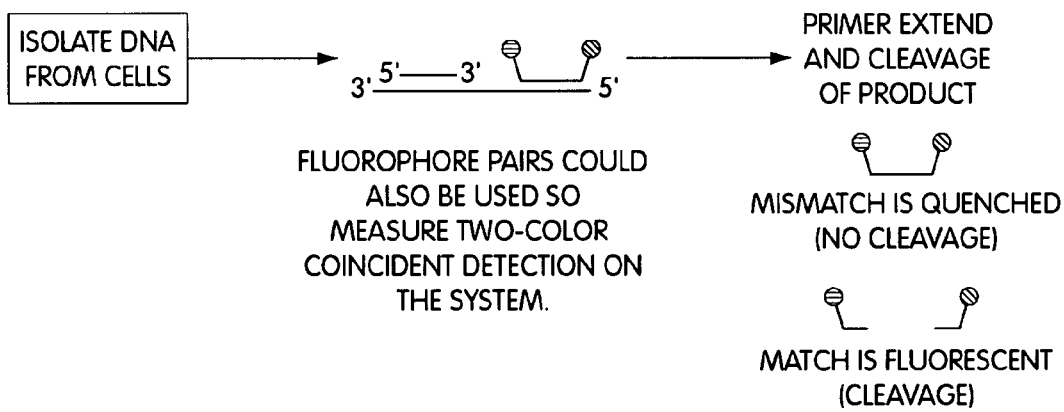
FIG. 20 is a schematic showing a spFRET based assay or primer extension assay based cleavage of product.

Sequence detection through the use of two-color ligation assays is important as well to generate the type of analysis that would be universal for sequence detection as well as polymorphism detection. Briefly, this assay consists of the hybridization of the oligonucleotides directly to the sample. The oligonucleotides are labeled each with a different fluorophore. Only a perfect match of the two oligonucleotides allow for the detection and ligation of the oligonucleotides. The dual-color labeling of the sequence allows for greater specificity of the detection as well as ease of sample cleanup. (FIG. 20.)

Figure 21:
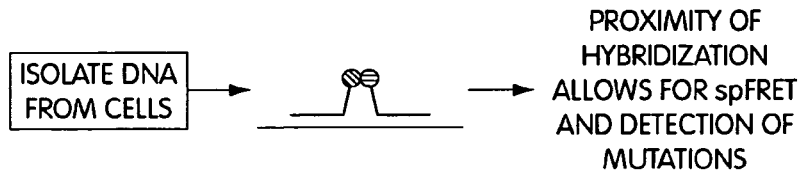
FIG. 21 is a schematic showing a spFRET based assay based on coincident hybridization.
Figure 22:
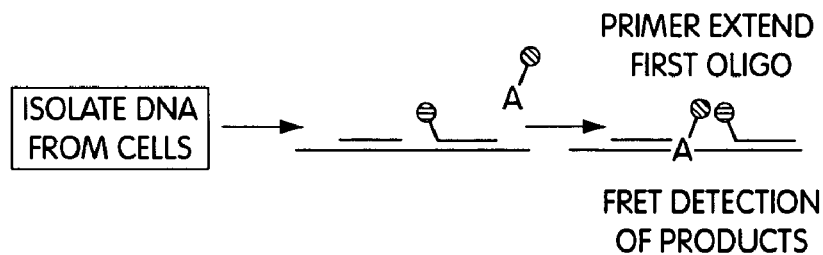
FIG. 22 is a schematic of a spFRET based assay in combination with single base extension reaction.

FIG. 21 shows single-pair FRET can further be leveraged into additional methods of analysis including more sensitive sequence detection methods such as cleavage of sequence recognition probes in a direct genomic assay. In this schematic, the target DNA is hybridized with two oligonucleotides, a primer and a sequence detection probe. The primer allows for polymerase extension. The sequence detection probe has a reporter fluorophore and a quencher fluorophore on it. The quencher fluorophore quenches the fluorescence of the reporter fluorophore when the two are in close proximity to each other due to radiation-less energy transfer. The extension of the primer through the use of polymerase extension allows for the nicking and degradation of the reporter oligonucleotide if the reporter is downstream at the proper distance from the primer oligonucleotide. This analysis is similar to the TaqMan reaction (Applera Corporation) without the need for a cumbersome PCR step. The analysis method is more straightforward, robust, and allows for the direct detection of target nucleic acid molecules without the prior need for amplification. The ability to detect single molecules overcomes the need for prior amplification and ensures that the sequence information retrieved is inherent in the target and not a amplification artifact. The real-time readout of single molecule detection also allows for an extremely rapid readout (minutes as opposed to hours), thereby increasing the productivity and throughput of an ordinary laboratory. (FIG. 22.)

Simple and straightforward methods of spFRET also lead to the rapid ability to detect sequences in target nucleic acid molecules. Two oligonucleotides with sequences that are close to one another with fluorophores that can undergo fluorescence resonance energy transfer allows the detection of sequences with high fidelity because of the dual recognition step from the two oligonucleotides in the target DNA. The two oligonucleotides are labeled respectively with FRET pairs, such as tetramethylrhodamine and Cy5. The hybridization of the two oligonucleotides allow for the direct detection of the sequences through the measurement of the efficiency of fluorescence resonance energy transfer between the two oligonucleotides. Furthermore, through the choice of the proper fluorophores with the correct Forster distance (the distance defined as half maximal efficiency of energy transfer), an accurate assessment of the distance between the two probes is possible, thus allowing a detailed analysis of the sequence that is recognized through the use of the oligonucleotide. This analysis allows for the direct assessment with high sensitivity and specificity the presence of certain nucleic acid specific features in the sample. (FIG. 23)

The extension of spFRET can further be coupled to additional sequence discrimination steps such as primer extension, ligation, etc. and then detection of spFRET through the detection of fluorescence from the molecules. The method of spFRET shown in the above illustration depicts the detection of a particular polymorphism through the use of a primer extended fluorophore. The fluorophore that is extended is then capable of fluorescence resonance energy transfer with the adjacent oligonucleotide and hence allows the direct detection and analysis of the polymorphism of interest in the sample. The extension step adds additional sensitivity and specificity to the analysis of the DNA target.

Figure 23:
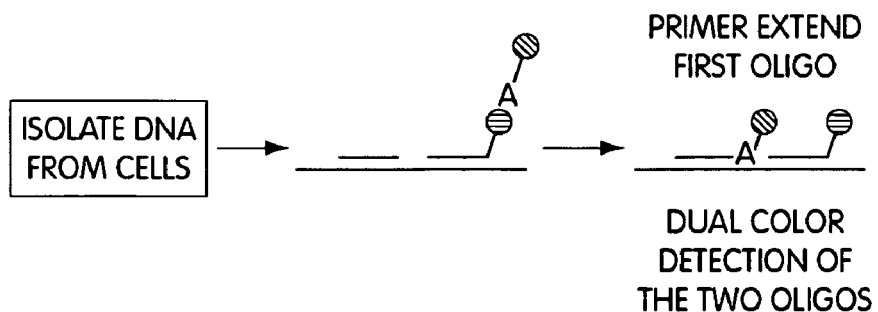
FIG. 23 is a schematic of a two-color detection assay in combination with primer extension.
Figure 24:
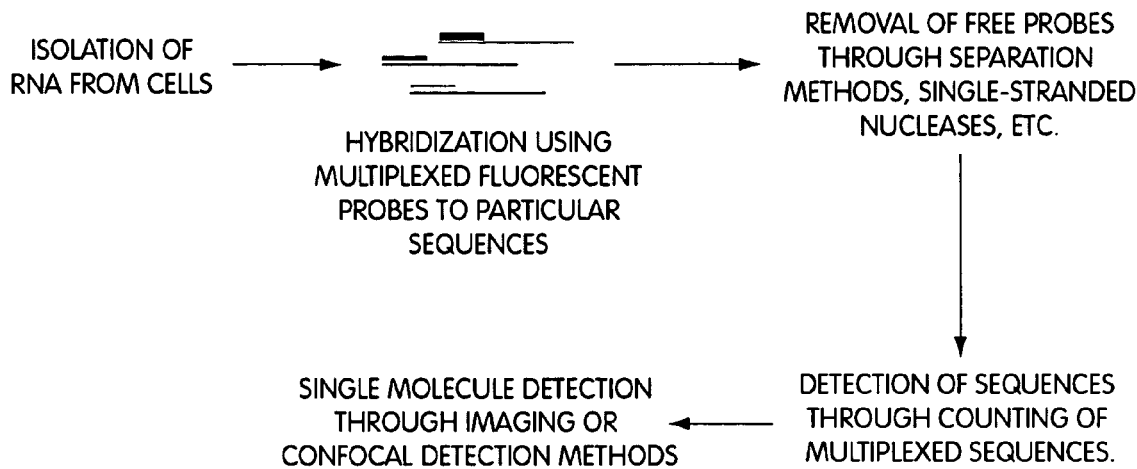
FIG. 24 is a schematic showing detection of single nucleic acid molecules from one or few cells.
Figure 25:
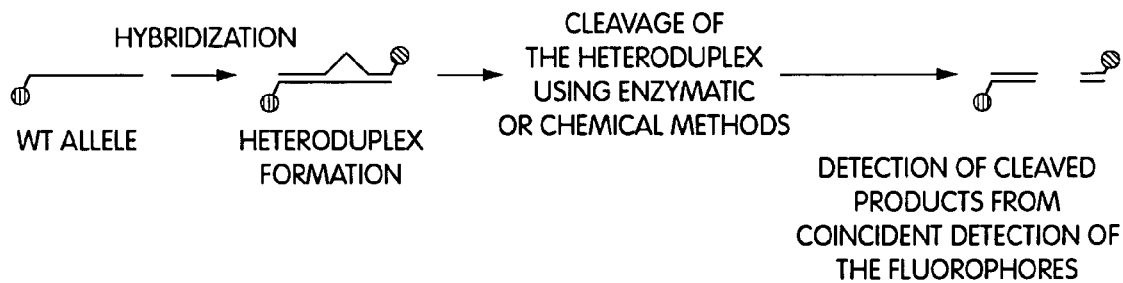
FIG. 25 is a schematic showing the detection of a polymorphism or mutation in a nucleic acid molecule.
Figure 26:
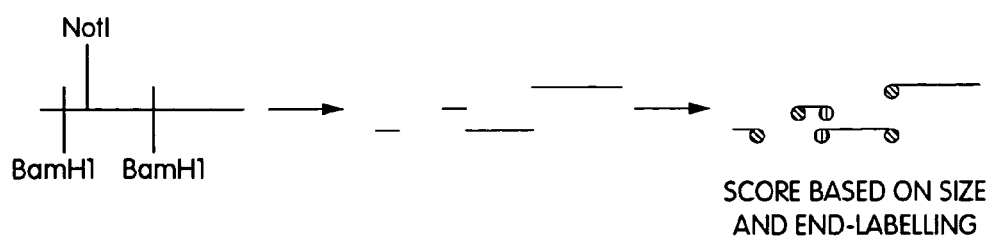
FIG. 26 is a schematic showing the use of a single molecule counter for the analysis and fingerprinting of unknown DNA fragments.

Two-color, non-spFRET detection also allows for the determination of the presence or absence of particular sequences with high sensitivity and specificity as illustrated in the FIG. 23.

IV. Single Molecule Gene Expression Methods.

The novel ability to determine the presence of single sequences allows for direct analysis of single molecule gene expression. The novel aspect here is the combination of detection and tagging aspects for the determination of gene expression. The determination of gene expression through single molecule methods is highly unique. The following illustrates the process flow for the determination of single molecule gene expression.

In the case of single molecule RNA expression detection, the RNA is isolated from a cell (e.g., single cell expression analysis), and tagged using multiplexed fluorescent tagging methods. The methods for multiplexed fluorescent tagging includes the ability to determine the presence of the tag through the use of sequences that have different colors on them. The multiplexing of these multiple colors include having the ability to tag different sequences with different colors, different combinations of fluorophores, different intensities, fluorophores with different lifetimes, and fluorescence resonance energy transfer (FRET) fluorophores. Furthermore, unique tagging schemes can be created to allow for the detection of unique sequences in the same. These schemes include the use of combinations of non-unique probes (i.e. 6–8 basepairs) that are each labeled with a different color fluorophore. Various combinations of 10 such probes allows for many combinations that would uniquely identify the sequence of the expressed transcript. In addition to combinatorial methods to tag the DNA molecules, the other methods that include the ability to find and identify the expressed sequences in a particular sample include the ability to (1) linearize DNA, and (2) to read patterns on the RNA molecules based on the pattern of the signals arising from the sample as described in U.S. Pat. No. 6,355,420 B1, issued Mar. 12, 2002. With these methods of tagging the native (non-amplified) RNA molecules, this opens up new areas that allow for extremely accurate, highly quantitative methods of RNA gene expression analysis. In addition to the tagging of the DNA molecules, various methods to allow for the clean-up of the DNA molecules include the use of molecular separation methods (i.e. spin columns, bead separation), single-stranded digestion and separation methods, and dialysis methods.

a. Mutation/polymorphism Deleclion.

In addition to the methods of DNA detection described in the above areas, other methods that employ single molecule detection use single molecule detection coupled with chemistries that yield the detection of mutations and polymorphisms. One particular area that is important to the readout of the technology is the ability to read out mutation detection products that arise from a number of tagging, nucleic acid manipulation, and chemical alterations of the DNA molecules.

Detection of mutation and polymorphisms through the use of cleavage-based methods of analysis. Methods to detect mutations include hybridization and cleavage of products that allow for the determination of the particular mutation in a given system. This ability to determine the mutation or the polymorphism involves the creation and cleavage of heteroduplexes. In a general schema, the detection of the polymorphism or mutation is performed as follows:

The ability to perform single molecule detection on cleavage products provides for excellent readout advantages over other detection methods. In current methods of analysis, the heteroduplex analysis requires a readout using gel electrophoresis, but through the use of single molecule detection, the readout of the cleavage products is through direct analysis that requires data capture of less than several seconds. Methods to generate products that rely on cleavage are known in the art. Some examples include the PCR amplification of the region containing the polymorphism or mutation of interest (incl. Insertion/deletions) with primers of two different colors. These products are then amplified using these primers. The products are then denatured and rehybridized, either to each other, or to the normal product. The cleavage of the products is then performed using endonuclease VII, RNase (if the product is hybridized to RNA), or chemical methods (osmodium tetroxide, etc.).

The use of primer extension with direct single molecule detection has not been demonstrated. Primer extension, or minisequencing, has been demonstrated in the art to be able to quickly and accurately discriminate between different polymorphisms. These methods of analysis are important for being able to discriminate single molecule polymorphisms and other important features unique to DNA-based detection. The rapid readout of primer extension products through the use of single molecule detection methods make it an ideal method of readout.

b. Direct Detection of Methylation Sites in the Genome.

The ability to directly detect DNA also allows for the direct detection of methylated sites in the genome, important for the study of epigenetics, especially the role of methylation in the determination of where genes are turned on and off in the genome. Typically, the analysis of methylation patterns on a strand of native DNA is not directly possible and is assayed using indirect methods of analysis that include the use of bisulfite to deaminate the methylated cytosines, converting them to uracils. Upon PCR amplification, the uracils are then effectively synthesized with the complementary adenosine. This synthesis thus allows for analysis of the methylated sites then via sequencing or hybridization-based approaches to determine the locations of the methylated sites on the strand of DNA.

Analysis using single molecule detection, however, allows the direct interrogation of structural motifs on a strand of native DNA. This direct analysis allows the query of methylation sites on a strand of DNA directly and thus informs, through single molecule detection, the presence or absence of methylated sites on a strand of native DNA. The recognition of methylated sites on a strand of native DNA can be accomplished through a number of different methods that involve direct fluorescent tagging of the different sites on a strand of DNA. These methods include the use of well-characterized methyl binding domains (MBDs) that recognize 5-methylcytosines for the direct detection of methylated sites in the genome. Other methods that allow direct recognition of the sites of interest also include methods of altering methylation analogues and placing at methylation sites a fluorophore instead of a methyl-group. These methods are well known in the art. Subtraction methods of analysis that include demethylation/methylation techniques also allow for the rapid analysis of methylated sites in the genome.

c. Direct Fingerprint Analysis of Fragments Using Combinations of Tagging Techniques.

A general category of fragment identification uses combinations of the tagging methods described in this patent application and sophisticated data analysis that allows the determination of the DNA fragment that is placed through the system. This section describes only a subset of approaches that describe the ability to fingerprint fragments of DNA using single molecule analysis.

One of the methods of analysis involves combining methods of DNA sizing with site-specific tagging of DNA. For instance, the fingerprinting of a bacterial artificial chromosome (BAC), may be accomplished through (1) cutting with two restriction endonucleases, (2) differential end-labeling of the digested fragments with different colors, (3) running the fragments through the single molecule counter, and (4) determining the size of the molecules and the differentially-labeled end tags. This level of information allows the rapid determination of the content of the DNA in the system. In this case, it is the fingerprinting of BACs or other fragments of DNA that are of interest. The following is an illustration of the ability to use the single molecule counter for the analysis and fingerprinting of unknown DNA fragments.

The sample is digested using two enzymes and then end-labeled using polymerase extension to yield differential products. The products are then sized and scored through the use of the single molecule counter and fluorescence analysis. The products are then further subdivided to yield the end-labeling identity of each of the products. This type of analysis can yield a high information content analysis of the target DNA molecule and lead to the direct analysis of the molecules of interest to tell its identity and base-pair composition. Variations on the cleavage and labeling analysis can be conceived where two reactions of the same sample are utilized to identify the molecule of interest. These include performing one digestion and end-labeling reaction first. In a second reaction, the same sample is subject to two digestions and the end-labeling reaction. The combination of these two reactions allow for the rapid analysis and fingerprinting of the system. The rapid identification of the molecules through single-molecule analysis allows an instantaneous identification which provides a readout of several seconds, in contrast to running conventional agarose gels which take at least thirty minutes.

A variety of techniques can be conceived that use enzymatic and labeling techniques in combination thereby facilitating identification and recognition of a nucleic acid molecule.

Combinations of these reactions can be performed on the same sample in two different reactions or on the same sample in succession. The possibilities are large and thus allows a rapid analysis of all the fragments in a given mixture with ease and speed.

d. Single Molecule Readout Methods.

Single molecule readout methods pertain to two distinct areas, (1) fluorescence-based single molecule methods and (2) non-fluorescence-based single molecule detection methods. In the case of fluorescence single molecule detection methods, these fall into those requiring the use of point detectors (i.e. APDs and photomultiplier tubes) and those requiring the use of imaging detectors.

V. Direct Nucleic Acid Molecule Analysis.

The foregoing methods can employ a DirectRNA™ platform that includes a microfluidics and lithography design. The platform is flexible and compatible with a wide range of sample types and assays. It provides for single molecule detection and can analyze samples that are on the order of nanoliters. It is to be understood that the following methods are equally applicable to various types of nucleic acid molecules including DNA and RNA molecules.

a. Coincidence Counting.

Figure 27:
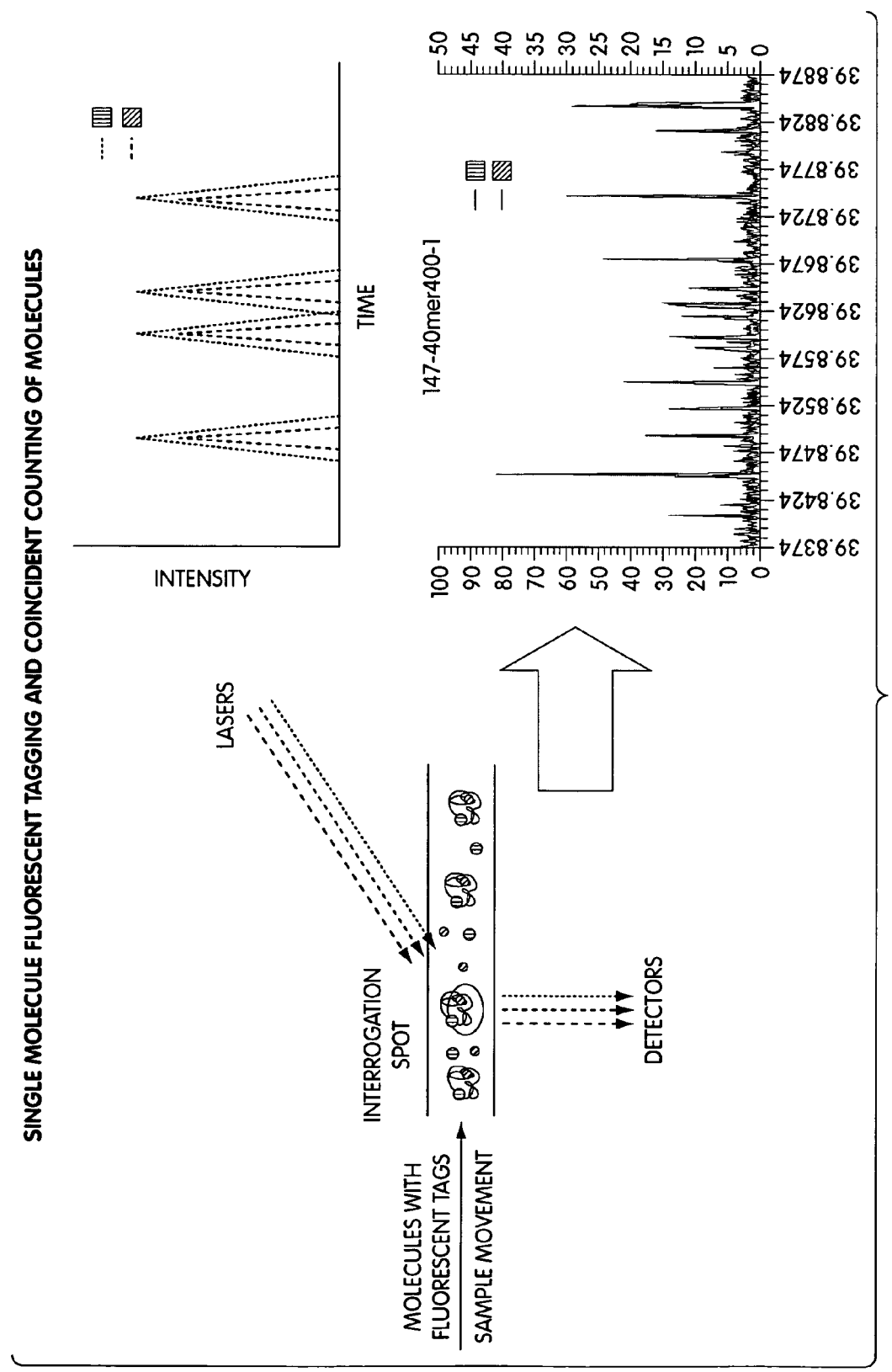
FIG. 27 is a schematic diagram of single molecule fluorescent tagging and coincident counting of molecules.

As discussed above, the methods of the invention can be used to detect and quantitate individual nucleic acid molecules such as RNA molecules. Coincident detection allows nucleic acid molecules (such as RNA molecules) to be distinguished from unbound probes, as shown in FIG. 27.

It also allows target molecules that are bound by two probes to be distinguished from those bound by only one probe (where a two probe binding event is a desired). It can be further used to distinguish mismatch-containing hybrids between target molecules and dual labeled probes from perfectly formed hybrids (i.e., without mismatch).

RNA targets can be labeled with detectable molecules either by hybridization (in some instances preferred for samples harvested from in vivo sources) or incorporation of fluorescent labeled nucleotides by reverse transcription. This latter labeling method can be used to prepare RNA samples for optimizing a system, although it is not so limited.

Two color coincident detection was used to minimize non-specific background signals, thereby achieving a higher signal to noise ratio than was previously attainable. The ability to distinguish between bound and unbound probes using the detection system alone means that there is no need for a prior column purification step to remove unincorporated probe. Target molecules were detected by subtracting random coincident from total coincident peaks. The method provides for ultra-rapid detection on the order of 20–20,000 molecules typically detected in one minute.

Coincident detection can also take the form of coincident binding events even without the detection of two or more colors. In these embodiments, the binding events can be of two unit specific markers, one of which is attached to a donor FRET fluorophore and the other of which is attached to an acceptor FRET fluorophore. Upon proximal binding of the unit specific markers to a target molecule and excitation of the donor fluorophore, emission of the acceptor will be observed without its direct excitation by its corresponding excitation laser. "Proximal binding" refers to the distance between binding of the unit specific markers sufficient to ensure that energy transfer can take place between the donor and acceptor fluorophores of the FRET pair.

Coincident detection can also take the form of proximal localization of donor and acceptor FRET fluorophores following probe extension. That is, a target molecule can be hybridized to a unit specific marker which is attached to either a FRET fluorophore. A new nucleic acid molecule is then synthesized extending from the unit specific marker. The newly synthesized nucleic acid molecule will incorporate nucleotides that are labeled with the alternate FRET fluorophore. That is, if the FRET fluorophore attached to the unit specific marker is a donor FRET fluorophore, then the incorporated FRET fluorophore is an acceptor, and vice versa. In still another variation, the incorporated fluorophores can be a mixture of donor and acceptor fluorophores, and incorporation of a plurality of each (provided at proximal distances to each other) will result in a stronger intensity signal.

b. System Performance of DirectRNA™ Technology.

Figure 28:
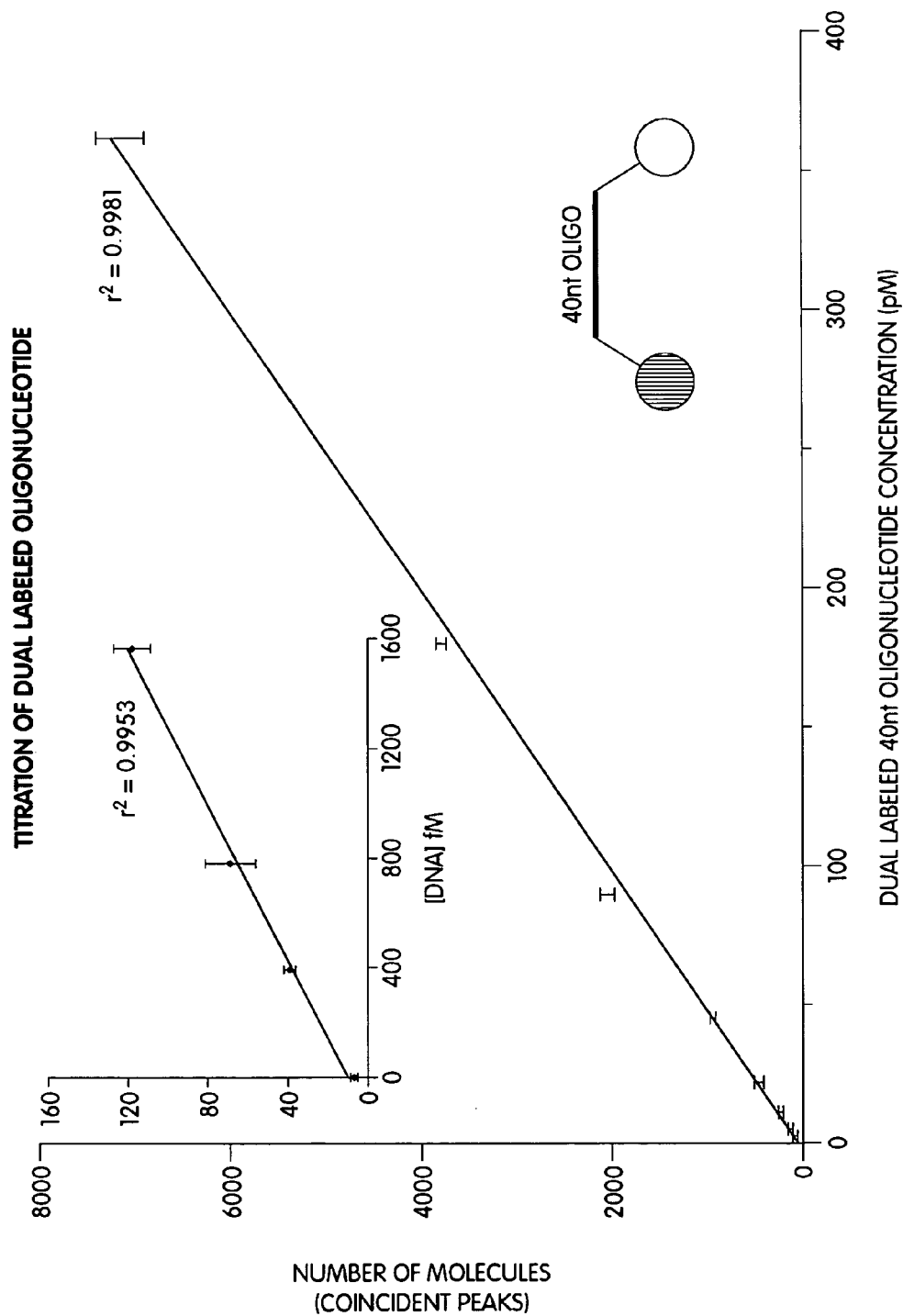
FIG. 28 is a graph showing titration of a dual labeled 40 nucleotide oligonucleotide.
Figure 29:
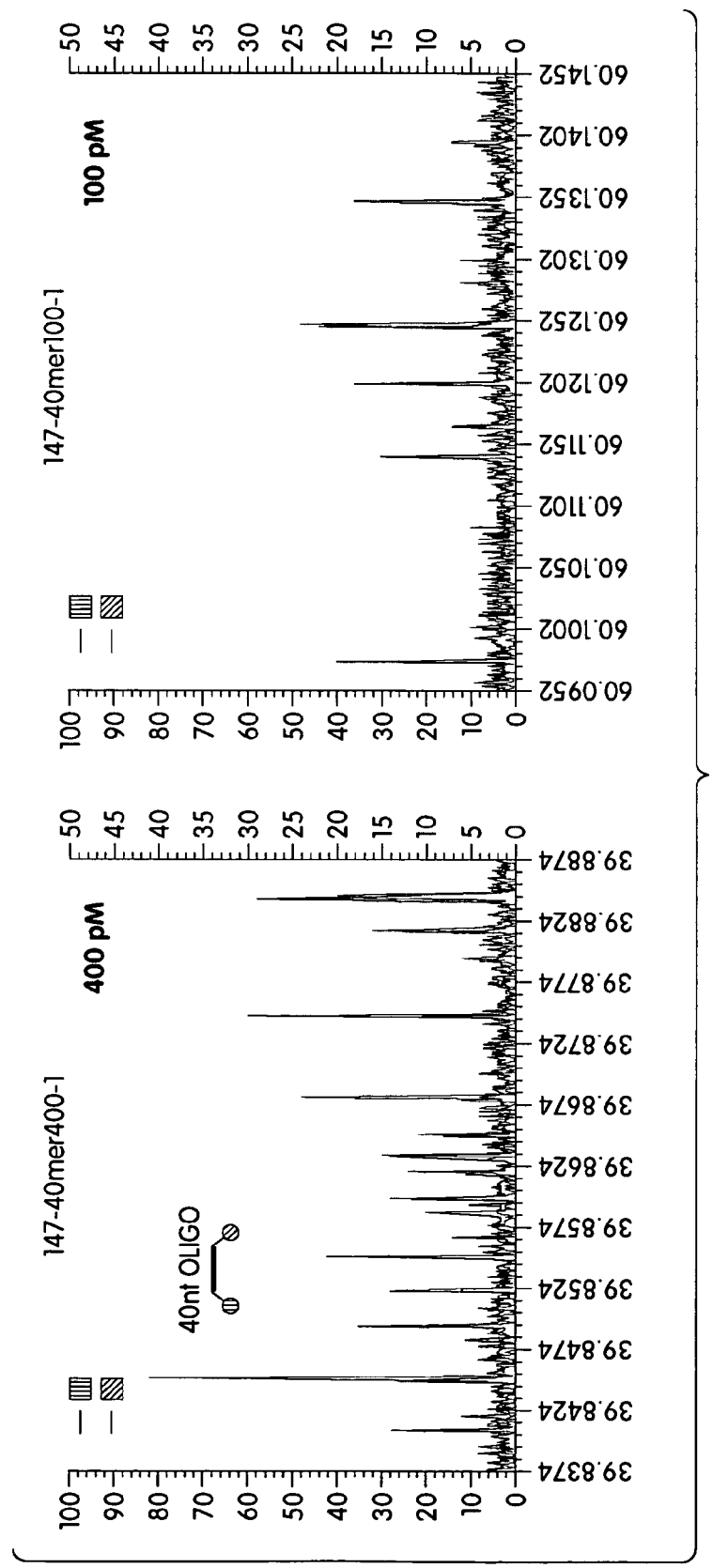
FIG. 29 is a series of plots for different concentrations of oligonucleotide (corresponding to FIG. 28).
Figure 29:
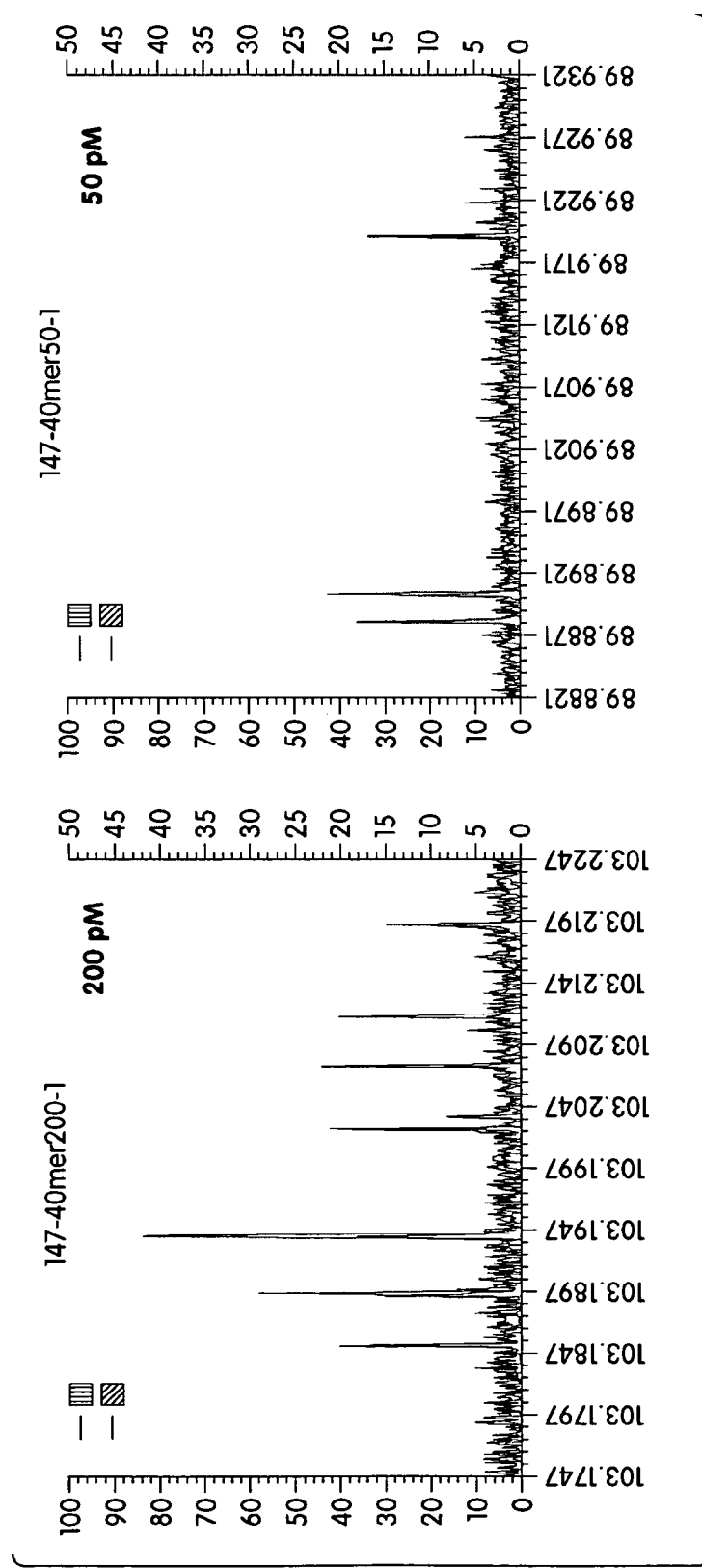

FIG. 28 illustrates detection of a dual labeled oligonucleotide. A 40 nucleotide nucleic acid molecule was labeled at its 3' end with TAMRA and at its 5' end with Cy5. The loading sample volume was less than 0.5 nanoliters. As shown in FIG. 28, the detection response is linear over 3+ orders of magnitude. The inset shows that the method also works at oligonucleotide concentrations on the fentomolar (fM) order (i.e., less than 10 molecules). The method is also highly reproducible with a CV of less than 10%. FIG. 29 shows screen capture of 50 milli-second data from selected samples from FIG. 28.

c. High Specificity and Sensitivity Assays for Single Target Molecules.

Two of several assays were then validated. The design of these assays is shown in FIG. 30. These assays are the dual probe hybridization and probe extension assays. In both cases, sense and antisense RNA templates of two *E. coli* genes (spike 1 of 750 bp and spike 8 of 2 kb) as well as β-Actin (1.8 kb) and lamin A/C (1.1 kb) genes were expressed and used as models to validate DirectRNA™ assays and technologies.

Figure 31:
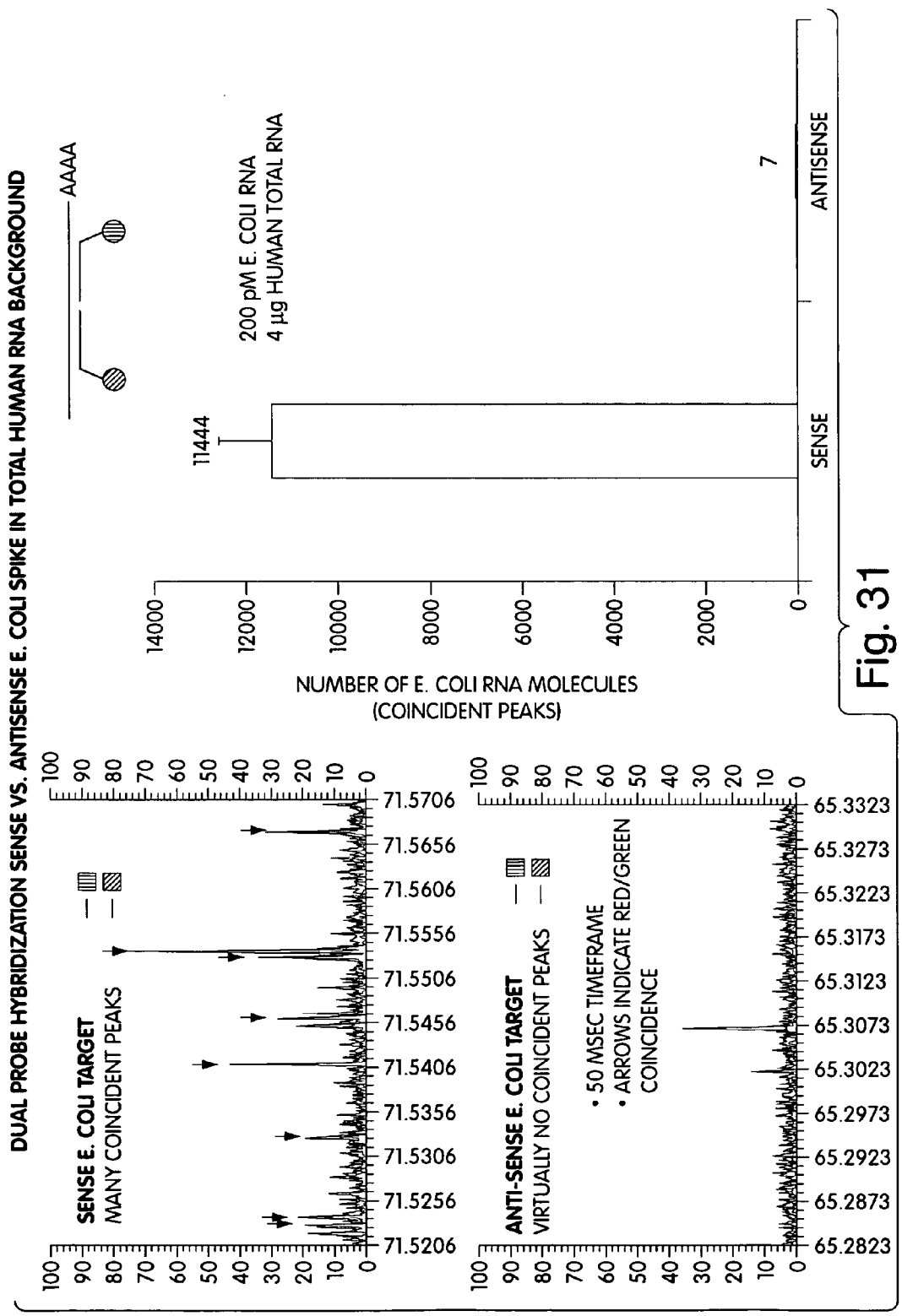
FIG. 31 shows data derived from the dual probe hybridization assay using total human RNA that is spiked with sense or antisense E. coli RNA.

With the dual probe hybridization assay, 4 μg total human RNA from Hela S3 cells were mixed with *E. coli* RNA sense or antisense template and two *E. coli* oligonucleotides (one labeled with Cy5 and the other labeled with TAMRA) in hybridization buffer in a 20 μl total volume. The mixture was denatured at 70° C. for 10 minutes and hybridized at 55° C. for 1 hour. The sample was purified by size-exclusion column and eluted in 20 μl 10 mM Tris buffer. *E. coli* RNA template was present at a concentration of 200 pM and *E. coli* probes were present at a concentration of 1 nM each in the final solution. Each sample was then analyzed on DirectRNA™ platform for two minutes. The assay is very specific for sense *E. coli* spike in total RNA background as shown in FIG. 31. It was further demonstrated that the column purification step can be eliminated using coincident detection without sacrificing high specificity and sensitivity (comparison data not shown).

Figure 32:
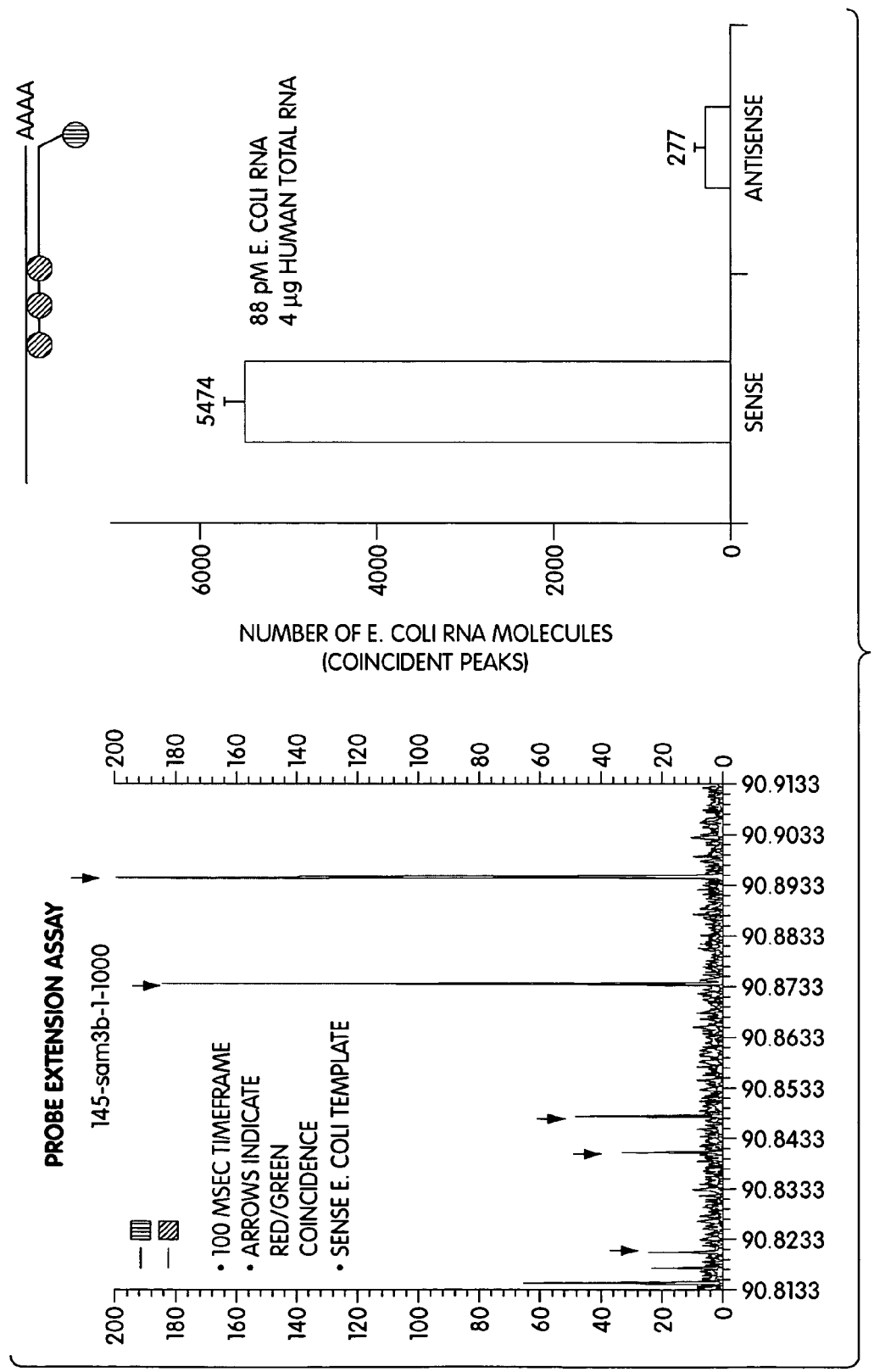
FIG. 32 shows data derived from the probe extension assay using total human RNA that is spiked with sense or antisense E. coli RNA.

With the probe extension assay, 4 μg human total RNA from Hela S3 cells were mixed with *E. coli* sense or antisense template and one *E. coli* oligonucleotide (labeled with Cy5 at 5' end) in a 20 μl total volume. The mixture was denatured at 70° C. for 10 minutes and hybridized at 55° C. for 2 hours. Then reverse transcriptase and a dNTP mixture including TAMRA-labeled dCTP were added to the mixture which was then incubated at 42° C. for 2 hours. The sample was purified by size-exclusion column and eluted in 30 μl 10 mM Tris buffer. *E. coli* RNA template was present at a concentration of 88 pM in the final solution. The assay proved specific for sense *E. coli* spike in total RNA background as shown in FIG. 32. The label at the 5' end is specific for sense RNA. Reverse transcription incorporates labeled nucleotides along the length of the newly synthesized nucleic acid molecule. FIG. 32 further illustrates the large signal to noise ratio attainable with this approach. Similar multi-color reactions and detection schemes were used to detect endogenous β-Actin in total human RNA with different amounts of spiked *E. coli* RNA (data not shown).

The probe extension assay also provides a means for determining the integrity of the nucleic acid sample. This is particularly important for RNA samples given the fragility of RNA. The method is dependent upon the relationship between the length of a template target RNA molecule (i.e., the single nucleic acid molecule of the claims) and the signal intensity of a nucleic acid molecule synthesized from a primer (e.g., a unit specific marker) and complementary to the target RNA molecule. That is, the longer the template RNA, the more labeled nucleotides will be incorporated into the newly synthesized nucleic acid, and thus the stronger the signal from that newly synthesized strand. Short RNA templates will only yield short complementary strands and therefore the possibility of labeled nucleotide incorporation is limited and the resulting signal will have a smaller intensity than would a longer strand.

Figure 33:
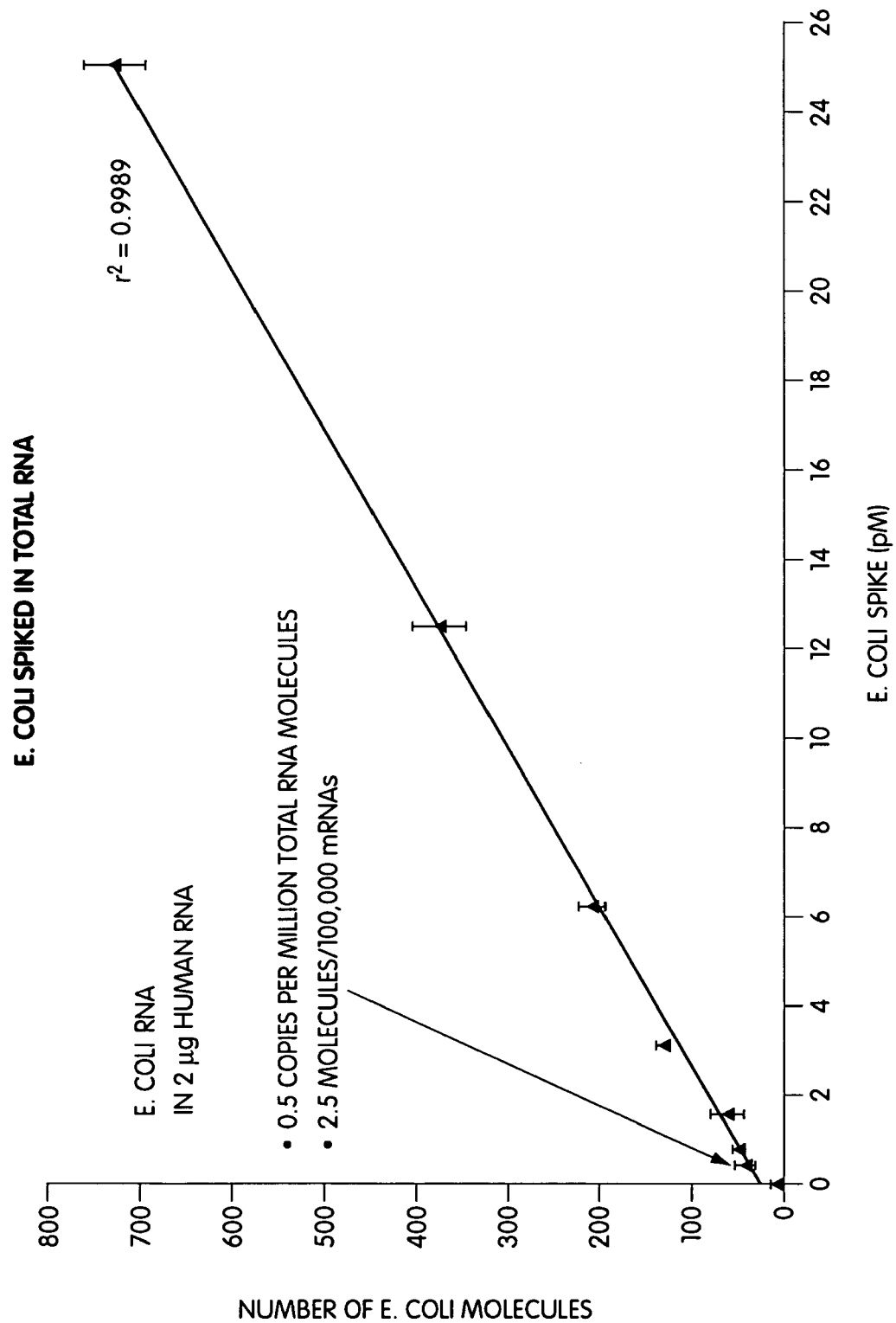
FIG. 33 is a graph showing the linear relationship between detection of E. coli RNA molecules as a function of the amount of E. coli RNA spiked into a human RNA population.

Using the dual probe hybridization assay, *E. coli* spike 1 was titrated from 400 pM to 400 fM in 2 μg total human RNA. The assay demonstrates linearity over at least 3 orders of magnitude, as well as high reproducibility (i.e., CV <10%) and very high sensitivity in a complex total human RNA background. Titration of *E. coli* template in 2 μg total human RNA from 25 pM to 400 fM is shown in FIG. 33. As shown in Table 1, 0.5 copies per million total RNA molecules or 2.5 molecules per 100,000 mRNAs were detected, demonstrating that DirectRNA™ technology can detect low copy genes reliably.

Figure 34:
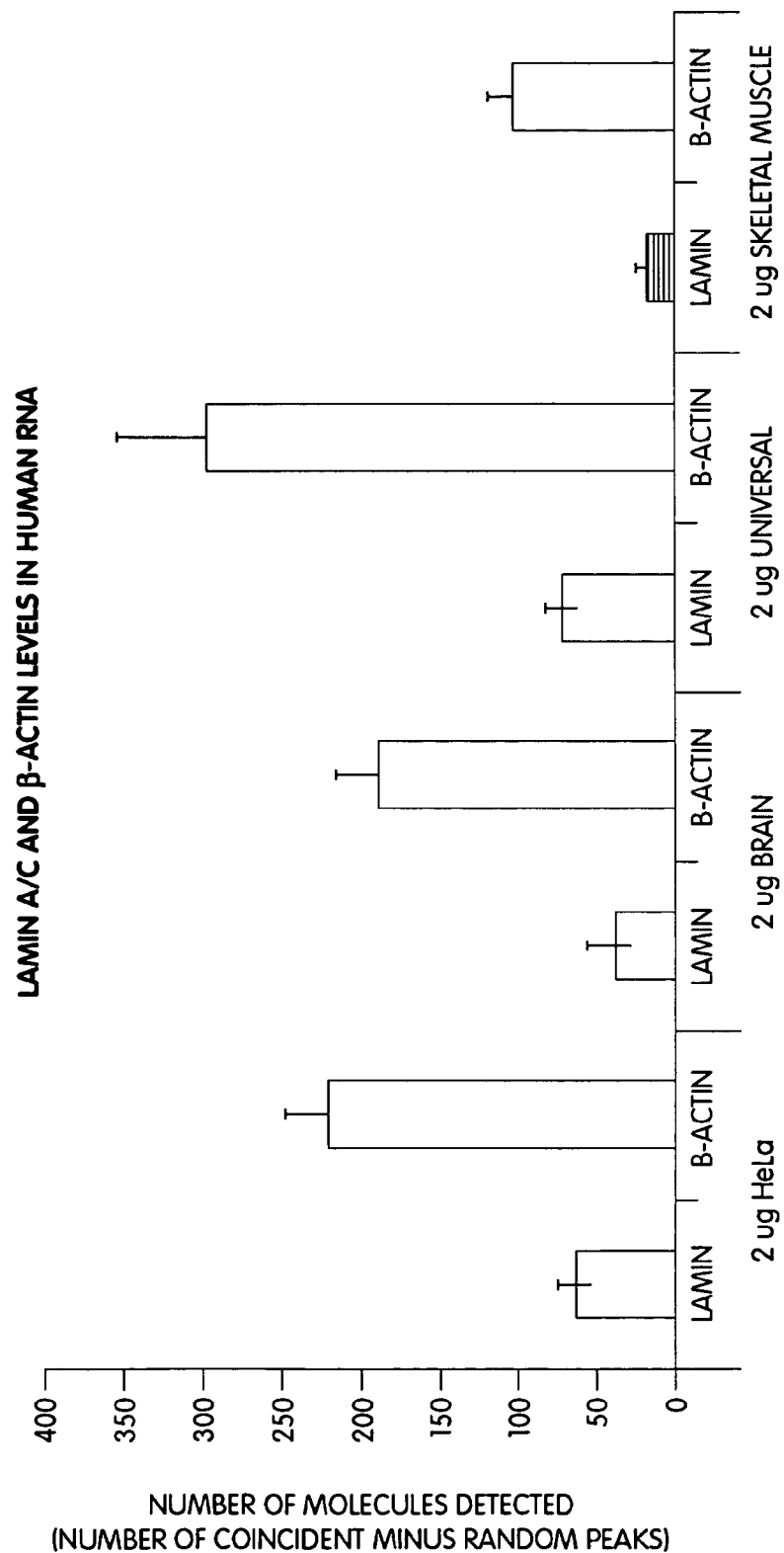
FIG. 34 is a series of bar graphs showing quantitation of lamin A/C and β-actin transcripts in a human RNA sample in various tissues and one cell line.

The assays were used to quantitate the levels of lamin A/C and β-Actin transcripts in 2 μg total RNA from different tissues and cells. The results are shown in FIG. 34. In all cases, less than a nanoliter volume from a 30 μl source was used.

TABLE 1

DirectRNA ™ Analysis-Current Sensitivity*

| mRNA Abundance | Copies/Cell | Copies/$10^5$ transcripts |
|---|---|---|
| high | 15,000 | 5,000 |
| medium | 150 | 50 |
| low | 3 | 1 |
| USG-low | 3–10 | 1–3 |

*Assuming 300,000 transcripts per cell.

d. Quantitation of Poly (A)+ RNA Level and Quality.

Figure 35:
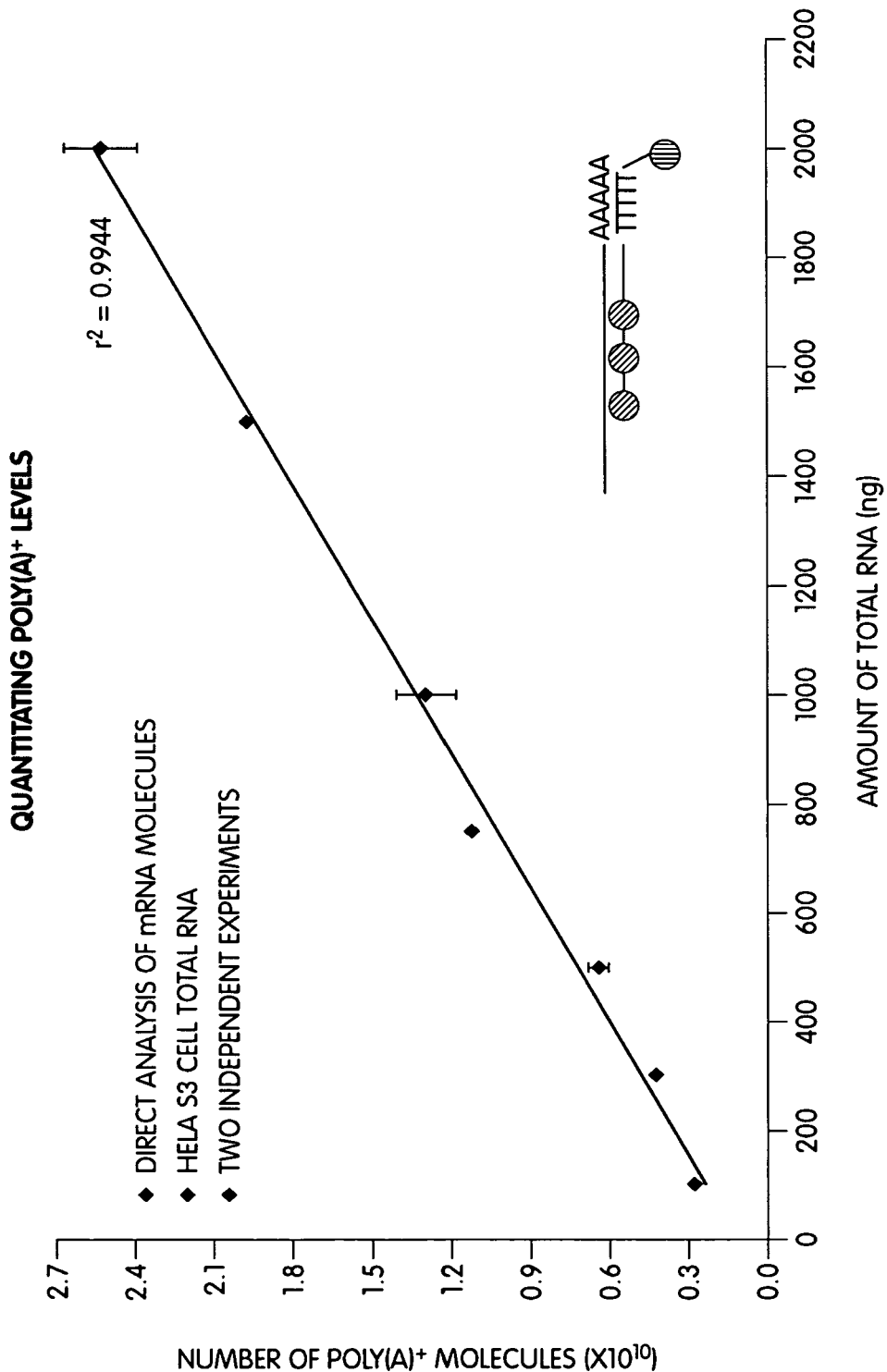
FIG. 35 is a graph showing the linear relationship between the number of poly(A)+molecules as a function of initial RNA sample from HeLa S3 cells. The data is representative of two independent experiments.

The number of poly(A)$^+$ RNA molecules in total RNA or mRNA samples was measured by incorporating TAMRA labeled dNTP into reverse transcription products from a poly(T) primer labeled with Cy5 at its 5' end. The results shown in FIG. 35 demonstrate that the assay is linear, reproducible and can be performed with a small starting RNA sample. 1.4% of total human RNA molecules from Hela S3 cells were detected as poly(A)$^+$ RNA. Published literature has reported that 1 to 2% of total human RNA should be poly(A)$^+$ RNA. The number of poly(A)$^+$ RNA molecules in total RNA or mRNA samples provides normalization standards (i.e., the number of target molecules per mRNA molecules).

Figure 36:
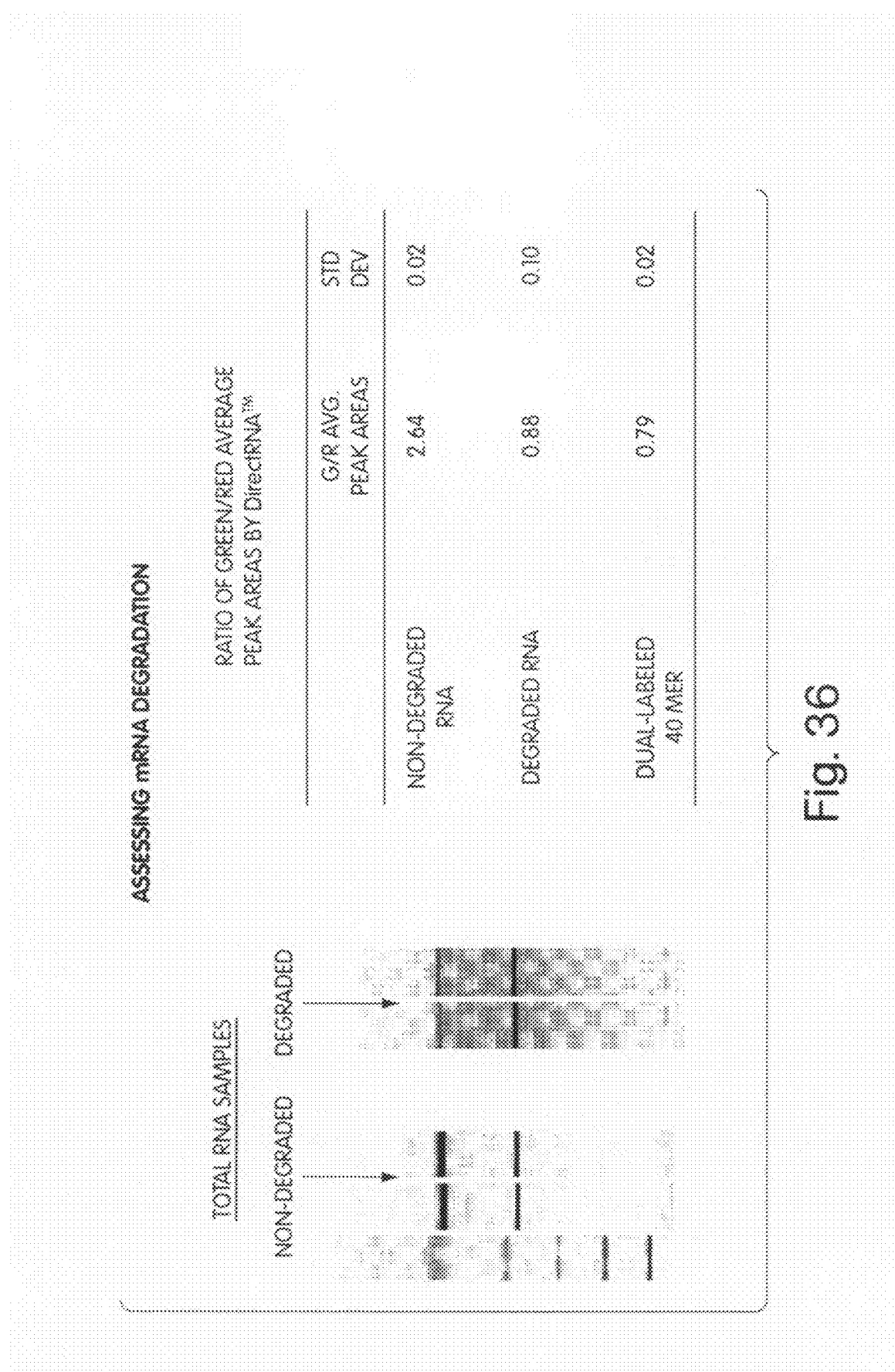
FIG. 36 shows gel electrophoresis results comparing a degraded versus a non-degraded RNA sample (on the left) and the ratio of green/red peak areas as measured using DirectRNA™ for both samples as well as for a control dual labeled 40 mer.

The assay can be used to determine the quality of harvested RNA. To be useful for further analysis, the RNA sample should be comprised of mostly intact and full length RNA molecules. The assay can test the quality of poly(A)$^+$ RNA by determining the number of fluorophores incorporated into reverse extension products synthesized using the RNA sample as a template. A higher quality RNA sample will give rise to longer and more highly labeled reverse transcription products. Reverse transcription products that are poorly labeled are indicative of degraded RNA samples. FIG. 36 further demonstrates that the ratio of incorporated green to red average peak areas from our poly(A)$^+$ assay indicate mRNA quality.

e. Comparison with RT-PCR.

Figure 37:
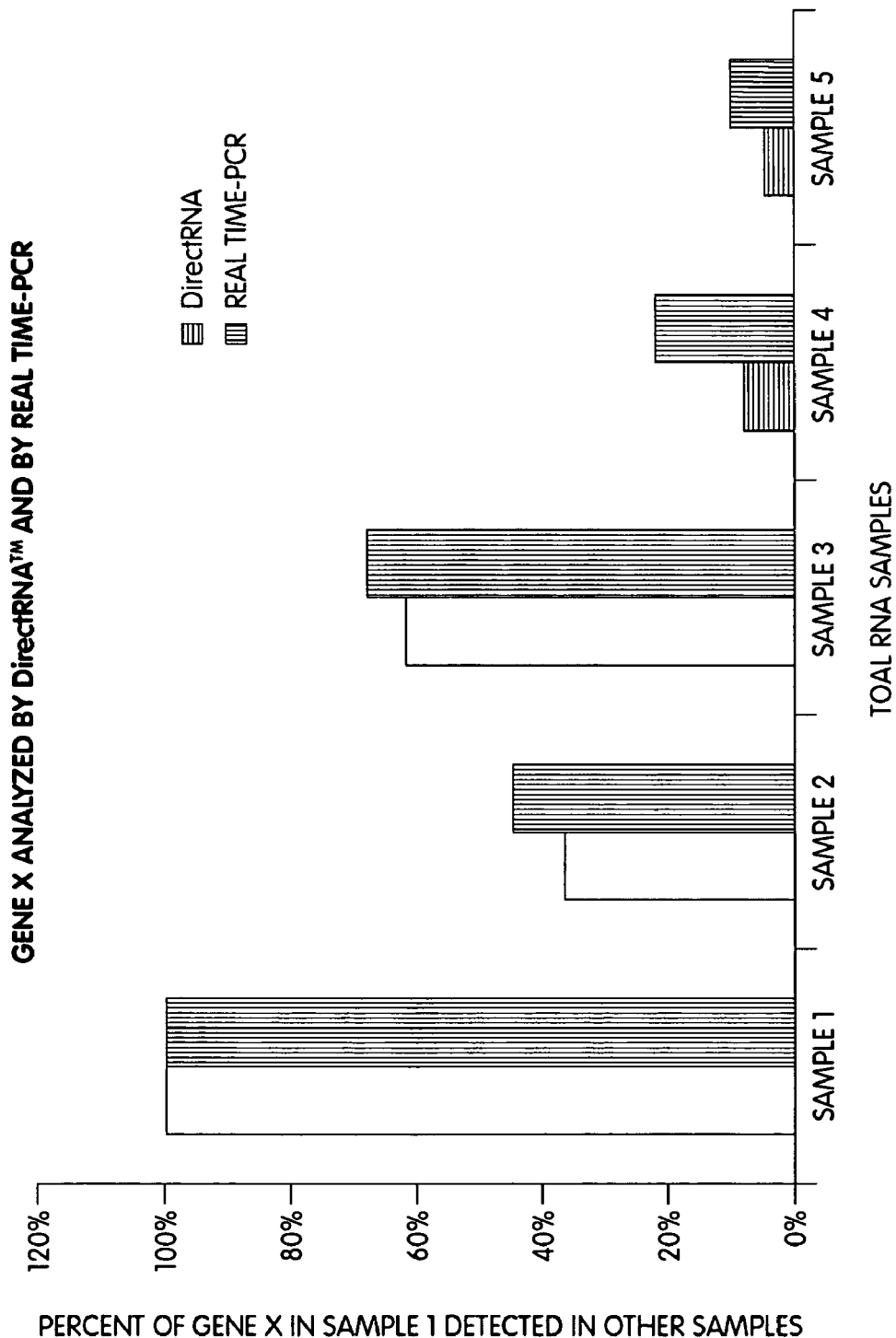
FIG. 37 is a series of bar graphs showing the results of detection of a particular transcript using DirectRNA™ (left bar of each pair) and real time PCR (right bar of each pair).
Figure 38:
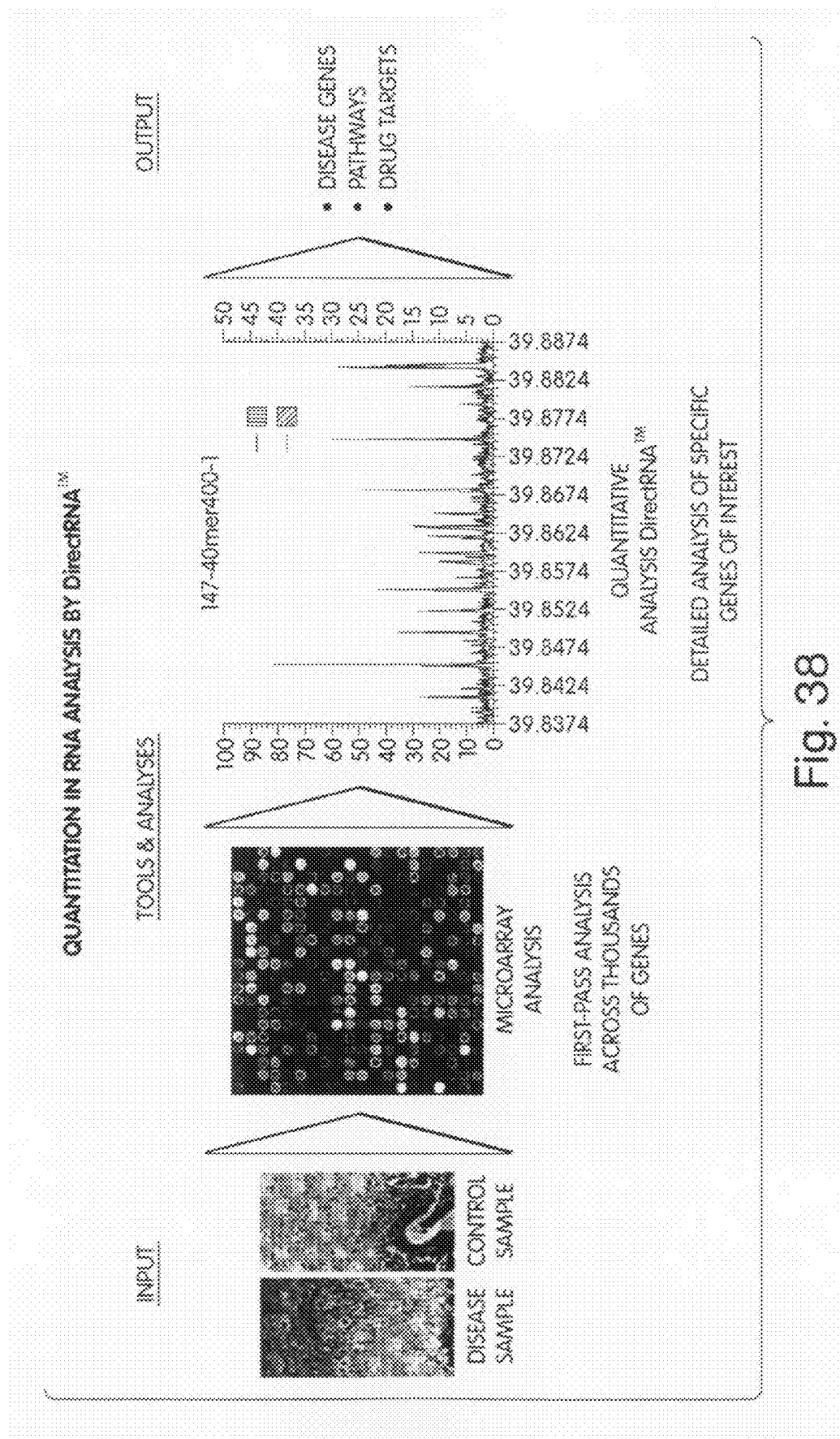
FIG. 38 is a representation of how DirectRNA™ can be used to quantitate RNA from tissue samples in combination with microarray analysis.

The results attained with DirectRNA™ were compared to those attainable with real-time PCR (RT-PCR). Total RNA samples from Hela S3 cells were analyzed on DirectRNA™ and by RT-PCR for the presence of gene X. As shown in FIG. 37, similar results were obtained from DirectRNA™ and RT-PCR. Thus while the technologies yield similar results, RT-PCR has limitations that the DirectRNA™ technology does not. For instance, RT-PCR is limited in its ability to analyze splice variants, microRNAs (e.g., endogenous RNAi), other non-coding RNAs, silent alleles (e.g., due to positioning on the X chromosome, loss of heterozygosity mutation, or methylation), rRNAs, cSNPs, snRNAs and RNA-protein interactions. FIG. 38 shows the scheme in which DirectRNA™ can be used with gene expression microarrays.

VI. Coincident Detection RNA and DNA Assays.

There are several ways of assaying RNA molecules based on the description provided herein. The following section provides schematic descriptions and accompanying figures to describe a subset of these assays.

FIGS. 39A and B demonstrate labeling and coincident peak detection of a single RNA molecule using two differentially labeled DNA probes. This method was described above as the dual probe hybridization assay. First the RNA sample is denatured in order to ensure single stranded target sequences to which the probes can bind. Then the denatured RNA is incubated with the DNA probes for a time and under conditions that allow for binding of the probes to the target in a sequence-specific manner. In FIG. 39A this is followed by a column purification step to remove unbound probe. However, as shown in FIG. 39B, this step is not necessary.

Figure 40:
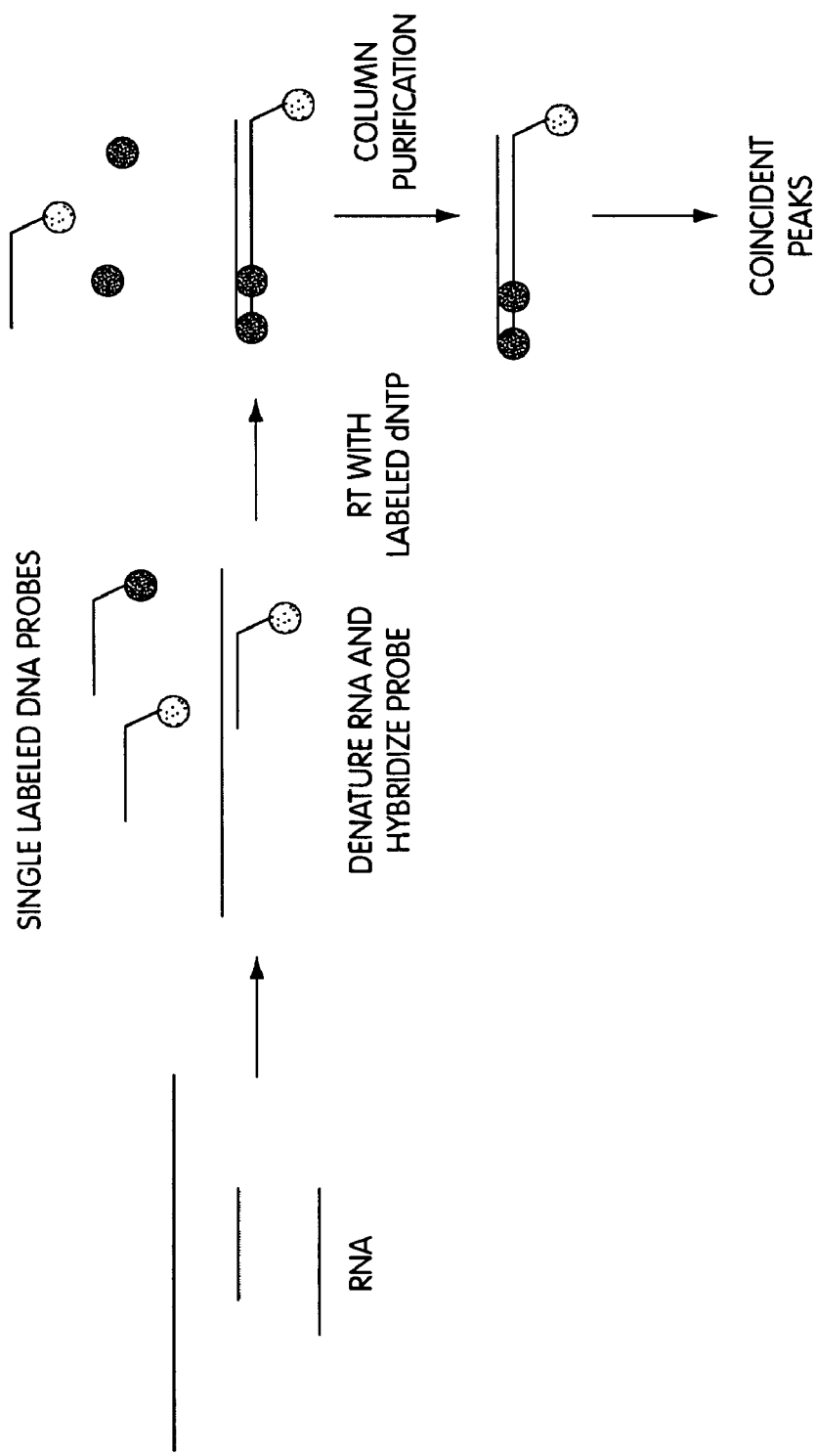
FIG. 40 is a schematic of a probe extension assay including a column purification step.

FIG. 40 demonstrates the probe extension assay described above. The RNA sample is first denatured and then incubated with single labeled DNA probes that serve as primers for the reverse transcription reaction. This mixture is then incubated with reverse transcriptase and labeled dNTPs in order to generate a reverse transcription product that is both end and internally labeled. FIG. 40 includes a column purification step prior to analysis for coincident peaks, although as stated earlier, this step may be eliminated without significant loss of sensitivity and specificity.

Figure 50:
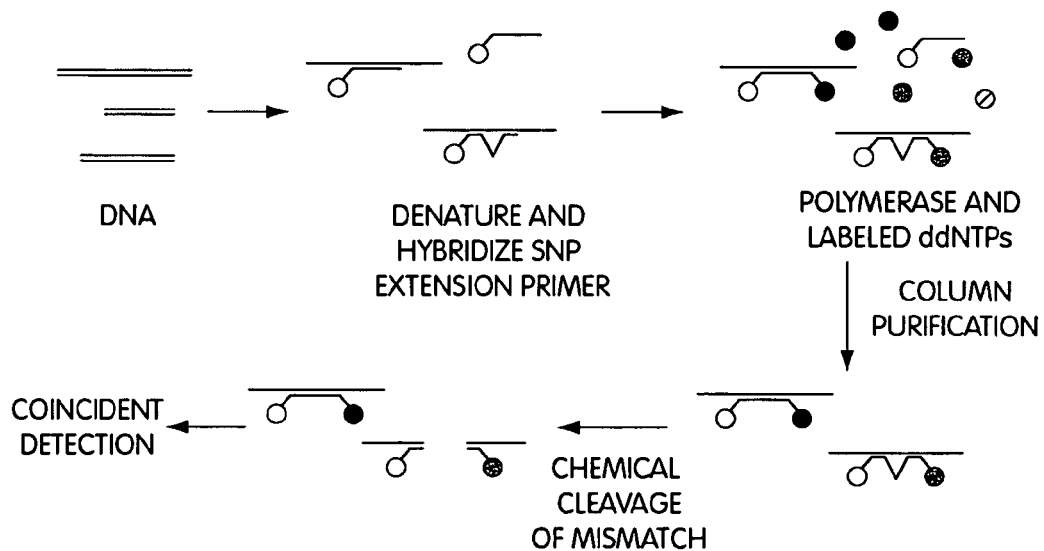
FIG. 50 is a schematic of a probe extension assay including column purification and cleavage (e.g., chemical cleavage) of mismatch regions.
Figure 51:
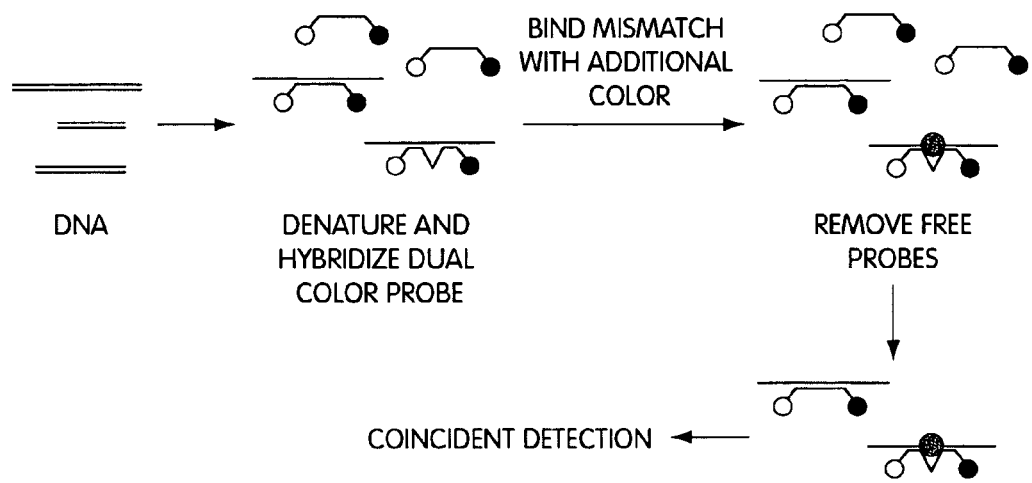
FIG. 51 is a schematic of a hybridization assay using a dual labeled probe including the use of a mismatch specific label.
Figure 52:
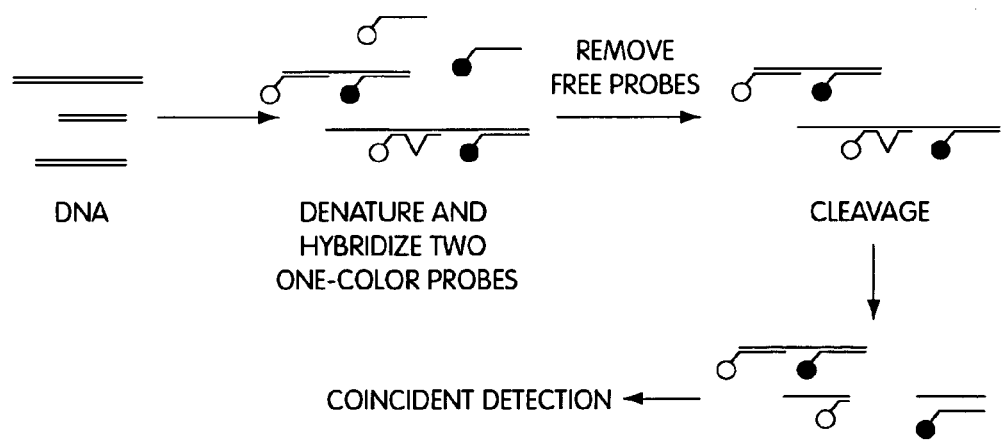
FIG. 52 is a schematic of a dual hybridization assay using singly labeled probes and including a cleavage reaction to remove mismatch containing hybrids.

A similar approach can be taken to label DNA, as shown in FIG. 50 In that example, genomic DNA is denatured and hybridized to an extension primer. Addition of polymerase and labeled ddNTPs produces new nucleic acid molecules that are at least dually labeled. Mismatch containing hybrids can be cleaved chemically or enzymatically. The resulting products as well as unbound primer and unincorporated ddNTPs can be removed by column purification, or alternatively they can be distinguished from the dually labeled hybrids using coincident detection. In a variation of this approach, rather than cleave a hybrid at the site of a mismatch, the hybrid is bound to a third probe that specifically recognizes the mismatch. Mismatched versus perfect hybrids are then distinguished based on the number of detectable coincident colors. If there are three coincident colors, this indicates a mismatch, while if there are only two coincident colors, this indicates a perfect hybrid. Three color coincident events can be excluded from the collected data. This approach is illustrated in FIG. 51. In yet another variation of this approach, denatured genomic DNA is labeled with at least two singly labeled probes. The hybridization products are then exposed to chemical or enzyme cleavage to cleave mismatches. Ultimately, only target molecules with both singly labeled probes are detected since only these will demonstrate color coincidence. This approach is demonstrated in FIG. 52.

Figure 41B:
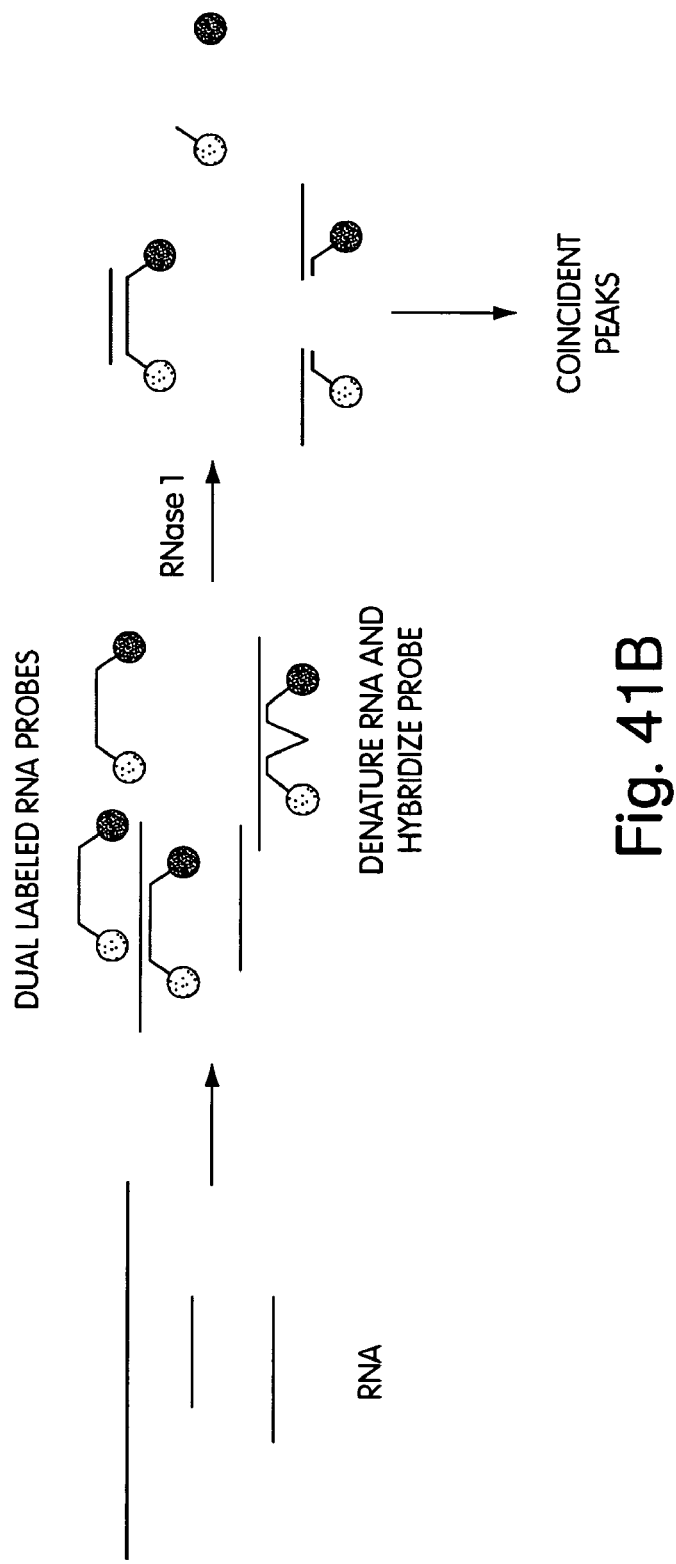
FIG. 41B is a schematic of a dual labeled RNA probe hybridization assay including an RNase I reaction and excluding a column purification step.

FIGS. 41A and B demonstrate labeling of an RNA molecule using dual labeled RNA probes. Dual labeled DNA probes could be used as well. The RNA sample is denatured and allowed to hybridize to the dual labeled probes, following which the mixture is exposed to RNase I in order to cleave any mismatch areas in the resulting hybrids. The choice of enzyme will depend upon the nature of the hybrid. Thus RNase I is particularly suited for a RNA-RNA hybrid. The RNase I cleaves single stranded RNA and thus cleaves both strands of the hybrid at a mismatch. RNase I will also digest unbound probe thereby releasing the labels, and RNA molecules that did not hybridize to the probe. The only molecules capable of providing coincident color then are those that hybridized completely with the target molecule. These molecules can be separated from cleaved hybrid fragments and released labels using column purification (as shown in FIG. 41A) although this is not necessary (as shown in FIG. 41B.

Figure 42A:
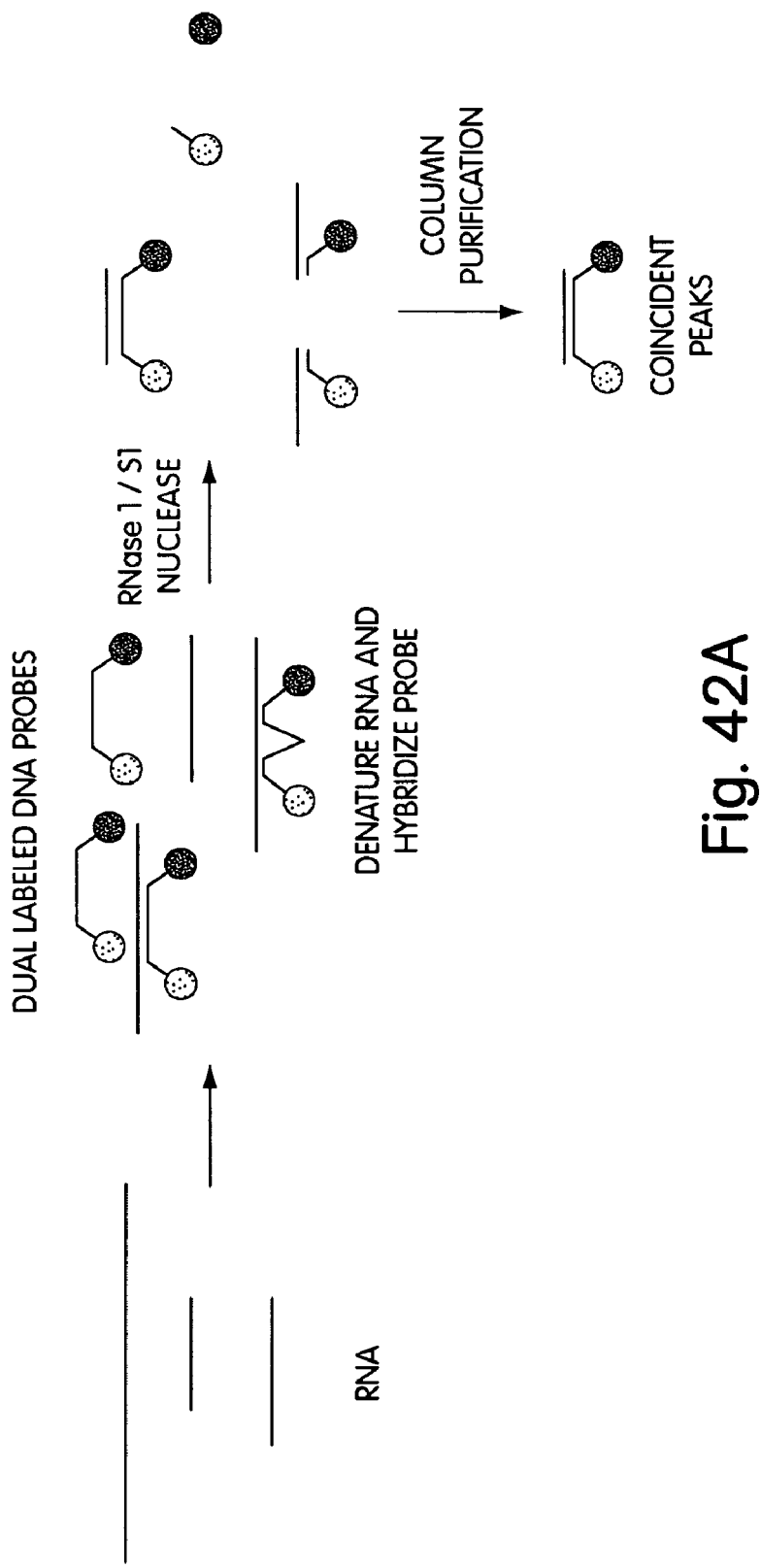
FIG. 42A is a schematic of a dual labeled DNA probe hybridization assay including an RNase I and S1 nuclease reaction and a column purification step.
Figure 42B:
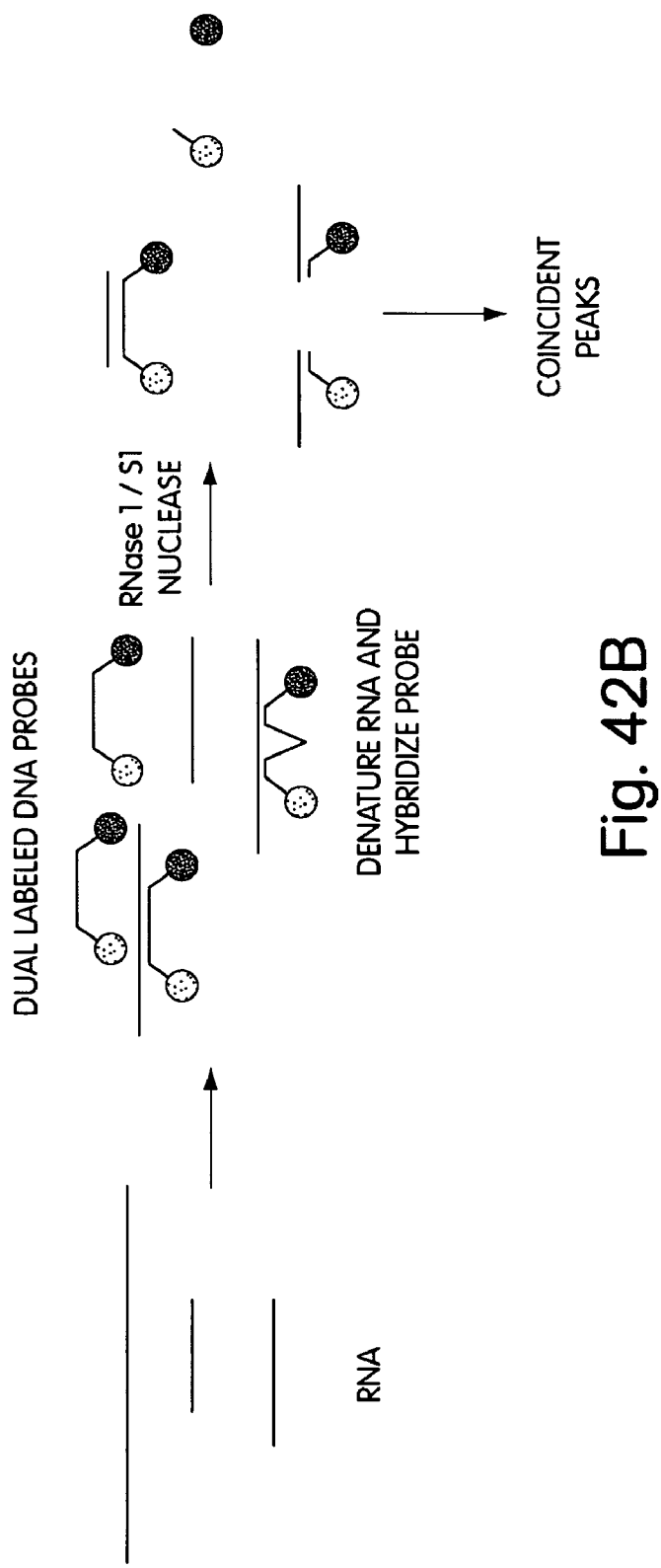
FIG. 42B is a schematic of a dual labeled DNA probe hybridization assay including an RNase I and S1 nuclease reaction and excluding a column purification step.
Figure 49:
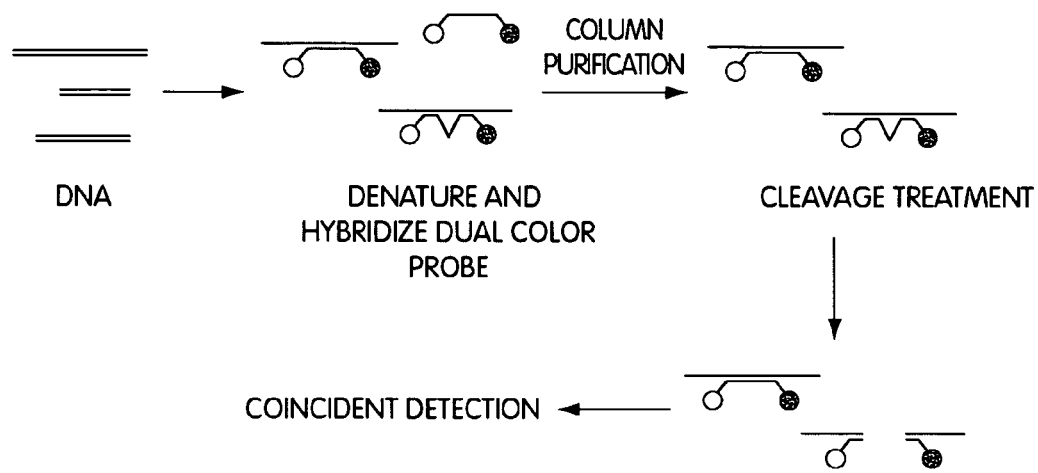
FIG. 49 is a schematic of a hybridization assay using dual labeled probes and a DNA target and including column purification and cleavage of single stranded regions.

As stated above, the latter assay can be carried out using dual labeled DNA probes, as demonstrated in FIGS. 42A and B. The only difference is that rather than the sole use of RNase I, a combination of RNase I and S1 nuclease is used to digest hybrid mismatches. RNase I cleaves the single stranded RNA at the site of the mismatch while S1 nuclease cleaves the single stranded DNA probe. The remaining steps are identical to those described above. This assay can be performed with genomic DNA as the starting material as well as demonstrated in FIG. 49. The genomic DNA is first denatured and then incubated with a dual color probe that may be RNA or DNA based. If it is DNA based, then only S1 nuclease is required to remove mismatches. However if the probe is RNA based, then both S1 nuclease and RNase I are required.

Figure 43:
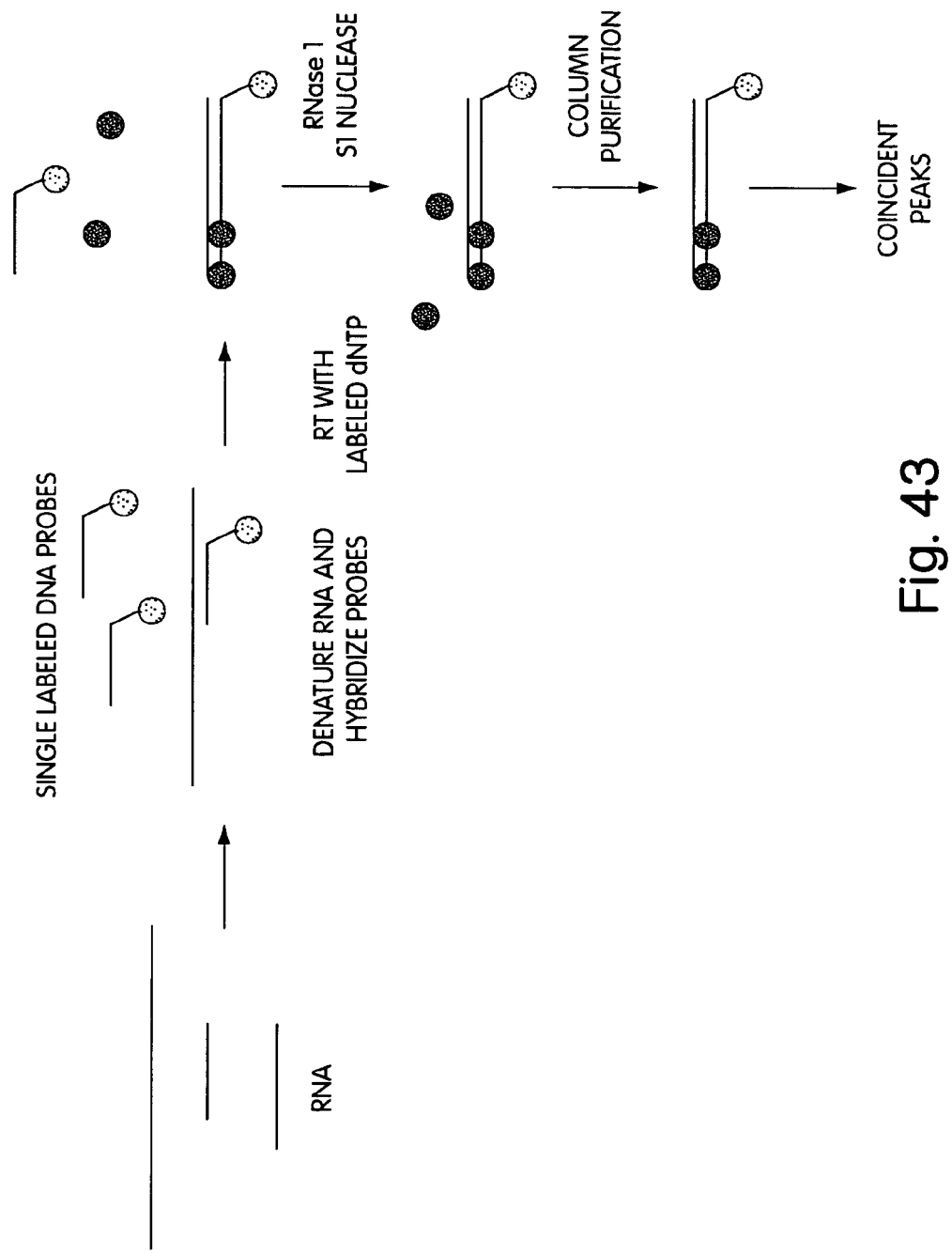
FIG. 43 is a schematic of a probe extension assay including an RNase I and S1nuclease reaction and a column purification step.

FIG. 43 demonstrates a variation on FIG. 40. The variation involves an additional step of exposing the mixture to RNase I and S1 nuclease after reverse transcription. This removes unbound probe and unbound RNA molecules.

Figure 44:
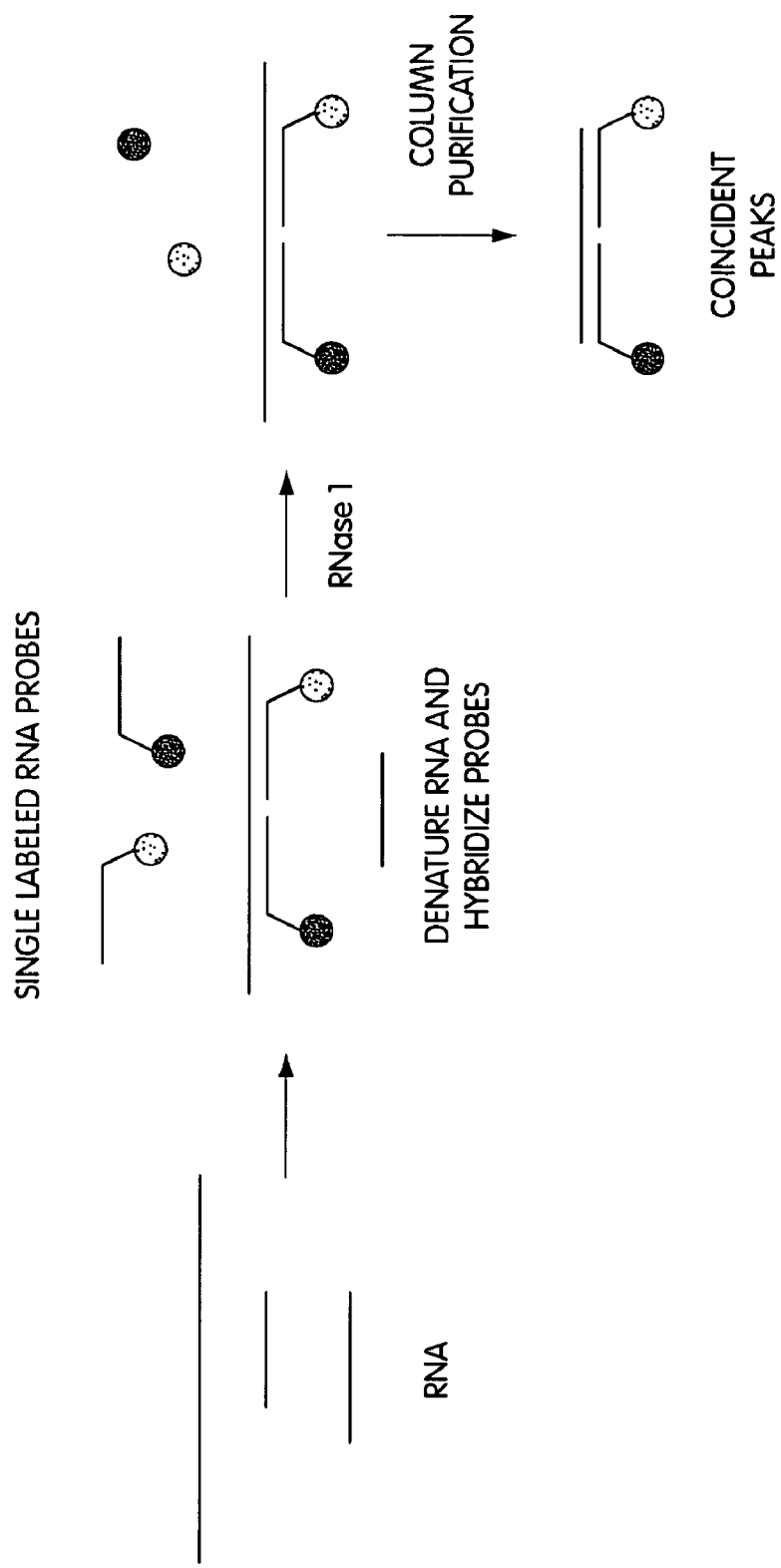
FIG. 44 is a schematic of a dual hybridization assay using single labeled RNA probes and including an RNase I reaction and a column purification step.
Figure 45:
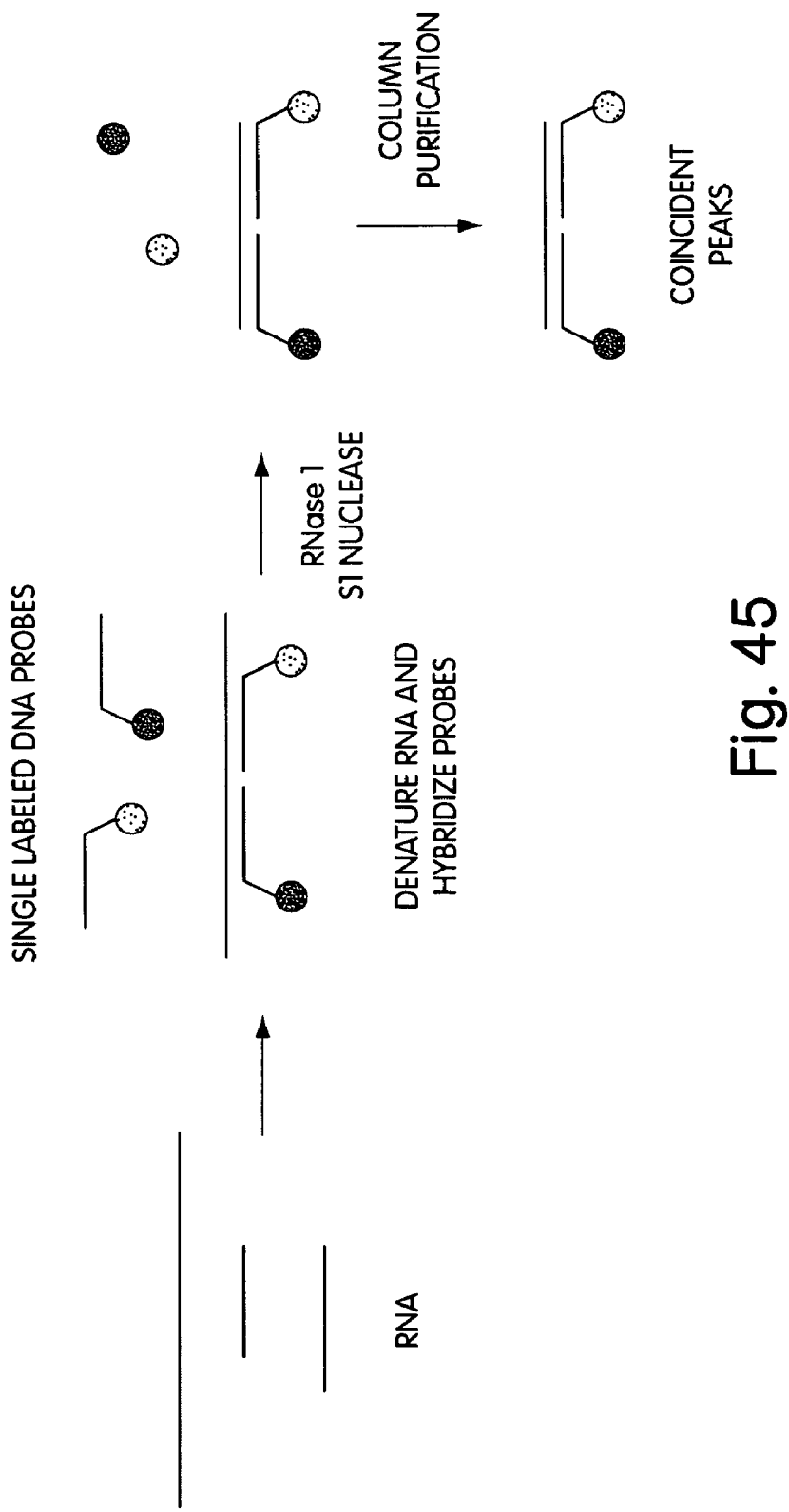
FIG. 45 is a schematic of a dual hybridization assay using single labeled DNA probes and including an RNase I and S1 nuclease reaction and a column purification step.

FIG. 44 demonstrates labeling of an RNA molecule using single labeled RNA probes. The RNA sample is denatured and then incubated with the single labeled RNA probes. The mixture is then exposed to RNase I to remove unbound RNA probes and RNA molecules, followed by an optional column purification step. FIG. 45 demonstrates a similar assay except using single labeled DNA probes rather than RNA probes. The enzyme step also includes a combination of RNase I and S1 nuclease in order to remove unbound DNA probe and unbound RNA molecules. It is important to note that in these latter two assays, the probes are designed so as to hybridize with contiguous regions of the target RNA molecule, thereby leaving no single stranded region on the target between the binding of the probes.

Figure 46:
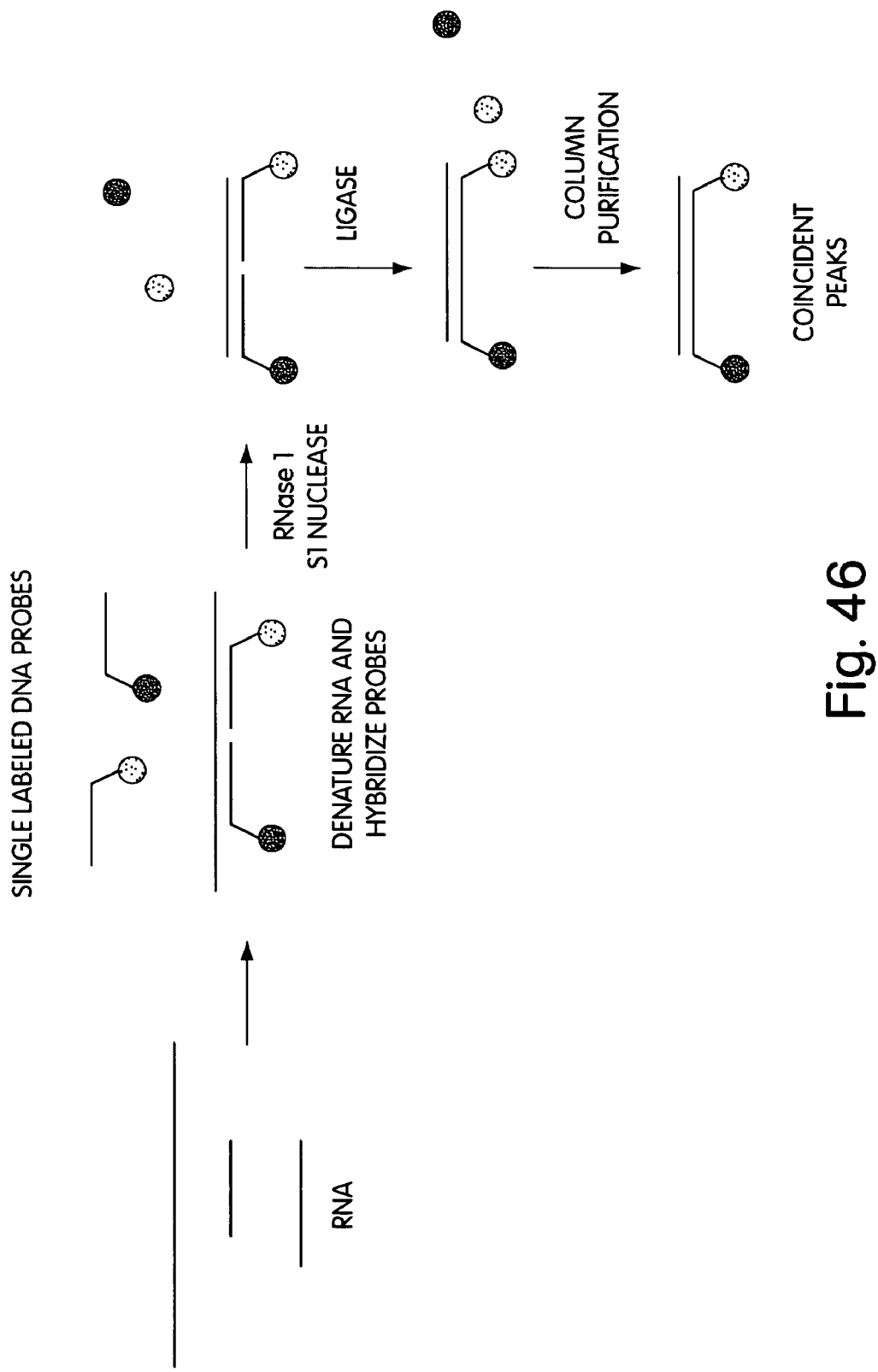
FIG. 46 is a schematic of a dual hybridization assay using single labeled DNA probes and including an RNase I and S1 nuclease reaction, a ligase reaction, and a column purification step.

FIG. 46 demonstrates the use of a ligase to ligate singly labeled probes that hybridize proximally to each other. Ligation of the singly labeled probes may increase the stability of the hybrid.

Figure 47:
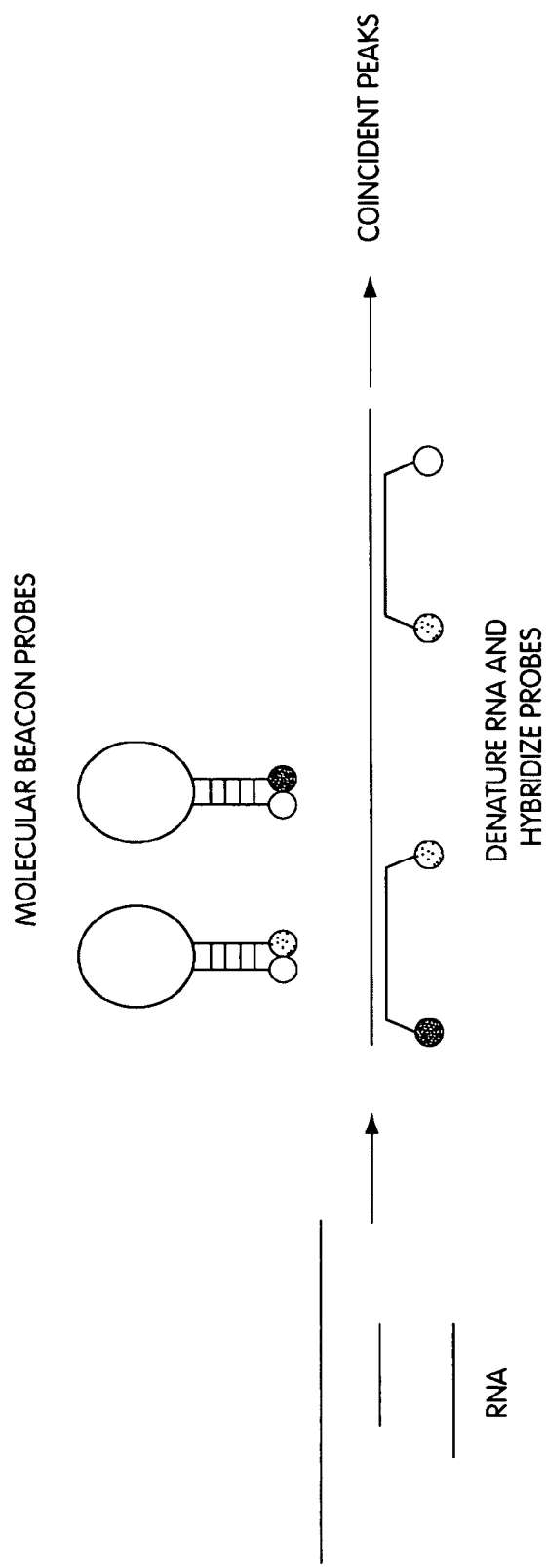
FIG. 47 is a schematic of a dual hybridization assay using molecular beacon probes.

FIG. 47 demonstrates the use of molecular beacon probes to label RNA molecules. When unbound to their targets, the probes form a hairpin structure and do not emit fluorescence since one end of the molecular beacon is a quencher molecule. However, once bound to their targets, the fluorescent and quenching ends of the probe are sufficiently separated so that the fluorescent end can now emit. Labeling an RNA molecule with two of these molecular beacon probes, each with a different fluorescent marker, results in a dually labeled RNA molecule that can be analyzed for coincident peaks.

Figure 48A:
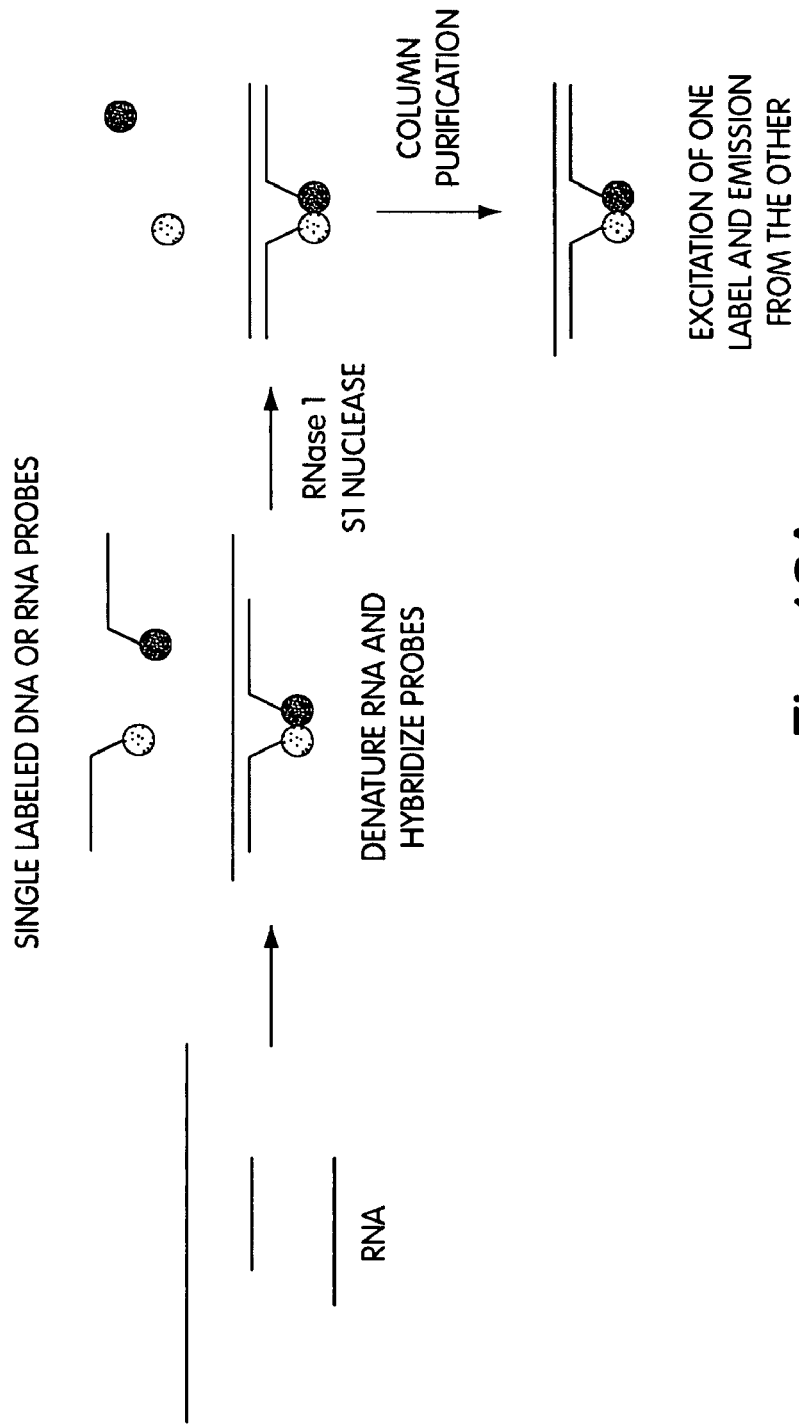
FIG. 48A is a schematic of a dual hybridization assay using DNA or RNA probes singly labeled with FRET fluorophores, and including an RNase I and S1 nuclease reaction and a column purification step.
Figure 48B:
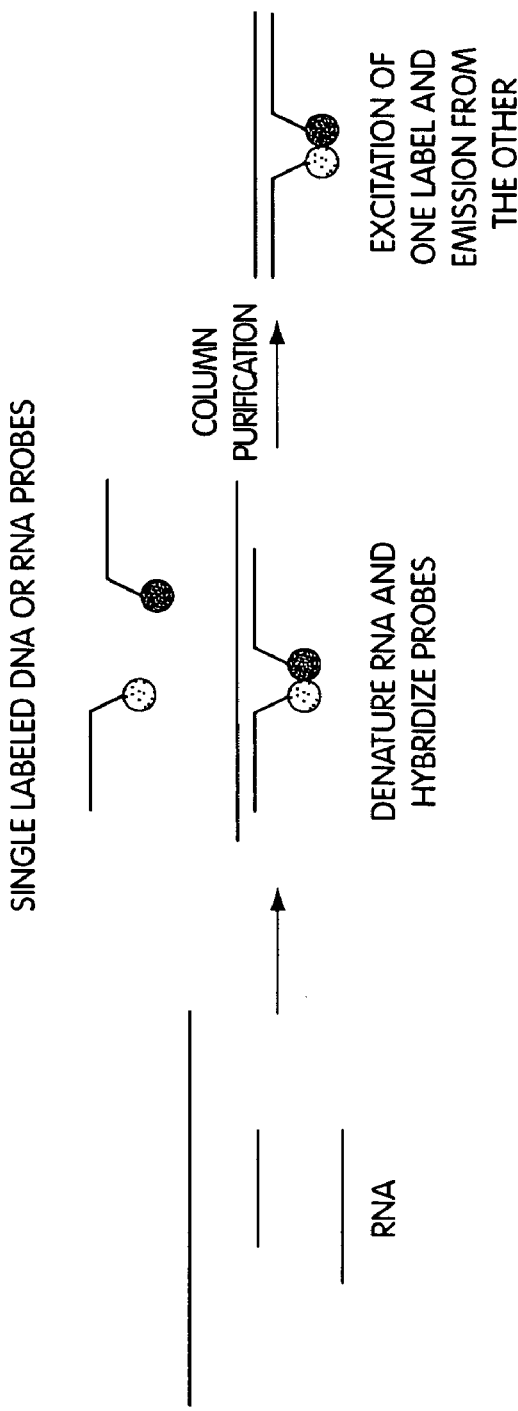
FIG. 48B is a schematic of a dual hybridization assay using DNA or RNA probes singly labeled with FRET fluorophores, and including a column purification step, and excluding an RNase I and S1 nuclease reaction.
Figure 55:
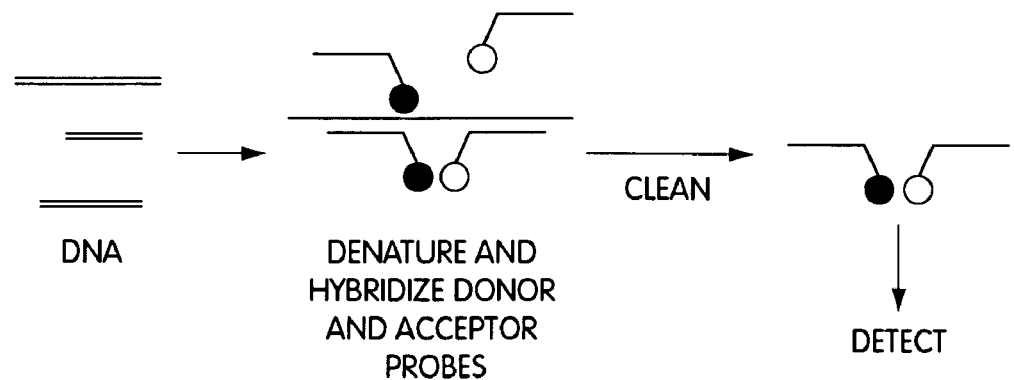
FIG. 55 is a schematic of a dual hybridization assay using probes singly labeled with FRET donor and acceptor fluorophores.

FIGS. 48A and B demonstrate the use of probes designed to hybridize contiguously so as to transfer energy from one probe label to another. When the fluorophores are located close together, and excited with a laser that excites the lower wavelength fluorophore, then emission from the second fluorophore is detectable. Most if not all the energy from the first fluorophore is captured by the second fluorophore. If it is not, then color coincident detection is possible. If on the other hand, the probes hybridize to the target at separate sites, then only emission from the first fluorophore is detected. This is the case also if only the first fluorophore hybridizes to the target. If only the second fluorophore binds to the target, then there is no emission detected at all. FIG. 48A illustrates that the samples can be cleaned using incubation with RNase I and S1 nuclease and a column purification step. FIG. 48B demonstrates the assay with only the optional column purification to remove unbound probes. The probes in either embodiment can be RNA or DNA probes. Labeling of DNA molecules using the same strategy is illustrated in FIG. 55.

Figure 53:
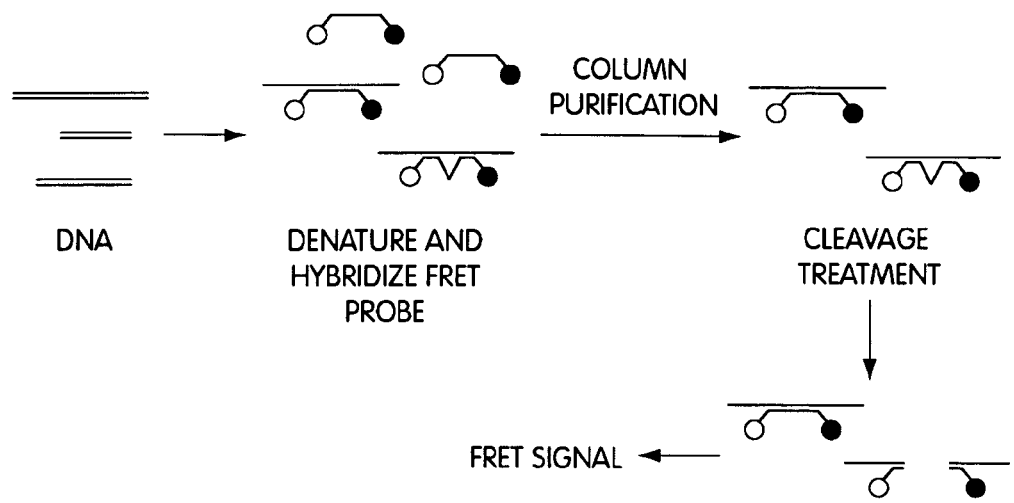
FIG. 53 is a schematic of a hybridization assay using probes dually labeled with FRET fluorophores and including cleavage of mismatch regions.

A similar approach can be taken in analysis of single DNA molecules as illustrated in FIG. 53. In this approach, genomic DNA is denatured and hybridized with a dual labeled FRET probe, and then subjected to chemical or enzymatic cleavage to cleave mismatch containing hybrids. If a FRET sequence is present, this indicates that the dual labeled FRET probe formed a perfect hybrid with the target molecule, and sequence information is therefore attainable.

Figure 54:
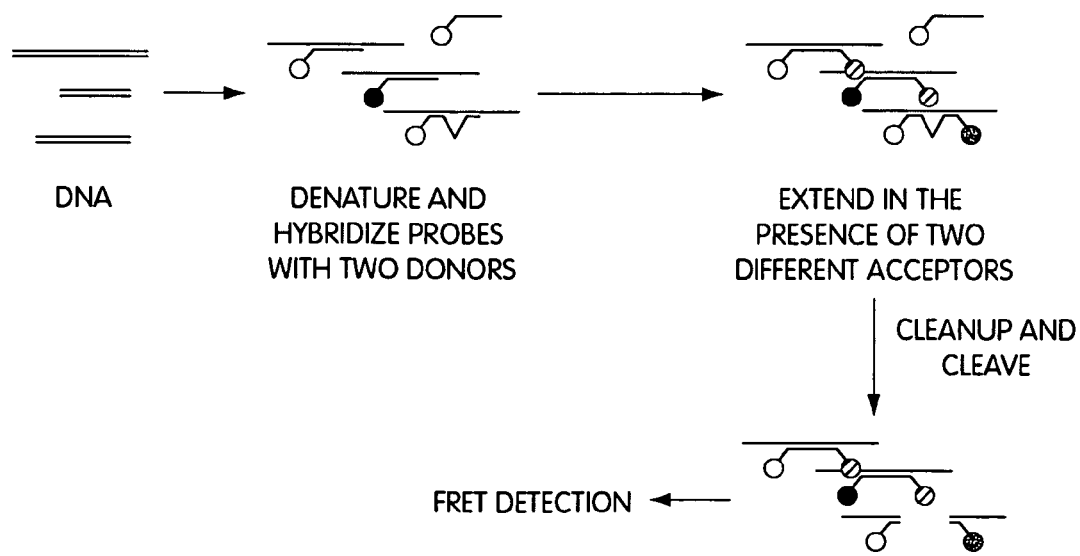
FIG. 54 is a schematic of a probe extension assay using primers labeled with different FRET donor fluorophores and extended in the presence of different FRET acceptor fluorophores, followed by a cleavage reaction to remove mismatch containing hybrids. Detection of the target is then accomplished via FRET.

The presence of homozygous or heterozygous sequences in a sample can also be determined using color coincident detection, as shown in FIG. 54. In this approach, genomic DNA is denatured and hybridized with probes containing two different donor fluorophores. The hybridized probes are then used as primers for a polymerase reaction in the presence of two different acceptor fluorophores. There exist four possible outcomes for the donor and acceptor pairings, however only two of which will be properly paired to emit acceptor fluorescence after excitation from donor emission. If emission from only one acceptor is observed, then the sample was homozygous for the target sequence. If two emissions are observed, then the sample was heterozygous for the target sequence.

Figure 56:
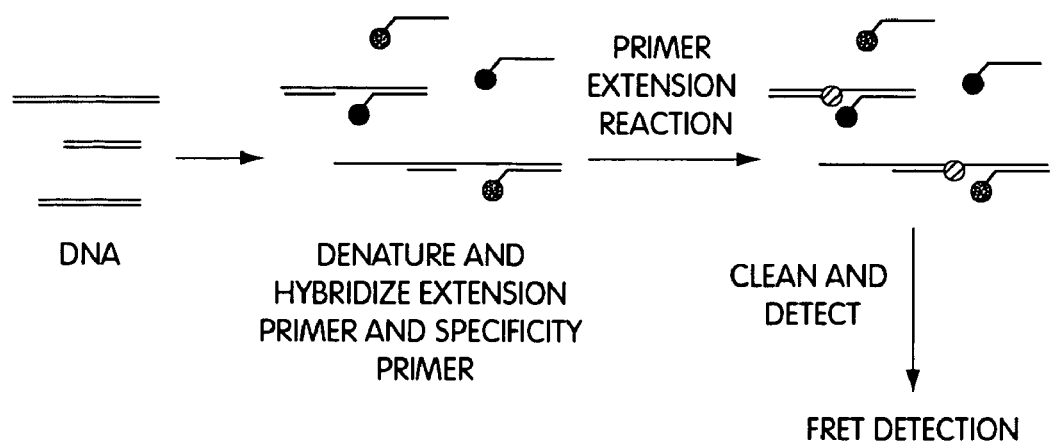
FIG. 56 is a schematic of a primer extension assay using FRET labeled primers and nucleotides. The primers are a combination of extension and specificity primers.

In FIG. 56, genomic DNA is denatured and hybridized with extension primers and a sequence-specific primer. Following a primer extension reaction and an optional clean up step, the resulting hybrids are analyzed for particular FRET signals. Specific FRET signals indicate the presence or absence of a particular SNP.

VII. Universally Labeling Oligonucleotide Probes.

The invention also provides methods for labeling of sequence-specific oligonucleotides with detectable labels such as dyes through a universal linking mechanism.

a. Universal Labeling of a Nucleic Acid Molecule.

Figure 57:
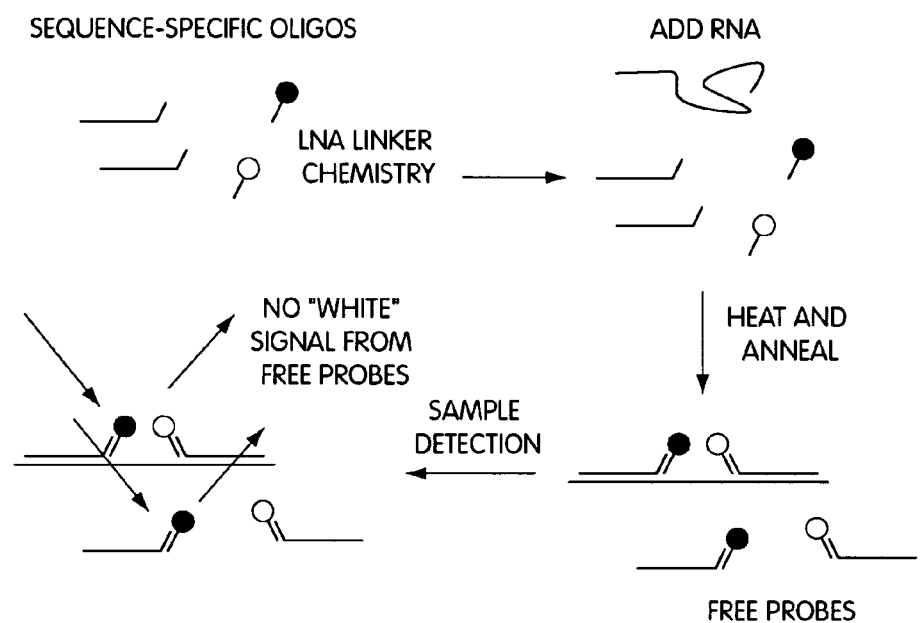
FIG. 57 is a schematic of a process for detecting and analyzing RNA molecules using a universal linker chemistry and FRET fluorophores.
Figure 58:
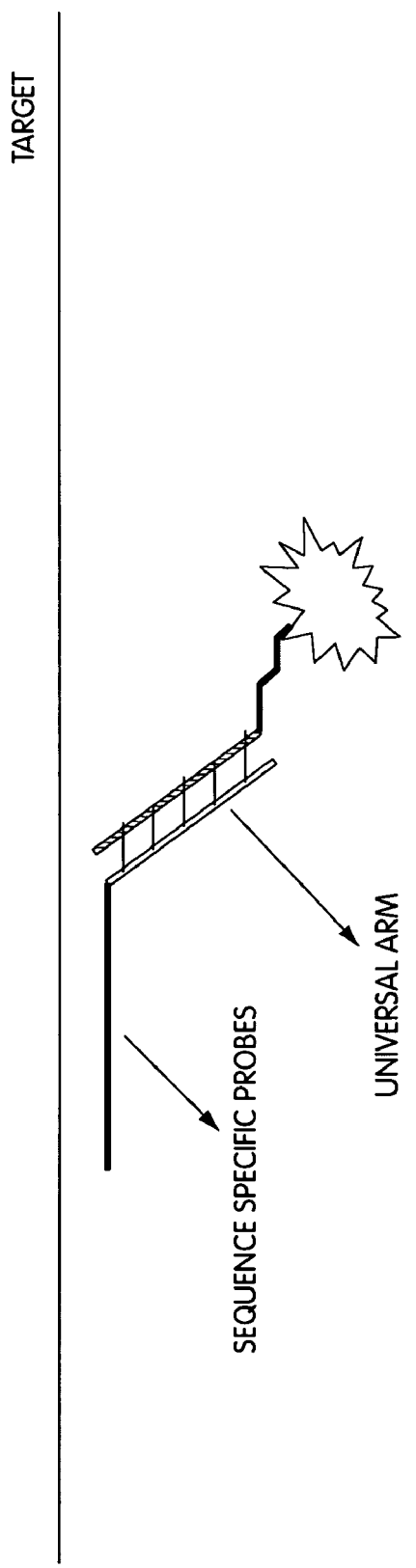
FIG. 58 is a schematic of a universal linker labeling of a sequence specific probe.

In one embodiment, short locked nucleic acid (LNA) oligonucleotides labeled with a detectable molecule (e.g., a fluorophore) are designed to hybridize to a universal arm flanking a sequence-specific probe. This configuration is illustrated in FIG. 58. The LNA can also be a PNA similarly labeled and capable of binding to its complement sequence on the universal arm flanking the sequence-specific probe. FIG. 57 demonstrates how such a universal linker may be used together with FRET technology. Sequence-specific probes are first placed in a well together with LNA or PNA labeled linkers. An RNA sample is then added to the well and allowed to hybridize to the probes. The Figure illustrates the possible outcomes following RNA addition. The dually labeled target RNA molecule can be distinguished from the free probes based on color coincident detection and FRET. If both probes are hybridized to the target within close proximity to each other then the donor fluorophore will transfer its emission energy to the acceptor fluorophore and the acceptor fluorophore will emit its characteristic wavelength. In the case of free probes, only the emission of the donor fluorophore will be observed.

b. Biotin-streptavidin Labeling.

In this approach, streptavidin labeled with a detectable marker (e.g., a fluorophore) binds to biotin that is conjugated to the sequence specific probes.

c. Antigen/Antibody Conjugates.

An antigen-antibody conjugate system such as an F1 antigen and F1 specific antibody can be used to detect nucleic acid molecules. For example, the antibody is labeled with a detectable molecule (e.g., a fluorophore). This antibody binds to the F1 antigen that is conjugated to the sequence-specific probes.

d. Increasing Signal Intensity by Using a Universal Linking Mechanism.

It is possible to achieve higher signals from a single binding event by increasing the number of detectable labels per probe. For example, both the streptavidin and F1-specific antibodies described above can be labeled with multiple detectable labels (e.g., multiple identical fluorophores). In addition, dendrimer dyes and quantum dots can be used to increase signal intensity from a single binding event.

Equivalents

It should be understood that the preceding is merely a detailed description of certain embodiments. It therefore should be apparent to those of ordinary skill in the art that various modifications and equivalents can be made without departing from the spirit and scope of the invention, and with no more than routine experimentation. It is intended to encompass all such modifications and equivalents within the scope of the appended claims.

All references, patents and patent applications that are recited in this application are incorporated by reference herein in their entirety.

We claim:

1. A method for analyzing a single nucleic acid molecule comprising exposing a single nucleic acid molecule to at least two distinguishable detectable labels present on different unit specific markers for a time sufficient to allow the detectable labels to bind to the single nucleic acid molecule, and passing the single nucleic acid molecule in flow through a diffraction-limited detection spot, thereby analyzing the single nucleic acid molecule for a coincident event using a single molecule detection system by detecting two separate and distinguishable signals from the at least two distinguishable detectable labels, wherein the single nucleic acid molecule is present at a concentration of 400 fM or greater, the coincidence event indicates that the at least two distinguishable detectable labels are bound to the single nucleic acid molecule, the coincident event is a color coincident event, and the method analyzes 20-20,000 single nucleic acid molecules per minute.

2. The method of claim 1, wherein the single nucleic acid molecule is denatured to a single stranded form.

3. The method of claim 1, wherein the single nucleic acid molecule is an RNA.

4. The method of claim 1, wherein the single nucleic acid molecule is linearized or stretched prior to analysis.

5. A method for analyzing a single nucleic acid molecule comprising exposing a single nucleic acid molecule to at least two distinguishable detectable labels for a time sufficient to allow the detectable labels to bind to the single nucleic acid molecule, exposing the single nucleic acid molecule and detectable labels to a chemical or enzymatic single stranded cleavage reaction, and then analyzing the single nucleic acid molecule for a coincident event using a single molecule detection system by detecting two separate and distinguishable signals from the at least two distinguishable detectable labels, wherein the coincidence event indicates that the at least two distinguishable detectable labels are bound to the single nucleic acid molecule, and the coincident event is a color coincident event.

6. The method of claim 5, wherein the enzymatic single stranded cleavage reaction uses a single stranded RNA nuclease, a single stranded DNA nuclease, or a combination thereof.

7. The method of claim 1, further comprising a column purification step.

8. The method of claim 1, wherein the single nucleic acid molecule is present in a nanoliter volume.

9. The method of claim 1, wherein the single nucleic acid molecule is present in at a frequency of 1 in 1,000,000 molecules in an RNA sample.

10. The method of claim 1, wherein each of the at least two distinguishable detectable labels is present on a unit specific marker that is a DNA, RNA, PNA, LNA or a combination thereof.

11. The method of claim 1, further comprising exposing the nucleic acid molecule to a ligase prior to analysis using the single molecule detection system.

12. The method of claim 1, wherein unbound detectable labels are not removed prior to analysis using the single molecule detection system.

13. The method of claim 1, wherein the detectable labels are provided as molecular beacon probes.

14. The method of claim 1, wherein at least one detectable label is attached to a nucleic acid molecule hybridized to a universal linker attached to a unit specific marker.

15. A method for analyzing a single nucleic acid molecule comprising exposing a single nucleic acid molecule to at least two distinguishable detectable labels for a time sufficient to allow the detectable labels to bind to the single nucleic acid molecule wherein the at least two distinguishable detectable labels are present on the same unit specific marker, analyzing the single nucleic acid molecule for a coincident event using a single molecule detection system wherein the coincidence event indicates that the at least two distinguishable detectable labels are bound to the single nucleic acid molecule, and exposing the single nucleic acid molecule to a third detectable label that binds specifically to a mismatch between the single nucleic acid molecule and the unit specific marker, wherein a coincident event between the first, second and third detectable labels is indicative of a mismatch.

16. A method for analyzing a single nucleic acid molecule comprising exposing a single nucleic acid molecule to at least two distinguishable detectable labels for a time sufficient to allow the detectable labels to bind to the single nucleic acid molecule, analyzing the single nucleic acid molecule for a coincident event using a single molecule detection system, and exposing the single nucleic acid molecule and detectable labels to an enzymatic single stranded cleavage reaction that uses RNase I prior to analyzing the single nucleic acid molecule, wherein the coincidence event indicates that the at least two distinguishable detectable labels are bound to the single nucleic acid molecule.

17. A method for analyzing a single nucleic acid molecule comprising exposing a single nucleic acid molecule to at least two distinguishable detectable labels for a time sufficient to allow the detectable labels to bind to the single nucleic acid molecule, analyzing the single nucleic acid molecule for a coincident event using a single molecule detection system, and exposing the single nucleic acid molecule and detectable labels to an enzymatic single stranded cleavage reaction that uses S1 nuclease prior to analyzing the single nucleic acid molecule, wherein the coincidence event indicates that the at least two distinguishable detectable labels are bound to the single nucleic acid molecule.

18. A method for analyzing a single nucleic acid molecule comprising exposing a single nucleic acid molecule to at least two distinguishable detectable labels for a time sufficient to allow the detectable labels to bind to the single nucleic acid molecule in the presence of a polymerase, a labeled unit specific marker and labeled nucleotides, provided the unit specific marker and nucleotides are differentially labeled with the at least two distinguishable detectable labels, and analyzing the single nucleic acid molecule for a coincident event using a single molecule detection system, wherein the coincidence event indicates that the at least two distinguishable detectable labels are bound to the single nucleic acid molecule.

19. The method of claim 18, wherein a new nucleic acid molecule is formed starting at the unit specific marker and is complementary to the single nucleic acid molecule.

20. The method of claim 19, wherein the new nucleic acid molecule has a signal intensity proportional to its length, and wherein the method is a method of determining integrity of the single nucleic acid molecule.

21. The method of claim 18, wherein the polymerase is a DNA polymerase.

22. The method of claim 19, wherein the polymerase is a reverse transcriptase.

23. A method for analyzing a single nucleic acid molecule comprising exposing a single nucleic acid molecule to at least two distinguishable detectable labels for a time sufficient to allow the detectable labels to bind to the single nucleic acid molecule in the presence of a polymerase, a labeled unit specific marker and labeled nucleotides, provided the unit specific marker and nucleotides are differentially labeled with the at least two distinguishable detectable labels that are a FRET fluorophore pair, and analyzing the single nucleic acid molecule for a coincident event using a single molecule detection system, wherein the coincidence event indicates that the at least two distinguishable detectable labels are bound to the single nucleic acid molecule.

24. The method of claim 23, wherein one detectable label is attached to the unit specific marker and is a first FRET fluorophore, and the other detectable label is incorporated into a new nucleic acid molecule hybridized to the single nucleic acid molecule and is the donor or acceptor of the first FRET fluorophore.

25. The method of claim 5, 15, 16, 17, 18 or 23, wherein the single nucleic acid molecule is passed in flow through a diffraction-limited detection spot and is thereby analyzed.

26. The method of claim 5, 15, 16, 17, 18 or 23, wherein the single nucleic acid molecule is present at a concentration of 400 fM or greater.

27. The method of claim 5, 15, 16, 17, 18 or 23, wherein the method analyzes 20-20,000 single nucleic acid molecules per minute.

28. The method of claim 15, 16, 17 or 18, wherein analyzing the single nucleic acid molecule comprises detecting two separate and distinguishable signals from the at least two distinguishable detectable labels.

* * * * *